(12) United States Patent
Chen et al.

(10) Patent No.: US 8,178,570 B2
(45) Date of Patent: May 15, 2012

(54) TIE-2 MODULATORS AND METHODS OF USE

(75) Inventors: Jeff Chen, San Francisco, CA (US); Lisa Esther Dalrymple, San Francisco, CA (US); Sergey Epshteyn, Fremont, CA (US); Timothy Patrick Forsyth, Hayward, CA (US); Tai Phat Huynh, Oakland, CA (US); James William Leahy, San Leandro, CA (US); Brian Hugh Ridgway, Belmont, CA (US); Grace Mann, Brisbane, CA (US); Larry W. Mann, Richland, MI (US); Craig Stacy Takeuchi, Burlingame, CA (US); Joan C. Sangalang, Mountain View, CA (US)

(73) Assignee: Exelixis, Inc., South San Francisco, CA (US)

( * ) Notice: Subject to any disclaimer, the term of this patent is extended or adjusted under 35 U.S.C. 154(b) by 1570 days.

(21) Appl. No.: 10/552,424

(22) PCT Filed: Apr. 8, 2004

(86) PCT No.: PCT/US2004/010626
§ 371 (c)(1),
(2), (4) Date: Jul. 5, 2006

(87) PCT Pub. No.: WO2004/091480
PCT Pub. Date: Oct. 28, 2004

(65) Prior Publication Data
US 2006/0293342 A1    Dec. 28, 2006

Related U.S. Application Data

(60) Provisional application No. 60/461,471, filed on Apr. 9, 2003.

(51) Int. Cl.
*A01N 43/64* (2006.01)
*A01N 43/54* (2006.01)
*A61K 31/41* (2006.01)
*C07D 239/42* (2006.01)
*C07D 401/04* (2006.01)
*C07D 249/08* (2006.01)

(52) U.S. Cl. ............. 514/383; 514/256; 548/262.2

(58) Field of Classification Search ............... 514/256, 514/383; 548/262.2
See application file for complete search history.

(56) References Cited

U.S. PATENT DOCUMENTS

| 3,978,054 A | 8/1976 | Baldwin et al. |
| 5,089,499 A | 2/1992 | Barker et al. |
| 5,284,860 A | 2/1994 | Ozaki et al. |

FOREIGN PATENT DOCUMENTS

| EP | 0074229 A1 | 3/1983 |
| GB | 1110360 | 4/1968 |
| JP | 2007-223901 | 9/2007 |
| WO | 02/032896 A1 | 4/2002 |
| WO | 02/088097 A1 | 11/2002 |
| WO | 02/100826 A2 | 12/2002 |
| WO | WO 2004056789 A1 * | 7/2004 |

OTHER PUBLICATIONS

Bennett, B.L. Eur. Respir. J. Sep. 2006, vol. 28, Iss. 3, pp. 651-661.*
Vippagunta et al. Advanced Drug Delivery Reviews, 2001, vol. 48, pp. 3-26.*
Beaumont et al. Current Drug Metabolism, 2003, vol. 4, pp. 461-485.*
Supplementary Partial European Search Report for European Application EP 04759191, completed by The Hague on May 28, 2008.
Fauci et al., "Harrison's Principles of Internal Medicine: Chapter 284, Peptic Ulcer and Related Disorders", 1998, ISBN 0-07-030291-5, pp. 1596-1597.

* cited by examiner

*Primary Examiner* — Samira Jean-Louis
(74) *Attorney, Agent, or Firm* — McDonnell Boehnen Hulbert & Berghoff LLP

(57) ABSTRACT

The present invention provides compounds for modulating protein kinase enzymatic activity for modulating cellular activities such as proliferation, differentiation, programmed cell death, migration and chemoinvasion. Compounds of the invention inhibit, regulate and/or modulate kinases, particularly Tie-2. Methods of using the compounds and pharmaceutical compositions thereof to treat kinase-dependent diseases and conditions are also an aspect of the invention.

30 Claims, No Drawings

TIE-2 MODULATORS AND METHODS OF USE

CROSS-REFERENCE TO RELATED APPLICATIONS

This application claims priority to U.S. provisional patent application 60/461,471 filed on Apr. 9, 2003, entitled "Tie-2 Modulators and Methods of Use," naming Chen, Jeff et. al as inventors; which is hereby incorporated by reference in its entirety for all purposes.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds that inhibit, regulate and/or modulate kinases, particularly Tie-2. Kinase receptor signal transduction pathways related to the changes in cellular activities as mentioned above are modulated using compounds of the invention. Methods of using the compounds to treat kinase-dependent diseases and conditions are also an aspect of the invention.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, BB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is Tie-2. Tie-2 (also called TEK) is a member of the receptor tyrosine kinase (RTK) family, which is expressed primarily in endothelial cells and early hemopoietic cells, and plays a critical role in the processes of vasculogenesis and angiogenesis. As such, Tie-2 has been shown to participate in endothelial cell migration, sprouting, survival and periendothelial cell recruitment during angiogenesis.

The angiopoietin family of growth factors regulates Tie-2 activity through a combination of agonistic and antagonistic extracellular ligands. Binding of the ligands, Angiopoietin-1 (Ang-1) or Ang-4 by Tie-2 induces autophosphorylation resulting in an increase of receptor dependent signaling, while binding to Ang-2 and Ang-3 results in down regulation of receptor activity. Ang-1 signaling through Tie-2 facilitates later stages of vascular development by modulating cell-cell, and cell-matrix interactions, resulting in the survival and stabilization of newly formed blood vessels.

Tumor growth progression requires the recruitment of new blood vessels into the tumor from preexisting vessels. Accordingly, Tie-2 expression has been demonstrated on a wide variety of tumor types including ovarian, breast, renal, prostate, lung, thyroid, myeloid leukemia, hemangiomas, melanomas, astrocytomas, and glioblastomas. Tie-2 activation has also been linked to venous malformations (VM), the most common form of vascular morphogenesis in humans. As well, an activating mutation in the kinase domain of Tie-2 occurs in multiple families who exhibit a dominantly inherited form of VM. Tie-2 has been linked to multiple cancer types, including ovarian, breast, renal, prostate, lung, thyroid, myeloid leukemia, hemangiomas, melanomas, astrocytomas, and glioblastomas (See: Shirkawa et al Int J Cancer 2002 Jun. 20; 99(6):821-8; Tanka et al Clin Cancer Res 2002 May; 8(5):1125-31; Mitsutake et al Thyroid 2002 February; 12(2): 95-9; Muller et al Leuk Res 2002 February; 26(2):163-8; Yu et al Am J Pathol 2001 December; 159(6):2271-80; Pomyje et al Melanoma Res 2001 December; 11(6):639-43; Harris et al Clin Cancer Res 2001 July; 7(7):1992-7; Wrumback et al Anticancer Res 2000 November-December; 20(6D):5217-20; Ding et al Deuro-oncol 2001 January; 3(1):1-10; Takahama et al Clin Cancer Res 1999 September; 5(9):2506-10; Stratmann et al Am J Pathol 1998 November; 153(5):1549-66; and, Kukk et al Br J Haematol 1997 July; 98(1):195-203). Additionally, activation of Tie-2 has been linked to the vascular dysmorphogenesis syndrome, venous malformation (See: Vikkula et al Cell 1996 December; 87(1):1181-1190). Thus modulation of Tie-2 is desirable as a means to treat cancer and cancer-related disease.

Accordingly, the identification of small-molecule compounds that specifically inhibit, regulate and/or modulate the signal transduction of kinases, particularly Tie-2, is desirable as a means to treat or prevent disease states associated with abnormal cell proliferation and angiogenesis, and is an object of this invention.

SUMMARY OF THE INVENTION

The present invention provides compounds for modulating kinase activity and methods of treating diseases mediated by kinase activity, in particular Tie-2, utilizing the compounds and pharmaceutical compositions thereof. Diseases mediated by kinase activity are from herein referred to as "kinase-dependent diseases or conditions" (see definition in detailed description of invention below). Inhibitors that are selective for Tie-2 are included in this invention.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients. These and other features and advantages of the present invention will be described in more detail below.

DETAILED DESCRIPTION OF THE INVENTION

The compositions of the invention are used to treat diseases associated with abnormal and or unregulated cellular activities. Disease states which can be treated by the methods and compositions provided herein include, but are pot limited to, cancer (further discussed below), immunological disorders such as rheumatoid arthritis, graft-host diseases, multiple sclerosis, psoriasis; cardiovascular diseases such as atherosclerosis, myocardioinfarction, ischemia, pulmonary hypertension, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally," but proliferation and migration enhancement may be desired. Alternatively, reduction in "normal" cell proliferation and/or migration rate may be desired.

The present invention comprises a method of treating a kinase-dependent disease or condition comprising administering to a mammal in need of such treatment a therapeutically effective amount of a compound according to Formula I,

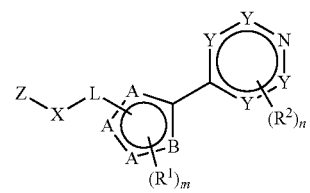

or a pharmaceutically acceptable salt, hydrate, or prodrug thereof, wherein, $R^1$ and $R^2$, at each occurrence, are independently selected from —H, halogen, —CN, —NH$_2$, —CF$_3$, —NO$_2$, —OR$^6$, —N(R$^6$)R$^7$, —N(R$^6$)N(R$^6$)R$^7$, —S(O)$_{0-2}$R$^7$, —SO$_2$N(R$^6$)R$^7$, —CO$_2$R$^6$, —C(O)N(R$^6$)R$^7$, —N(R$^6$)SO$_2$R$^7$, —N(R$^6$)C(O)R$^7$, —N(R$^6$)C(O)C$_{0-6}$alkyl-N(R$^6$)R$^7$, —N(R$^6$)CO$_2$R$^7$, —C(O)R$^6$, optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl;

m and n are each zero to four;

A is selected from —N═, —N(H)—, —C(H)═, —O—, and —S—;

B is selected from A, —C(H)═C(H)—, —C(H)═N—, —N═C(H)—, —N═N—;

L is optionally substituted C$_{1-6}$ alkylene;

X is —N(R$^3$)—;

$R^3$ is selected from —H, optionally substituted alkyl, optionally substituted aryl, optionally substituted aryl C$_{1-6}$ alkyl, optionally substituted heterocyclyl, and optionally substituted heterocyclyl C$_{1-6}$ alkyl;

Z is selected from R$^4$, R$^4$C(═O)—, R$^3$(R$^4$)NC(═O)—, R$^4$SO$_2$—, R$^3$(R$^4$)NSO$_2$—, and R$^4$C(═NR$^5$)—;

$R^4$ is selected from optionally substituted aryl, optionally substituted aryl C$_{1-6}$ alkyl, optionally substituted heterocyclyl, and optionally substituted heterocyclyl C$_{1-6}$ alkyl;

optionally R³ and R⁴, together with the atoms to which they are attached and any additional atoms that link Z with X, are combined to form a first optionally substituted five- to seven-membered heterocyclyl ring, said first optionally substituted five- to seven-membered heterocyclyl ring optionally containing at least one additional heteroatom selected from N, O, S, and P;

$R^5$ is selected from —H, —NO₂, —NH₂, —N(R⁶)R⁷, —CN, —OR⁶, and optionally substituted $C_{1-6}$ alkyl;

Y is independently either =C(H)— or =N—, provided that there are no more than three of =N— in the ring bearing Y;

each R⁶ is —H or R⁷;

each R⁷ is independently selected from optionally substituted $C_{1-6}$ alkyl, optionally substituted aryl, optionally substituted aryl $C_{1-6}$ alkyl, optionally substituted heterocyclyl, and optionally substituted heterocyclyl $C_{1-6}$ alkyl; and optionally R⁶ and R⁷, when taken together with a common nitrogen to which they are attached, form a second optionally substituted five- to seven-membered heterocyclyl ring, said second optionally substituted five- to seven-membered heterocyclyl ring optionally containing at least one additional heteroatom selected from N, O, S, and P.

In one example, the method is according to paragraph [0021], wherein the compound is according to one of,

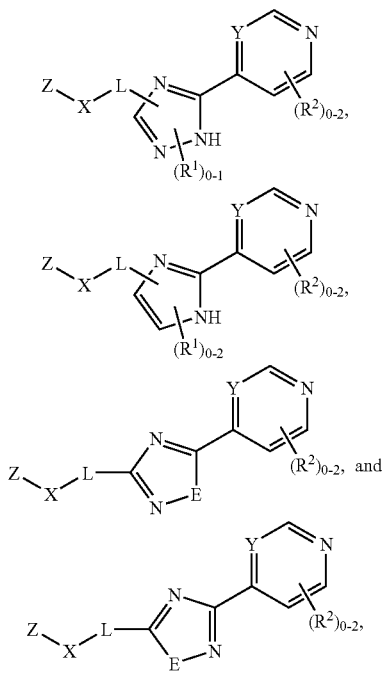

wherein E is —S— or —O—.

In another example, the method is according to paragraph [0022], wherein L is optionally substituted $C_{1-4}$ alkylene.

In another example, the method is according to paragraph [0023], wherein R³ is either —H or optionally substituted alkyl.

In another example, the method is according to paragraph [0024], wherein Z is either R⁴C(=O)— or R⁴SO₂—.

In another example, the method is according to paragraph [0025], wherein the compound is according to one of,

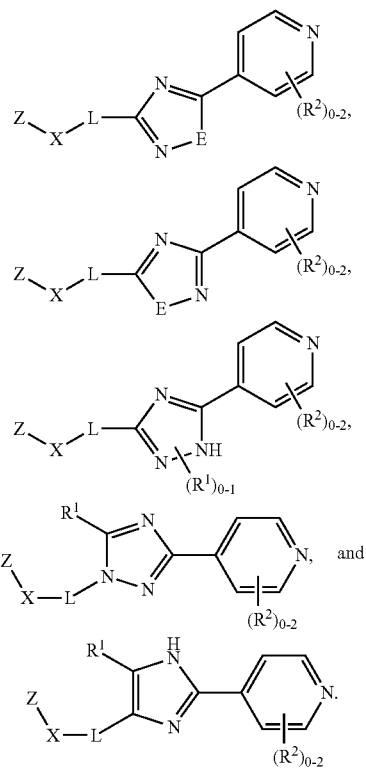

In another example, the method is according to paragraph [0026], wherein R⁴ is either optionally substituted aryl $C_{1-6}$ alkyl or optionally substituted heteroaryl $C_{1-6}$ alkyl.

In another example, the method is according to paragraph [0027], wherein R¹ is selected from —H, optionally substituted $C_{1-6}$ alkyl optionally substituted aryl, and optionally substituted heteroaryl.

In another example, the method is according to paragraph [0028], wherein L is optionally substituted —CH₂CH₂—.

In another example, the method is according to paragraph [0029], wherein R³ is optionally substituted cycloalkyl or optionally substituted branched alkyl.

In another example, the method is according to paragraph [0030], wherein Z is R⁴C(=O)—.

In another example, the method is according to paragraph [0031], wherein L is —CH₂CH₂—.

In another example, the method is according to paragraph [0032], wherein R⁴ is optionally substituted aryl $C_{1-6}$ alkyl.

In another example, the method is according to paragraph [0033], wherein R⁴ is optionally substituted —CH₂-naphthylene.

In another example, the method is according to paragraph [0034], wherein R⁴ is optionally substituted —CH₂-1-naphthylene.

In another example, the method is according to paragraph [0035], wherein R⁴ is —CH₂-1-naphthylene.

In another example, the method is according to paragraph [0036], wherein at least one of R² is selected from —NH₂, —N(R⁶)R⁷, —N(R⁶)N(R⁶)R⁷, —N(R⁶)C(O)R⁷, —N(R⁶)C(O)$C_{0-6}$alkyl-N(R⁶)R⁷, and —N(R⁶)CO₂R⁷.

In another example, the method is according to paragraph [0037], wherein said at least one of R² is ortho to the nitrogen of the pyridine ring bearing R².

In another example, the method is according to paragraph [0021], wherein the compound is selected from Table 1.

TABLE 1

| Entry | Name |
|---|---|
| 1 | N-{2-[5-(3-chloro-4-hydroxyphenyl)-3-pyridin-4-yl-1H-1,2,4-triazol-1-yl]ethyl}-N-cyclopentyl-2-naphthalen-1-ylacetamide |
| 2 | ethyl {5-[3-chloro-4-(methyloxy)phenyl]-3-pyridin-4-yl-1H-1,2,4-triazol-1-yl}acetate |
| 3 | 2-{5-[3-chloro-4-(methyloxy)phenyl]-3-pyridin-4-yl-1H-1,2,4-triazol-1-yl}-N-cyclopentylacetamide |
| 4 | ethyl {3-[3-chloro-4-(methyloxy)phenyl]-5-pyridin-4-yl-1H-1,2,4-triazol-1-yl}acetate |
| 5 | 2-{3-[3-chloro-4-(methyloxy)phenyl]-5-pyridin-4-yl-1H-1,2,4-triazol-1-yl}-N-cyclopentylacetamide |
| 6 | methyl 3-{5-[3-chloro-4-(methyloxy)phenyl]-3-pyridin-4-yl-1H-1,2,4-triazol-1-yl}propanoate |
| 7 | methyl 3-{3-[3-chloro-4-(methyloxy)phenyl]-5-pyridin-4-yl-1H-1,2,4-triazol-1-yl}propanoate |
| 8 | N-(3-{5-[3-chloro-4-(methyloxy)phenyl]-3-pyridin-4-yl-1H-1,2,4-triazol-1-yl}propyl)-N-cyclopentyl-2-naphthalen-1-ylacetamide |
| 9 | N-(3-{3-[3-chloro-4-(methyloxy)phenyl]-5-pyridin-4-yl-1H-1,2,4-triazol-1-yl}propyl)-N-cyclopentyl-2-naphthalen-1-ylacetamide |
| 10 | N-(2-{5-[3-chloro-4-(methyloxy)phenyl]-3-pyridin-4-yl-1H-1,2,4-triazol-1-yl}ethyl)-N-cyclopentyl-2-naphthalen-1-ylacetamide |
| 11 | N-{2-[3-(3-chloro-4-hydroxyphenyl)-5-pyridin-4-yl-1H-1,2,4-triazol-1-yl]ethyl}-N-cyclopentyl-2-naphthalen-1-ylacetamide |
| 12 | 2-{3-[3-chloro-4-(methyloxy)phenyl]-5-pyridin-3-yl-1H-1,2,4-triazol-1-yl}-N-cyclopentylacetamide |
| 13 | N-(2-{5-[3-chloro-4-(methyloxy)phenyl]-3-pyridin-3-yl-1H-1,2,4-triazol-1-yl}ethyl)-N-cyclopentyl-2-naphthalen-1-ylacetamide |
| 14 | ethyl [5-(4-nitrophenyl)-3-pyridin-4-yl-1H-1,2,4-triazol-1-yl]acetate |
| 15 | ethyl [5-(3,5-dichlorophenyl)-3-pyridin-4-yl-1H-1,2,4-triazol-1-yl]acetate |
| 16 | ethyl [3-(3,5-dichlorophenyl)-5-pyridin-4-yl-1H-1,2,4-triazol-1-yl]acetate |
| 17 | N-cyclopentyl-N-[2-(5-furan-2-yl-3-pyridin-4-yl-1H-1,2,4-triazol-1-yl)ethyl]-2-naphthalen-1-ylacetamide |
| 18 | N-cyclopentyl-N-[2-(3-furan-2-yl-5-pyridin-4-yl-1H-1,2,4-triazol-1-yl)ethyl]-2-naphthalen-1-ylacetamide |
| 19 | N-cyclopentyl-2-naphthalen-1-yl-N-{2-[5-pyridin-4-yl-3-(2-thienyl)-1H-1,2,4-triazol-1-yl]ethyl}acetamide |
| 20 | N-(2-{5-[3-chloro-4-(methyloxy)phenyl]-3-pyridin-4-yl-1H-1,2,4-triazol-1-yl}ethyl)-N-cyclopentylnaphthalene-1-carboxamide |
| 21 | N-(2-{5-[3-chloro-4-(methyloxy)phenyl]-3-pyridin-4-yl-1H-1,2,4-triazol-1-yl}ethyl)-N-cyclopentylnaphthalene-2-carboxamide |
| 22 | N-cyclopentyl-N-(2-{5-[3-(methyloxy)phenyl]-3-pyridin-4-yl-1H-1,2,4-triazol-1-yl}ethyl)-2-naphthalen-1-ylacetamide |
| 23 | N-cyclopentyl-N-(2-{3-[3-(methyloxy)phenyl]-5-pyridin-4-yl-1H-1,2,4-triazol-1-yl}ethyl)-2-naphthalen-1-ylacetamide |
| 24 | N-(4-{5-[3-chloro-4-(methyloxy)phenyl]-3-pyridin-4-yl-1H-1,2,4-triazol-1-yl}butyl)-N-cyclopentyl-2-naphthalen-1-ylacetamide |
| 25 | N-(4-{3-[3-chloro-4-(methyloxy)phenyl]-5-pyridin-4-yl-1H-1,2,4-triazol-1-yl}butyl)-N-cyclopentyl-2-naphthalen-1-ylacetamide |
| 26 | N-(2-{5-[3-chloro-4-(methyloxy)phenyl]-3-pyridin-4-yl-1H-1,2,4-triazol-1-yl}ethyl)-N-cyclopentylbenzamide |
| 27 | N-(2-{3-[3-chloro-4-(methyloxy)phenyl]-5-pyridin-4-yl-1H-1,2,4-triazol-1-yl}ethyl)-N-cyclopentylbenzamide |
| 28 | N-(2-{5-[3-chloro-4-(methyloxy)phenyl]-3-pyridin-4-yl-1H-1,2,4-triazol-1-yl}ethyl)-N-cyclopentylquinoline-4-carboxamide |
| 29 | N-(2-{5-[3-chloro-4-(methyloxy)phenyl]-3-pyridin-4-yl-1H-1,2,4-triazol-1-yl}ethyl)-N-cyclopentyl-N'-naphthalen-1-ylurea |
| 30 | N-(2-{5-[3-chloro-4-(methyloxy)phenyl]-3-pyridin-4-yl-1H-1,2,4-triazol-1-yl}ethyl)-N-cyclopentyl-N'-phenylurea |
| 31 | N-(2-{5-[3-chloro-4-(methyloxy)phenyl]-3-pyridin-4-yl-1H-1,2,4-triazol-1-yl}ethyl)-N-cyclopentyl-2-phenylacetamide |
| 32 | N-(2-{5-[3-chloro-4-(methyloxy)phenyl]-3-phenyl-1H-1,2,4-triazol-1-yl}ethyl)-N-cyclopentyl-2-naphthalen-1-ylacetamide |
| 33 | 2-{5-[3-chloro-4-(methyloxy)phenyl]-3-phenyl-1H-1,2,4-triazol-1-yl}-N-cyclopentylacetamide |
| 34 | N-(2-{5-[3-chloro-4-(methyloxy)phenyl]-3-pyridin-4-yl-1H-1,2,4-triazol-1-yl}ethyl)-2-naphthalen-1-ylacetamide |
| 35 | N-(2-{3-[3-chloro-4-(methyloxy)phenyl]-5-pyridin-4-yl-1H-1,2,4-triazol-1-yl}ethyl)-N-(1-methylethyl)-2-naphthalen-1-ylacetamide |
| 36 | N-(2-{5-[3-chloro-4-(methyloxy)phenyl]-3-pyridin-4-yl-1H-1,2,4-triazol-1-yl}ethyl)-N-cyclohexyl-2-naphthalen-1-ylacetamide |
| 37 | N-(2-{3-[3-chloro-4-(methyloxy)phenyl]-5-pyridin-4-yl-1H-1,2,4-triazol-1-yl}ethyl)-N-cyclohexyl-2-naphthalen-1-ylacetamide |
| 38 | N-(2-{3-[3-chloro-4-(methyloxy)phenyl]-5-pyridin-4-yl-1H-1,2,4-triazol-1-yl}ethyl)-N-cyclopropyl-2-naphthalen-1-ylacetamide |
| 39 | N-cyclopentyl-N-(2-{5-[4-(methyloxy)phenyl]-3-pyridin-4-yl-1H-1,2,4-triazol-1-yl}ethyl)-2-naphthalen-1-ylacetamide |
| 40 | N-cyclopentyl-N-(2-{3-[4-(methyloxy)phenyl]-5-pyridin-4-yl-1H-1,2,4-triazol-1-yl}ethyl)-2-naphthalen-1-ylacetamide |

TABLE 1-continued

| Entry | Name |
|---|---|
| 41 | N-(2-{5-[3,4-bis(methyloxy)phenyl]-3-pyridin-4-yl-1H-1,2,4-triazol-1-yl}ethyl)-N-cyclopentyl-2-naphthalen-1-ylacetamide |
| 42 | N-(2-{3-[3,4-bis(methyloxy)phenyl]-5-pyridin-4-yl-1H-1,2,4-triazol-1-yl}ethyl)-N-cyclopentyl-2-naphthalen-1-ylacetamide |
| 43 | N-cyclopentyl-N-[2-(5-methyl-3-pyridin-4-yl-1H-1,2,4,-triazol-1-yl)ethyl]-2-naphthalen-1-ylacetamide |
| 44 | N-cyclopentyl-2-naphthalen-1-yl-N-[2-(3-pyridin-4-yl-1H-1,2,4-triazol-1-yl)ethyl]acetamide |
| 45 | N-cyclopentyl-2-naphthalen-1-yl-N-(2-{3-pyridin-4-yl-5-[3-(trifluoromethyl)phenyl]-1H-1,2,4-triazol-1-yl}ethyl)acetamide |
| 46 | N-cyclopentyl-2-naphthalen-1-yl-N-(2-{5-pyridin-4-yl-3-[3-(trifluoromethyl)phenyl]-1H-1,2,4-triazol-1-yl}ethyl)acetamide |
| 47 | N-cyclopentyl-N-{2-[5-(3,5-dichlorophenyl)-3-pyridin-4-yl-1H-1,2,4-triazol-1-yl]ethyl}-2-naphthalen-1-ylacetamide |
| 48 | N-(2-{5-[3-chloro-4-(methyloxy)phenyl]-3-pyridin-4-yl-1H-1,2,4-triazol-1-yl}ethyl)-N-cyclopentyl-2-naphthalen-2-ylacetamide |
| 49 | N-cyclopentyl-2-naphthalen-1-yl-N-[2-(5-pyridin-4-yl-1H-1,2,4-triazol-3-yl)ethyl]acetamide |
| 50 | N-cyclopentyl-2-naphthalen-1-yl-N-[2-(5-phenyl-3-pyridin-4-yl-1H-1,2,4-triazol-1-yl)ethyl]acetamide |
| 51 | N-cyclopentyl-2-naphthalen-1-yl-N-[2-(3-phenyl-5-pyridin-4-yl-1H-1,2,4-triazol-1-yl)ethyl]acetamide |
| 52 | N-cyclopentyl-2-naphthalen-1-yl-N-[2-(3-pyridin-4-yl-1,2,4-oxadiazol-5-yl)ethyl]acetamide |
| 53 | N-{2-[5-[3-chloro-4-(methyloxy)phenyl]-3-(2-chloropyridin-4-yl)-1H-1,2,4-triazol-1-yl]ethyl}-N-cyclopentyl-2-naphthalen-1-ylacetamide |
| 54 | N-cyclopentyl-N-(2-{4-[4-(methyloxy)phenyl]-2-pyridin-4-yl-1H-imidazol-5-yl}ethyl)-2-naphthalen-1-ylacetamide |
| 55 | N-(2-{3-[3-chloro-4-(methyloxy)phenyl]-5-pyridin-4-yl-1H-1,2,4-triazol-1-yl}ethyl)-N-cyclopentyl-N'-naphthalen-1-ylurea |
| 56 | N-cyclopentyl-N-{2-[5-(3-fluorophenyl)-3-pyridin-4-yl-1H-1,2,4-triazol-1-yl]ethyl}-2-naphthalen-1-ylacetamide |
| 57 | N-cyclopentyl-N-{2-[3-(3-fluorophenyl)-5-pyridin-4-yl-1H-1,2,4-triazol-1-yl]ethyl}-2-naphthalen-1-ylacetamide |
| 58 | N-{2-[5-(3-chlorophenyl)-3-pyridin-4-yl-1H-1,2,4-triazol-1-yl]ethyl}-N-cyclopentyl-2-naphthalen-1-ylacetamide |
| 59 | N-{2-[3-(3-chlorophenyl)-5-pyridin-4-yl-1H-1,2,4-triazol-1-yl]ethyl}-N-cyclopentyl-2-naphthalen-1-ylacetamide |
| 60 | N-cyclopentyl-2-naphthalen-1-yl-N-[2-(5-piperidin-4-yl-3-pyridin-4-yl-1H-1,2,4-triazol-1-yl)ethyl]acetamide |
| 61 | N-{2-[5-(2-chlorophenyl)-3-pyridin-4-yl-1H-1,2,4-triazol-1-yl]ethyl}-N-cyclopentyl-2-naphthalen-1-ylacetamide |
| 62 | N-{2-[3-(2-chlorophenyl)-5-pyridin-4-yl-1H-1,2,4-triazol-1-yl]ethyl}-N-cyclopentyl-2-naphthalen-1-ylacetamide |
| 63 | N-{2-[5-(1,3-benzodioxol-5-yl)-3-pyridin-4-yl-1H-1,2,4-triazol-1-yl]ethyl}-N-cyclopentyl-2-naphthalen-1-ylacetamide |
| 64 | N-{2-[3-(1,3-benzodioxol-5-yl)-5-pyridin-4-yl-1H-1,2,4-triazol-1-yl]ethyl}-N-cyclopentyl-2-naphthalen-1-ylacetamide |
| 65 | N-{2-[5-(3-bromophenyl)-3-pyridin-4-yl-1H-1,2,4-triazol-1-yl]ethyl}-N-cyclopentyl-2-naphthalen-1-ylacetamide |
| 66 | N-{2-[3-(3-bromophenyl)-5-pyridin-4-yl-1H-1,2,4-triazol-1-yl]ethyl}-N-cyclopentyl-2-naphthalen-1-ylacetamide |
| 67 | N-{2-[5-(4-bromophenyl)-3-pyridin-4-yl-1H-1,2,4-triazol-1-yl]ethyl}-N-cyclopentyl-2-naphthalen-1-ylacetamide |
| 68 | N-{2-[3-(4-bromophenyl)-5-pyridin-4-yl-1H-1,2,4-triazol-1-yl]ethyl}-N-cyclopentyl-2-naphthalen-1-ylacetamide |
| 69 | N-cyclopentyl-N-[2-(5-methyl-3-pyridazin-4-yl-1H-1,2,4-triazol-1-yl)ethyl]-2-naphthalen-1-ylacetamide |
| 70 | N-cyclopentyl-N-{2-[5-(4-methylphenyl)-3-pyridin-4-yl-1H-1,2,4-triazol-1-yl]ethyl}-2-naphthalen-1-ylacetamide |
| 71 | N-cyclopentyl-N-{2-[3-(4-methylphenyl)-5-pyridin-4-yl-1H-1,2,4-triazol-1-yl]ethyl}-2-naphthalen-1-ylacetamide |
| 72 | N-cyclopentyl-N-{2-[5-(3-methylphenyl)-3-pyridin-4-yl-1H-1,2,4-triazol-1-yl]ethyl}-2-naphthalen-1-ylacetamide |
| 73 | N-cyclopentyl-N-{2-[3-(3-methylphenyl)-5-pyridin-4-yl-1H-1,2,4-triazol-1-yl]ethyl}-2-naphthalen-1-ylacetamide |
| 74 | N-cyclopentyl-N-{2-[5-(2,4-dichlorophenyl)-3-pyridin-4-yl-1H-1,2,4-triazol-1-yl]ethyl}-2-naphthalen-1-ylacetamide |
| 75 | N-cyclopentyl-N-{2-[3-(2,4-dichlorophenyl)-5-pyridin-4-yl-1H-1,2,4-triazol-1-yl]ethyl}-2-naphthalen-1-ylacetamide |
| 76 | N-cyclopentyl-2-naphthalen-1-yl-N-(2-{3-pyridin-4-yl-5-[4-(trifluoromethyl)phenyl]-1H-1,2,4-triazol-1-yl}ethyl)acetamide |
| 77 | N-cyclopentyl-2-naphthalen-1-yl-N-(2-{5-pyridin-4-yl-3-[4-(trifluoromethyl)phenyl]-1H-1,2,4-triazol-1-yl}ethyl)acetamide |
| 78 | N-(2-{5-[3-chloro-4-(methyloxy)phenyl]-3-pyridin-4-yl-1H-1,2,4-triazol-1-yl}ethyl)-N-cyclopropyl-2-naphthalen-1-ylacetamide |
| 79 | N-(2-{5-[3-chloro-4-(methyloxy)phenyl]-3-pyridin-4-yl-1H-1,2,4-triazol-1-yl}ethyl)-N-(1-methylethyl)-2-naphthalen-1-ylacetamide |

TABLE 1-continued

| Entry | Name |
|---|---|
| 80 | N-cyclopentyl-N-[2-(5-ethyl-3-pyridin-4-yl-1H-1,2,4-triazol-1-yl)ethyl]-2-naphthalen-1-ylacetamide |
| 81 | N-(2-{5-[3-chloro-4-(methyloxy)phenyl]-3-pyridin-4-yl-1H-1,2,4-triazol-1-yl}ethyl)-N-(1-methylpiperidin-4-yl)-2-naphthalen-1-ylacetamide |
| 82 | N-(2-{5-[3-chloro-4-(methyloxy)phenyl]-3-pyridin-4-yl-1H-1,2,4-triazol-1-yl}ethyl)-N-cyclopentyl-N'-[(1R,2S)-2-phenylcyclopropyl]urea |
| 83 | N-(2-{5-[3-chloro-4-(methyloxy)phenyl]-3-pyridin-4-yl-1H-1,2,4-triazol-1-yl}ethyl)-N-cyclopentyl-N'-(2,4-dichlorophenyl)urea |
| 84 | N-(2-{5-[3-chloro-4-(methyloxy)phenyl]-3-pyridin-4-yl-1H-1,2,4-triazol-1-yl}ethyl)-N-cyclopentyl-N'-[2-(methyloxy)phenyl]urea |
| 85 | N'-[2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 86 | N-(2-{5-[3-chloro-4-(methyloxy)phenyl]-3-pyridin-4-yl-1H-1,2,4-triazol-1-yl}ethyl)-N-cyclopentyl-N'-(2-methylphenyl)urea |
| 87 | N-(2-{5-[3-chloro-4-(methyloxy)phenyl]-3-pyridin-4-yl-1H-1,2,4-triazol-1-yl}ethyl)-N-cyclopentyl-N'-(2-ethylphenyl)urea |
| 88 | N-(2-{5-[3-chloro-4-(methyloxy)phenyl]-3-pyridin-4-yl-1H-1,2,4-triazol-1-yl}ethyl)-N-cyclopentyl-N'-(3,4-dichlorophenyl)urea |
| 89 | N-(2-{5-[3-chloro-4-(methyloxy)phenyl]-3-pyridin-4-yl-1H-1,2,4-triazol-1-yl}ethyl)-N-cyclopentyl-N'-hexylurea |
| 90 | N-(2-{5-[3-chloro-4-(methyloxy)phenyl]-3-pyridin-4-yl-1H-1,2,4-triazol-1-yl}ethyl)-N-cyclopentyl-N'-(4-fluorophenyl)urea |
| 91 | N-(2-{5-[3-chloro-4-(methyloxy)phenyl]-3-pyridin-4-yl-1H-1,2,4-triazol-1-yl}ethyl)-N-cyclopentyl-N'-[4-(methyloxy)phenyl]urea |
| 92 | N-(2-{5-[3-chloro-4-(methyloxy)phenyl]-3-pyridin-4-yl-1H-1,2,4-triazol-1-yl}ethyl)-N-cyclopentyl-N'-(phenylmethyl)urea |
| 93 | N'-[3,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylurea |
| 94 | N-(2-{5-[3-chloro-4-(methyloxy)phenyl]-3-pyridin-4-yl-1H-1,2,4-triazol-1-yl}ethyl)-N-cyclopentyl-N'-[3,4,5-tris(methyloxy)phenyl]urea |
| 95 | N'-(3-acetylphenyl)-N-(2-{5-[3-chloro-4-(methyloxy)phenyl]-3-pyridin-4-yl-1H-1,2,4-triazol-1-yl}ethyl)-N-cyclopentylurea |
| 96 | N-(2-{5-[3-chloro-4-(methyloxy)phenyl]-3-pyridin-4-yl-1H-1,2,4-triazol-1-yl}ethyl)-N-cyclopentyl-N'-(3,4-dimethylphenyl)urea |
| 97 | N-(2-{5-[3-chloro-4-(methyloxy)phenyl]-3-pyridin-4-yl-1H-1,2,4-triazol-1-yl}ethyl)-N'-[4-chloro-2-(trifluoromethyl)phenyl]-N-cyclopentylurea |
| 98 | N-(2-{5-[3-chloro-4-(methyloxy)phenyl]-3-pyridin-4-yl-1H-1,2,4-triazol-1-yl}ethyl)-N-cyclopentyl-N'-[4-(methylthio)phenyl]urea |
| 99 | N'-(4-acetylphenyl)-N-(2-{5-[3-chloro-4-(methyloxy)phenyl]-3-pyridin-4-yl-1H-1,2,4-triazol-1-yl}ethyl)-N-cyclopentylurea |
| 100 | N-(2-{5-[3-chloro-4-(methyloxy)phenyl]-3-pyridin-4-yl-1H-1,2,4-triazol-1-yl}ethyl)-N-cyclopentyl-N'-[4-(1-methylethyl)phenyl]urea |
| 101 | N-(2-{5-[3-chloro-4-(methyloxy)phenyl]-3-pyridin-4-yl-1H-1,2,4-triazol-1-yl}ethyl)-N'-(4-cyanophenyl)-N-cyclopentylurea |
| 102 | N'-biphenyl-2-yl-N-(2-{5-[3-chloro-4-(methyloxy)phenyl]-3-pyridin-4-yl-1H-1,2,4-triazol-1-yl}ethyl)-N-cyclopentylurea |
| 103 | N-(2-{5-[3-chloro-4-(methyloxy)phenyl]-3-pyridin-4-yl-1H-1,2,4-triazol-1-yl}ethyl)-N-cyclopentyl-N'-pentylurea |
| 104 | N-(2-{5-[3-chloro-4-(methyloxy)phenyl]-3-pyridin-4-yl-1H-1,2,4-triazol-1-yl}ethyl)-N-cyclopentyl-N'-heptylurea |
| 105 | N-(2-{5-[3-chloro-4-(methyloxy)phenyl]-3-pyridin-4-yl-1H-1,2,4-triazol-1-yl}ethyl)-N'-(3-chlorophenyl)-N-cyclopentylurea |
| 106 | N-(2-{5-[3-chloro-4-(methyloxy)phenyl]-3-pyridin-4-yl-1H-1,2,4-triazol-1-yl}ethyl)-N-cyclopentyl-N'-(3-methylphenyl)urea |
| 107 | N-(2-{5-[3-chloro-4-(methyloxy)phenyl]-3-pyridin-4-yl-1H-1,2,4-triazol-1-yl}ethyl)-N-cyclopentyl-N'-(1,1-dimethylethyl)urea |
| 108 | N-(2-{5-[3-chloro-4-(methyloxy)phenyl]-3-pyridin-4-yl-1H-1,2,4-triazol-1-yl}ethyl)-N-cyclopentyl-N'-(1-methylethyl)urea |
| 109 | N-(2-{5-[3-chloro-4-(methyloxy)phenyl]-3-pyridin-4-yl-1H-1,2,4-triazol-1-yl}ethyl)-N-cyclopentyl-N'-ethylurea |
| 110 | N-(2-{5-[3-chloro-4-(methyloxy)phenyl]-3-pyridin-4-yl-1H-1,2,4-triazol-1-yl}ethyl)-N-cyclopentyl-N'-propylurea |
| 111 | N-(2-{5-[3-chloro-4-(methyloxy)phenyl]-3-pyridin-4-yl-1H-1,2,4-triazol-1-yl}ethyl)-N-cyclopentyl-N'-[4-(ethyloxy)phenyl]urea |
| 112 | N-(2-{5-[3-chloro-4-(methyloxy)phenyl]-3-pyridin-4-yl-1H-1,2,4-triazol-1-yl}ethyl)-N-cyclopentyl-N'-(4-ethylphenyl)urea |
| 113 | N-(2-{5-[3-chloro-4-(methyloxy)phenyl]-3-pyridin-4-yl-1H-1,2,4-triazol-1-yl}ethyl)-N-cyclopentyl-N'-(2-phenylethyl)urea |
| 114 | N-(2-{5-[3-chloro-4-(methyloxy)phenyl]-3-pyridin-4-yl-1H-1,2,4-triazol-1-yl}ethyl)-N-cyclopentyl-N'-{1-methyl-1-[3-(1-methylethenyl)phenyl]ethyl}urea |
| 115 | N-(2-{5-[3-chloro-4-(methyloxy)phenyl]-3-pyridin-4-yl-1H-1,2,4-triazol-1-yl}ethyl)-N-cyclopentyl-N'-(2-fluorophenyl)urea |
| 116 | N-(2-{5-[3-chloro-4-(methyloxy)phenyl]-3-pyridin-4-yl-1H-1,2,4-triazol-1-yl}ethyl)-N-cyclopentyl-N'-(2,4-difluorophenyl)urea |
| 117 | N-(2-{5-[3-chloro-4-(methyloxy)phenyl]-3-pyridin-4-yl-1H-1,2,4-triazol-1-yl}ethyl)-N-cyclopentyl-N'-(2,6-difluorophenyl)urea |

TABLE 1-continued

| Entry | Name |
|---|---|
| 118 | N-(2-{5-[3-chloro-4-(methyloxy)phenyl]-3-pyridin-4-yl-1H-1,2,4-triazol-1-yl}ethyl)-N'-(2-chlorophenyl)-N-cyclopentylurea |
| 119 | N-(2-{5-[3-chloro-4-(methyloxy)phenyl]-3-pyridin-4-yl-1H-1,2,4-triazol-1-yl}ethyl)-N-cyclopentyl-N'-(2,3-dichlorophenyl)urea |
| 120 | N'-[2,5-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 121 | N-(2-{5-[3-chloro-4-(methyloxy)phenyl]-3-pyridin-4-yl-1H-1,2,4-triazol-1-yl}ethyl)-N-cyclopentyl-N'-[2-(ethyloxy)phenyl]urea |
| 122 | N-(2-{5-[3-chloro-4-(methyloxy)phenyl]-3-pyridin-4-yl-1H-1,2,4-triazol-1-yl}ethyl)-N-cyclopentyl-N'-[2-(trifluoromethyl)phenyl]urea |
| 123 | N-(2-{5-[3-chloro-4-(methyloxy)phenyl]-3-pyridin-4-yl-1H-1,2,4-triazol-1-yl}ethyl)-N-cyclopentyl-N'-(2,6-dimethylphenyl)urea |
| 124 | N-(2-{5-[3-chloro-4-(methyloxy)phenyl]-3-pyridin-4-yl-1H-1,2,4-triazol-1-yl}ethyl)-N-cyclopentyl-N'-[4-(trifluoromethyl)phenyl]urea |
| 125 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]urea |
| 126 | N-(2-{5-[3-chloro-4-(methyloxy)phenyl]-3-pyridin-4-yl-1H-1,2,4-triazol-1-yl}ethyl)-N-cyclopentyl-N'-(2,4,5-trichlorophenyl)urea |
| 127 | N-(2-{5-[3-chloro-4-(methyloxy)phenyl]-3-pyridin-4-yl-1H-1,2,4-triazol-1-yl}ethyl)-N-cyclopentyl-N'-(2,3-dimethylphenyl)urea |
| 128 | N-(2-{5-[3-chloro-4-(methyloxy)phenyl]-3-pyridin-4-yl-1H-1,2,4-triazol-1-yl}ethyl)-N-cyclopentyl-N'-(2,4-dimethylphenyl)urea |
| 129 | N-(2-{5-[3-chloro-4-(methyloxy)phenyl]-3-pyridin-4-yl-1H-1,2,4-triazol-1-yl}ethyl)-N'-(3-chloro-4-methylphenyl)-N-cyclopentylurea |
| 130 | N-(2-{5-[3-chloro-4-(methyloxy)phenyl]-3-pyridin-4-yl-1H-1,2,4-triazol-1-yl}ethyl)-N-cyclopentyl-N'-[2-(1,1-dimethylethyl)-6-methylphenyl]urea |
| 131 | N'-[4-(butyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 132 | N-(2-{5-[3-chloro-4-(methyloxy)phenyl]-3-pyridin-4-yl-1H-1,2,4-triazol-1-yl}ethyl)-N-cyclopentyl-N'-(2-methyl-3-nitrophenyl)urea |
| 133 | N-(2-{5-[3-chloro-4-(methyloxy)phenyl]-3-pyridin-4-yl-1H-1,2,4-triazol-1-yl}ethyl)-N-cyclopentyl-N'-(2,5-dichlorophenyl)urea |
| 134 | N-(2-{5-[3-chloro-4-(methyloxy)phenyl]-3-pyridin-4-yl-1H-1,2,4-triazol-1-yl}ethyl)-N-cyclopentyl-N'-(3-fluorophenyl)urea |
| 135 | N-(2-{5-[3-chloro-4-(methyloxy)phenyl]-3-pyridin-4-yl-1H-1,2,4-triazol-1-yl}ethyl)-N'-(4-chlorophenyl)-N-cyclopentylurea |
| 136 | N-(2-{5-[3-chloro-4-(methyloxy)phenyl]-3-pyridin-4-yl-1H-1,2,4-triazol-1-yl}ethyl)-N-cyclopentyl-N'-(4-methylphenyl)urea |
| 137 | N-(2-{5-[3-chloro-4-(methyloxy)phenyl]-3-pyridin-4-yl-1H-1,2,4-triazol-1-yl}ethyl)-N-cyclopentyl-N'-(2,4,6-trichlorophenyl)urea |
| 138 | N-(2-{5-[3-chloro-4-(methyloxy)phenyl]-3-pyridin-4-yl-1H-1,2,4-triazol-1-yl}ethyl)-N-cyclopentyl-N'-[2-methyl-4-(methyloxy)phenyl]urea |
| 139 | N-(2-{5-[3-chloro-4-(methyloxy)phenyl]-3-pyridin-4-yl-1H-1,2,4-triazol-1-yl}ethyl)-N-cyclopentyl-N'-(2,5-dimethylphenyl)urea |
| 140 | N'-[5-chloro-2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 141 | N-(2-{5-[3-chloro-4-(methyloxy)phenyl]-3-pyridin-4-yl-1H-1,2,4-triazol-1-yl}ethyl)-N-cyclopentyl-N'-(3,5-dichlorophenyl)urea |
| 142 | N'-[5-chloro-2-(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 143 | N-(2-{5-[3-chloro-4-(methyloxy)phenyl]-3-pyridin-4-yl-1H-1,2,4-triazol-1-yl}ethyl)-N-cyclopentyl-N'-[3-(methylthio)phenyl]urea |
| 144 | N-(2-{5-[3-chloro-4-(methyloxy)phenyl]-3-pyridin-4-yl-1H-1,2,4-triazol-1-yl}ethyl)-N-cyclopentyl-N'-(3,5-dimethylphenyl)urea |
| 145 | N-(2-{5-[3-chloro-4-(methyloxy)phenyl]-3-pyridin-4-yl-1H-1,2,4-triazol-1-yl}ethyl)-N-cyclopentyl-N'-[5-methyl-2-(methyloxy)phenyl]urea |
| 146 | N-(2-{5-[3-chloro-4-(methyloxy)phenyl]-3-pyridin-4-yl-1H-1,2,4-triazol-1-yl}ethyl)-N-cyclopentyl-N'-(4-iodophenyl)urea |
| 147 | N-(2-{5-[3-chloro-4-(methyloxy)phenyl]-3-pyridin-4-yl-1H-1,2,4-triazol-1-yl}ethyl)-N-cyclopentyl-N'-[4-(phenyloxy)phenyl]urea |
| 148 | N-(2-{5-[3-chloro-4-(methyloxy)phenyl]-3-pyridin-4-yl-1H-1,2,4-triazol-1-yl}ethyl)-N-cyclopentyl-N'-(2,4,6-trimethylphenyl)urea |
| 149 | N-(2-{5-[3-chloro-4-(methyloxy)phenyl]-3-pyridin-4-yl-1H-1,2,4-triazol-1-yl}ethyl)-N'-(5-chloro-2-methylphenyl)-N-cyclopentylurea |
| 150 | N-(2-{5-[3-chloro-4-(methyloxy)phenyl]-3-pyridin-4-yl-1H-1,2,4-triazol-1-yl}ethyl)-N'-(4-chloro-2-methylphenyl)-N-cyclopentylurea |
| 151 | N-(2-{5-[3-chloro-4-(methyloxy)phenyl]-3-pyridin-4-yl-1H-1,2,4-triazol-1-yl}ethyl)-N'-(2-chloro-6-methylphenyl)-N-cyclopentylurea |
| 152 | N-(2-{5-[3-chloro-4-(methyloxy)phenyl]-3-pyridin-4-yl-1H-1,2,4-triazol-1-yl}ethyl)-N'-(3-chloro-2-methylphenyl)-N-cyclopentylurea |
| 153 | N'-(3-chloro-4-fluorophenyl)-N-(2-{5-[3-chloro-4-(methyloxy)phenyl]-3-pyridin-4-yl-1H-1,2,4-triazol-1-yl}ethyl)-N-cyclopentylurea |
| 154 | N-(2-{5-[3-chloro-4-(methyloxy)phenyl]-3-pyridin-4-yl-1H-1,2,4-triazol-1-yl}ethyl)-N-cyclopentyl-N'-[2-(methylthio)phenyl]urea |
| 155 | N-(2-{5-[3-chloro-4-(methyloxy)phenyl]-3-pyridin-4-yl-1H-1,2,4-triazol-1-yl}ethyl)-N-cyclopentyl-N'-[3-(trifluoromethyl)phenyl]urea |

TABLE 1-continued

| Entry | Name |
|---|---|
| 156 | N-(2-{5-[3-chloro-4-(methyloxy)phenyl]-3-pyridin-4-yl-1H-1,2,4-triazol-1-yl}ethyl)-N-cyclopentyl-N'-prop-2-en-1-ylurea |
| 157 | N-(2-{5-[3-chloro-4-(methyloxy)phenyl]-3-pyridin-4-yl-1H-1,2,4-triazol-1-yl}ethyl)-N-cyclopentyl-N'-[2-(1-methylethyl)phenyl]urea |
| 158 | N-(2-{5-[3-chloro-4-(methyloxy)phenyl]-3-pyridin-4-yl-1H-1,2,4-triazol-1-yl}ethyl)-N-cyclopentyl-N'-(5-fluoro-2-methylphenyl)urea |
| 159 | N-(2-{5-[3-chloro-4-(methyloxy)phenyl]-3-pyridin-4-yl-1H-1,2,4-triazol-1-yl}ethyl)-N-cyclopentyl-N'-(3,4-difluorophenyl)urea |
| 160 | N-[2-(5-methyl-3-pyridin-4-yl-1H-1,2,4-triazol-1-yl)ethyl]-N-(2-morpholin-4-ylethyl)-2-naphthalen-1-ylacetamide |
| 161 | N-cyclopentyl-N-(2-{5-methyl-3-[2-(methylamino)pyrimidin-4-yl]-1H-1,2,4-triazol-1-yl}ethyl)-2-naphthalen-1-ylacetamide |
| 162 | N-{2-[3-(2,1,3-benzothiadiazol-5-yl)-5-methyl-1H-1,2,4-triazol-1-yl]ethyl}-N-cyclopentyl-2-naphthalen-1-ylacetamide |
| 163 | N-cyclopentyl-N-{2-[5-methyl-3-(2-morpholin-4-ylpyridin-4-yl)-1H-1,2,4-triazol-1-yl]ethyl}-2-naphthalen-1-ylacetamide |
| 164 | N-cyclopentyl-N-{2-[3-(2-{[2-(dimethylamino)ethyl]amino}pyridin-4-yl)-5-methyl-1H-1,2,4-triazol-1-yl]ethyl}-2-naphthalen-1-ylacetamide |
| 165 | N-cyclopentyl-N-(2-{5-methyl-3-[2-(phenylamino)pyridin-4-yl]-1H-1,2,4-triazol-1-yl}ethyl)-2-naphthalen-1-ylacetamide |
| 166 | N-cyclopentyl-N-(2-{3-[2-(ethylamino)pyridin-4-yl]-5-methyl-1H-1,2,4-triazol-1-yl}ethyl)-2-naphthalen-1-ylacetamide |
| 167 | N-cyclopentyl-N-(2-{5-methyl-3-[2-(methylamino)pyridin-4-yl]-1H-1,2,4-triazol-1-yl}ethyl)-2-naphthalen-1-ylacetamide |
| 168 | N-cyclopropyl-N-[2-(5-methyl-3-pyridin-4-yl-1H-1,2,4-triazol-1-yl)ethyl]-2-naphthalen-1-ylacetamide |
| 169 | N-[2-(5-methyl-3-pyridin-4-yl-1H-1,2,4-triazol-1-yl)ethyl]-2-naphthalen-1-yl-N-(2-pyrrolidin-1-ylethyl)acetamide |
| 170 | N-[2-(dimethylamino)ethyl]-N-[2-(5-methyl-3-pyridin-4-yl-1H-1,2,4-triazol-1-yl)ethyl]-2-naphthalen-1-ylacetamide |
| 171 | N-[2-(5-methyl-3-pyridin-4-yl-1H-1,2,4-triazol-1-yl)ethyl]-2-naphthalen-1-yl-N-(tetrahydro-2H-pyran-4-yl)acetamide |
| 172 | N-cyclopentyl-N-[2-(5-methyl-3-{2-[(phenylmethyl)amino]pyridin-4-yl}-1H-1,2,4-triazol-1-yl)ethyl]-2-naphthalen-1-ylacetamide |
| 173 | N-(2-{3-[2-(butylamino)pyridin-4-yl]-5-methyl-1H-1,2,4-triazol-1-yl}ethyl)-N-cyclopentyl-2-naphthalen-1-ylacetamide |
| 174 | N-cyclopentyl-N-[2-(5-methyl-3-{2-[(2-morpholin-4-ylethyl)amino]pyridin-4-yl}-1H-1,2,4-triazol-1-yl)ethyl]-2-naphthalen-1-ylacetamide |
| 175 | N-cyclopentyl-N-{2-[5-methyl-3-(2-{[2-(methyloxy)ethyl]amino}pyridin-4-yl)-1H-1,2,4-triazol-1-yl]ethyl}-2-naphthalen-1-ylacetamide |
| 176 | N-{2-[3-(2-aminopyridin-4-yl)-5-methyl-1H-1,2,4-triazol-1-yl]ethyl}-N-cyclopentyl-2-naphthalen-1-ylacetamide |
| 177 | N-(1-methylethyl)-N-[2-(5-methyl-3-pyridin-4-yl-1H-1,2,4-triazol-1-yl)ethyl]-2-naphthalen-1-ylacetamide |
| 178 | N-[2-(5-methyl-3-pyridin-4-yl-1H-1,2,4-triazol-1-yl)ethyl]-2-naphthalen-1-yl-N-(2-piperidin-1-ylethyl)acetamide |
| 179 | N-cyclohexyl-N-[2-(5-methyl-3-pyridin-4-yl-1H-1,2,4-triazol-1-yl)ethyl]-2-naphthalen-1-ylacetamide |
| 180 | N-[2-(5-methyl-3-pyridin-4-yl-1H-1,2,4-triazol-1-yl)ethyl]-2-naphthalen-1-yl-N-(tetrahydrofuran-2-ylmethyl)acetamide |
| 181 | N-cyclopentyl-N-(2-{5-methyl-3-[2-(piperidin-3-ylamino)pyridin-4-yl]-1H-1,2,4-triazol-1-yl}ethyl)-2-naphthalen-1-ylacetamide |
| 182 | N-cyclopentyl-N-[2-(5-methyl-3-{2-[(3R)-pyrrolidin-3-ylamino]pyridin-4-yl}-1H-1,2,4-triazol-1-yl)ethyl]-2-naphthalen-1-ylacetamide |
| 183 | N-cyclopentyl-N-[2-(5-methyl-3-{2-[(2-piperidin-1-ylethyl)amino]pyrimidin-4-yl}-1H-1,2,4-triazol-1-yl)ethyl]-2-naphthalen-1-ylacetamide |
| 184 | N-cyclopentyl-N-[2-(5-methyl-3-{2-[(phenylmethyl)amino]pyrimidin-4-yl}-1H-1,2,4-triazol-1-yl)ethyl]-2-naphthalen-1-ylacetamide |
| 185 | N-{2-[3-(2-amino-6-chloropyridin-4-yl)-5-methyl-1H-1,2,4-triazol-1-yl]ethyl}-N-cyclopentyl-2-naphthalen-1-ylacetamide |
| 186 | N-cyclopentyl-N-{2-[3-(2,6-diaminopyridin-4-yl)-5-methyl-1H-1,2,4-triazol-1-yl]ethyl}-2-naphthalen-1-ylacetamide |
| 187 | N-(2-{3-[2-amino-6-(ethyloxy)pyridin-4-yl]-5-methyl-1H-1,2,4-triazol-1-yl}ethyl)-N-cyclopentyl-2-naphthalen-1-ylacetamide |
| 188 | N-(2-{5-[3-chloro-4-(methyloxy)phenyl]-3-pyridin-4-yl-1H-1,2,4-triazol-1-yl}ethyl)-N-cyclopentyl-1-phenylcyclopropanecarboxamide |
| 189 | N-(2-{5-[3-chloro-4-(methyloxy)phenyl]-3-pyridin-4-yl-1H-1,2,4-triazol-1-yl}ethyl)-1-(4-chlorophenyl)-N-cyclopentylcyclopropanecarboxamide |
| 190 | N-(2-{5-[3-chloro-4-(methyloxy)phenyl]-3-pyridin-4-yl-1H-1,2,4-triazol-1-yl}ethyl)-N-cyclopentyl-2-methylcyclopropanecarboxamide |
| 191 | N-(2-{5-[3-chloro-4-(methyloxy)phenyl]-3-pyridin-4-yl-1H-1,2,4-triazol-1-yl}ethyl)-N-cyclopentyl-1-phenylcyclopentanecarboxamide |
| 192 | 4-chloro-N-(2-{5-[3-chloro-4-(methyloxy)phenyl]-3-pyridin-4-yl-1H-1,2,4-triazol-1-yl}ethyl)-N-cyclopentyl-2-(methyloxy)benzamide |
| 193 | N-(2-{5-[3-chloro-4-(methyloxy)phenyl]-3-pyridin-4-yl-1H-1,2,4-triazol-1-yl}ethyl)-N-cyclopentyl-3-phenylbutanamide |
| 194 | N-(2-{5-[3-chloro-4-(methyloxy)phenyl]-3-pyridin-4-yl-1H-1,2,4-triazol-1-yl}ethyl)-N-cyclopentyl-3,7-dimethyloct-6-enamide |

TABLE 1-continued

| Entry | Name |
|---|---|
| 195 | N-(2-{5-[3-chloro-4-(methyloxy)phenyl]-3-pyridin-4-yl-1H-1,2,4-triazol-1-yl}ethyl)-N-cyclopentyl-3-(phenyloxy)propanamide |
| 196 | (3E)-N-(2-{5-[3-chloro-4-(methyloxy)phenyl]-3-pyridin-4-yl-1H-1,2,4-triazol-1-yl}ethyl)-N-cyclopentylhex-3-enamide |
| 197 | N-(2-{5-[3-chloro-4-(methyloxy)phenyl]-3-pyridin-4-yl-1H-1,2,4-triazol-1-yl}ethyl)-N-cyclopentyl-4-oxopentanamide |
| 198 | N-(2-{5-[3-chloro-4-(methyloxy)phenyl]-3-pyridin-4-yl-1H-1,2,4-triazol-1-yl}ethyl)-N-cyclopentyl-4-(3-methyl-5-oxo-4,5-dihydro-1H-pyrazol-1-yl)benzamide |
| 199 | N~2~-acetyl-N-(2-{5-[3-chloro-4-(methyloxy)phenyl]-3-pyridin-4-yl-1H-1,2,4-triazol-1-yl}ethyl)-N-cyclopentylglycinamide |
| 200 | N-(2-{5-[3-chloro-4-(methyloxy)phenyl]-3-pyridin-4-yl-1H-1,2,4-triazol-1-yl}ethyl)-N-cyclopentyl-2-(ethyloxy)acetamide |
| 201 | N-(2-{5-[3-chloro-4-(methyloxy)phenyl]-3-pyridin-4-yl-1H-1,2,4-triazol-1-yl}ethyl)-N-cyclopentyl-2-[3-(trifluoromethyl)phenyl]acetamide |
| 202 | N-(2-{5-[3-chloro-4-(methyloxy)phenyl]-3-pyridin-4-yl-1H-1,2,4-triazol-1-yl}ethyl)-N-cyclopentyl-5-oxo-L-prolinamide |
| 203 | N-(2-{5-[3-chloro-4-(methyloxy)phenyl]-3-pyridin-4-yl-1H-1,2,4-triazol-1-yl}ethyl)-N-cyclopentyl-3-furan-2-ylpropanamide |
| 204 | N-(2-{5-[3-chloro-4-(methyloxy)phenyl]-3-pyridin-4-yl-1H-1,2,4-triazol-1-yl}ethyl)-N-cyclopentyl-3-methylthiophene-2-carboxamide |
| 205 | N-(2-{5-[3-chloro-4-(methyloxy)phenyl]-3-pyridin-4-yl-1H-1,2,4-triazol-1-yl}ethyl)-N-cyclopentyl-1H-indole-3-carboxamide |
| 206 | N-(2-{5-[3-chloro-4-(methyloxy)phenyl]-3-pyridin-4-yl-1H-1,2,4-triazol-1-yl}ethyl)-N-cyclopentylpyrazine-2-carboxamide |
| 207 | N-(2-{5-[3-chloro-4-(methyloxy)phenyl]-3-pyridin-4-yl-1H-1,2,4-triazol-1-yl}ethyl)-N-cyclopentylpyridine-2-carboxamide |
| 208 | N-(2-{5-[3-chloro-4-(methyloxy)phenyl]-3-pyridin-4-yl-1H-1,2,4-triazol-1-yl}ethyl)-N-cyclopentyl-3-(phenylsulfonyl)propanamide |
| 209 | N-(2-{5-[3-chloro-4-(methyloxy)phenyl]-3-pyridin-4-yl-1H-1,2,4-triazol-1-yl}ethyl)-N-cyclopentyl-1H-benzimidazole-5-carboxamide |
| 210 | N-(2-{5-[3-chloro-4-(methyloxy)phenyl]-3-pyridin-4-yl-1H-1,2,4-triazol-1-yl}ethyl)-N-cyclopentyl-4-(methyloxy)quinoline-2-carboxamide |
| 211 | N-(2-{5-[3-chloro-4-(methyloxy)phenyl]-3-pyridin-4-yl-1H-1,2,4-triazol-1-yl}ethyl)-N-cyclopentyl-2-methylpyridine-3-carboxamide |
| 212 | N-(2-{5-[3-chloro-4-(methyloxy)phenyl]-3-pyridin-4-yl-1H-1,2,4-triazol-1-yl}ethyl)-N-cyclopentyl-2-{[2-(methyloxy)phenyl]oxy}acetamide |
| 213 | N-(2-{5-[3-chloro-4-(methyloxy)phenyl]-3-pyridin-4-yl-1H-1,2,4-triazol-1-yl}ethyl)-N-cyclopentyl-2-[(2-methylphenyl)oxy]acetamide |
| 214 | N-(2-{5-[3-chloro-4-(methyloxy)phenyl]-3-pyridin-4-yl-1H-1,2,4-triazol-1-yl}ethyl)-N-cyclopentyl-2-[(2,5-dimethylphenyl)oxy]acetamide |
| 215 | N-(2-{5-[3-chloro-4-(methyloxy)phenyl]-3-pyridin-4-yl-1H-1,2,4-triazol-1-yl}ethyl)-N-cyclopentyl-2-[(4-ethylphenyl)oxy]acetamide |
| 216 | N-(2-{5-[3-chloro-4-(methyloxy)phenyl]-3-pyridin-4-yl-1H-1,2,4-triazol-1-yl}ethyl)-N-cyclopentyl-2-({4-[(phenylmethyl)oxy]phenyl}oxy)acetamide |
| 217 | N-(2-{5-[3-chloro-4-(methyloxy)phenyl]-3-pyridin-4-yl-1H-1,2,4-triazol-1-yl}ethyl)-N-cyclopentyl-2-{[3-(methyloxy)phenyl]oxy}acetamide |
| 218 | N-(2-{5-[3-chloro-4-(methyloxy)phenyl]-3-pyridin-4-yl-1H-1,2,4-triazol-1-yl}ethyl)-N-cyclopentyl-2-(2,4,6-trimethylphenyl)acetamide |
| 219 | N-(2-{5-[3-chloro-4-(methyloxy)phenyl]-3-pyridin-4-yl-1H-1,2,4-triazol-1-yl}ethyl)-N-cyclopentyl-2-[(3,4-dimethylphenyl)oxy]acetamide |
| 220 | Nalpha-acetyl-N-(2-{5-[3-chloro-4-(methyloxy)phenyl]-3-pyridin-4-yl-1H-1,2,4-triazol-1-yl}ethyl)-N-cyclopentyl-3-fluorophenylalaninamide |
| 221 | Nalpha-acetyl-N-(2-{5-[3-chloro-4-(methyloxy)phenyl]-3-pyridin-4-yl-1H-1,2,4-triazol-1-yl}ethyl)-N-cyclopentyl-4-fluorophenylalaninamide |
| 222 | N-{2-[(2-{5-[3-chloro-4-(methyloxy)phenyl]-3-pyridin-4-yl-1H-1,2,4-triazol-1-yl}ethyl)(cyclopentyl)amino]-1-methyl-2-oxoethyl}benzamide |
| 223 | N-(2-{5-[3-chloro-4-(methyloxy)phenyl]-3-pyridin-4-yl-1H-1,2,4-triazol-1-yl}ethyl)-N-cyclopentyl-4-(4-methylphenyl)-4-oxobutanamide |
| 224 | 4-(acetylamino)-N-(2-{5-[3-chloro-4-(methyloxy)phenyl]-3-pyridin-4-yl-1H-1,2,4-triazol-1-yl}ethyl)-N-cyclopentylbutanamide |
| 225 | N-(2-{5-[3-chloro-4-(methyloxy)phenyl]-3-pyridin-4-yl-1H-1,2,4-triazol-1-yl}ethyl)-N-cyclopentyl-2,2-dimethylpentanamide |
| 226 | N-(2-{5-[3-chloro-4-(methyloxy)phenyl]-3-pyridin-4-yl-1H-1,2,4-triazol-1-yl}ethyl)-N-cyclopentyl-N'-phenylpentanediamide |
| 227 | N-(2-{5-[3-chloro-4-(methyloxy)phenyl]-3-pyridin-4-yl-1H-1,2,4-triazol-1-yl}ethyl)-N-cyclopentyltetrahydrofuran-2-carboxamide |
| 228 | N-(2-{5-[3-chloro-4-(methyloxy)phenyl]-3-pyridin-4-yl-1H-1,2,4-triazol-1-yl}ethyl)-N-cyclopentyl-2-(1,3-dimethyl-2,6-dioxo-1,2,3,6-tetrahydro-7H-purin-7-yl)acetamide |
| 229 | N-{2-[(2-{5-[3-chloro-4-(methyloxy)phenyl]-3-pyridin-4-yl-1H-1,2,4-triazol-1-yl}ethyl)(cyclopentyl)amino]-2-oxoethyl}furan-2-carboxamide |
| 230 | N~2~-acetyl-N~1~-(2-{5-[3-chloro-4-(methyloxy)phenyl]-3-pyridin-4-yl-1H-1,2,4-triazol-1-yl}ethyl)-N~1~-cyclopentyl-L-glutamamide |
| 231 | (4E)-N-(2-{5-[3-chloro-4-(methyloxy)phenyl]-3-pyridin-4-yl-1H-1,2,4-triazol-1-yl}ethyl)-N-cyclopentylhex-4-enamide |
| 232 | N-(2-{5-[3-chloro-4-(methyloxy)phenyl]-3-pyridin-4-yl-1H-1,2,4-triazol-1-yl}ethyl)-N-cyclopentyl-2-cyclopropylacetamide |

TABLE 1-continued

| Entry | Name |
|---|---|
| 233 | N-(2-{5-[3-chloro-4-(methyloxy)phenyl]-3-pyridin-4-yl-1H-1,2,4-triazol-1-yl}ethyl)-N-cyclopentyl-3-(methyloxy)propanamide |
| 234 | N-(2-{5-[3-chloro-4-(methyloxy)phenyl]-3-pyridin-4-yl-1H-1,2,4-triazol-1-yl}ethyl)-N-cyclopentyl-N',N'-dimethylbutanediamide |
| 235 | N-(2-{5-[3-chloro-4-(methyloxy)phenyl]-3-pyridin-4-yl-1H-1,2,4-triazol-1-yl}ethyl)-N-cyclopentyl-5-[(phenylmethyl)oxy]-1H-indole-2-carboxamide |
| 236 | N-(2-{5-[3-chloro-4-(methyloxy)phenyl]-3-pyridin-4-yl-1H-1,2,4-triazol-1-yl}ethyl)-N-cyclopentyl-2-(1H-pyrrol-1-yl)benzamide |
| 237 | 3-(2-chloro-6-fluorophenyl)-N-(2-{5-[3-chloro-4-(methyloxy)phenyl]-3-pyridin-4-yl-1H-1,2,4-triazol-1-yl}ethyl)-N-cyclopentyl-5-methylisoxazole-4-carboxamide |
| 238 | N-(2-{5-[3-chloro-4-(methyloxy)phenyl]-3-pyridin-4-yl-1H-1,2,4-triazol-1-yl}ethyl)-N-cyclopentyl-N'-[(1R)-1-phenylethyl]benzene-1,2-dicarboxamide |
| 239 | N-(2-{5-[3-chloro-4-(methyloxy)phenyl]-3-pyridin-4-yl-1H-1,2,4-triazol-1-yl}ethyl)-N-cyclopentyl-5-oxoprolinamide |
| 240 | N~2~-acetyl-N-(2-{5-[3-chloro-4-(methyloxy)phenyl]-3-pyridin-4-yl-1H-1,2,4-triazol-1-yl}ethyl)-N-cyclopentyl-L-leucinamide |
| 241 | N-(2-{5-[3-chloro-4-(methyloxy)phenyl]-3-pyridin-4-yl-1H-1,2,4-triazol-1-yl}ethyl)-N-cyclopentyl-1-(4-methylphenyl)cyclohexanecarboxamide |
| 242 | N~2~-acetyl-N~1~-(2-{5-[3-chloro-4-(methyloxy)phenyl]-3-pyridin-4-yl-1H-1,2,4-triazol-1-yl}ethyl)-N~1~-cyclopentyl-L-aspartamide |
| 243 | N-(2-{5-[3-chloro-4-(methyloxy)phenyl]-3-pyridin-4-yl-1H-1,2,4-triazol-1-yl}ethyl)-N-cyclopentyl-5-oxo-D-prolinamide |
| 244 | N-(2-{5-[3-chloro-4-(methyloxy)phenyl]-3-pyridin-4-yl-1H-1,2,4-triazol-1-yl}ethyl)-N-cyclopentyl-5-methylpyrazine-2-carboxamide |
| 245 | N-(2-{5-[3-chloro-4-(methyloxy)phenyl]-3-pyridin-4-yl-1H-1,2,4-triazol-1-yl}ethyl)-N-cyclopentyl-2-methylcyclohexanecarboxamide |
| 246 | N-(2-{5-[3-chloro-4-(methyloxy)phenyl]-3-pyridin-4-yl-1H-1,2,4-triazol-1-yl}ethyl)-N-cyclopentyl-3-(methyloxy)cyclohexanecarboxamide |
| 247 | N-(2-{5-[3-chloro-4-(methyloxy)phenyl]-3-pyridin-4-yl-1H-1,2,4-triazol-1-yl}ethyl)-N-cyclopentyl-4-(methyloxy)cyclohexanecarboxamide |
| 248 | N-(2-{5-[3-chloro-4-(methyloxy)phenyl]-3-pyridin-4-yl-1H-1,2,4-triazol-1-yl}ethyl)-N-cyclopentyl-2-(2-methyl-1H-indol-3-yl)acetamide |
| 249 | N-(2-{5-[3-chloro-4-(methyloxy)phenyl]-3-pyridin-4-yl-1H-1,2,4-triazol-1-yl}ethyl)-N-cyclopentyltetrahydrofuran-3-carboxamide |
| 250 | N-(2-{5-[3-chloro-4-(methyloxy)phenyl]-3-pyridin-4-yl-1H-1,2,4-triazol-1-yl}ethyl)-N-cyclopentyl-2,6-bis(methyloxy)pyridine-3-carboxamide |
| 251 | N-(2-{5-[3-chloro-4-(methyloxy)phenyl]-3-pyridin-4-yl-1H-1,2,4-triazol-1-yl}ethyl)-N-cyclopentyl-3-(2-methylphenyl)propanamide |
| 252 | N~2~-[(butylamino)carbonyl]-N-(2-{5-[3-chloro-4-(methyloxy)phenyl]-3-pyridin-4-yl-1H-1,2,4-triazol-1-yl}ethyl)-N-cyclopentylglycinamide |
| 253 | N-{2-[(2-{5-[3-chloro-4-(methyloxy)phenyl]-3-pyridin-4-yl-1H-1,2,4-triazol-1-yl}ethyl)(cyclopentyl)amino]-2-oxoethyl}-N-methylbenzamide |
| 254 | N-(2-{5-[3-chloro-4-(methyloxy)phenyl]-3-pyridin-4-yl-1H-1,2,4-triazol-1-yl}ethyl)-4-(cyclohex-2-en-1-yloxy)-N-cyclopentylbenzamide |
| 255 | 2-[(1S,4R)-bicyclo[2.2.1]hept-2-yl]-N-(2-{5-[3-chloro-4-(methyloxy)phenyl]-3-pyridin-4-yl-1H-1,2,4-triazol-1-yl}ethyl)-N-cyclopentylacetamide |
| 256 | (1S,4R)-N-(2-{5-[3-chloro-4-(methyloxy)phenyl]-3-pyridin-4-yl-1H-1,2,4-triazol-1-yl}ethyl)-N-cyclopentylbicyclo[2.2.1]heptane-2-carboxamide |
| 257 | N-(2-{5-[3-chloro-4-(methyloxy)phenyl]-3-pyridin-4-yl-1H-1,2,4-triazol-1-yl}ethyl)-N-cyclopentyl-2-{3-(methyloxy)-4-[(phenylmethyl)oxy]phenyl}acetamide |
| 258 | N-(2-{5-[3-chloro-4-(methyloxy)phenyl]-3-pyridin-4-yl-1H-1,2,4-triazol-1-yl}ethyl)-N-cyclopentylcyclopropane-1,1-dicarboxamide |
| 259 | N-(2-{5-[3-chloro-4-(methyloxy)phenyl]-3-pyridin-4-yl-1H-1,2,4-triazol-1-yl}ethyl)-N-cyclopentyl-2-methyl-4-oxo-4-phenylbutanamide |
| 260 | N-(2-{5-[3-chloro-4-(methyloxy)phenyl]-3-pyridin-4-yl-1H-1,2,4-triazol-1-yl}ethyl)-N-cyclopentyl-2-[4-(methylsulfonyl)phenyl]acetamide |
| 261 | N-(2-{5-[3-chloro-4-(methyloxy)phenyl]-3-pyridin-4-yl-1H-1,2,4-triazol-1-yl}ethyl)-N-cyclopentyl-3,5-dimethyl-4-[(phenylmethyl)oxy]benzamide |
| 262 | (1R,2S)-N-(2-{5-[3-chloro-4-(methyloxy)phenyl]-3-pyridin-4-yl-1H-1,2,4-triazol-1-yl}ethyl)-N-cyclopentyl-2-(phenylcarbonyl)cyclohexanecarboxamide |
| 263 | (1R,2R)-N-(2-{5-[3-chloro-4-(methyloxy)phenyl]-3-pyridin-4-yl-1H-1,2,4-triazol-1-yl}ethyl)-N-cyclopentyl-2-(phenylcarbonyl)cyclohexanecarboxamide |
| 264 | (1R,2R)-N-(2-{5-[3-chloro-4-(methyloxy)phenyl]-3-pyridin-4-yl-1H-1,2,4-triazol-1-yl}ethyl)-N-cyclopentyl-2-[(4-methylphenyl)carbonyl]cyclohexanecarboxamide |
| 265 | 2-[2,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylacetamide |
| 266 | Nalpha-acetyl-N-(2-{5-[3-chloro-4-(methyloxy)phenyl]-3-pyridin-4-yl-1H-1,2,4-triazol-1-yl}ethyl)-N-cyclopentyl-O-methyl-3-(methyloxy)-D-tyrosinamide |
| 267 | N-(2-{5-[3-chloro-4-(methyloxy)phenyl]-3-pyridin-4-yl-1H-1,2,4-triazol-1-yl}ethyl)-N-cyclopentyl-2-[(phenylmethyl)oxy]propanamide |
| 268 | N-(2-{5-[3-chloro-4-(methyloxy)phenyl]-3-pyridin-4-yl-1H-1,2,4-triazol-1-yl}ethyl)-N-cyclopentyl-1-methylcyclopropanecarboxamide |
| 269 | N-(2-{5-[3-chloro-4-(methyloxy)phenyl]-3-pyridin-4-yl-1H-1,2,4-triazol-1-yl}ethyl)-N-cyclopentyl-4-(methylthio)benzamide |

TABLE 1-continued

| Entry | Name |
|---|---|
| 270 | N-(2-{5-[3-chloro-4-(methyloxy)phenyl]-3-pyridin-4-yl-1H-1,2,4-triazol-1-yl}ethyl)-N-cyclopentylcycloheptanecarboxamide |
| 271 | N-(2-{5-[3-chloro-4-(methyloxy)phenyl]-3-pyridin-4-yl-1H-1,2,4-triazol-1-yl}ethyl)-N-cyclopentyl-5-oxohexanamide |
| 272 | N-(2-{5-[3-chloro-4-(methyloxy)phenyl]-3-pyridin-4-yl-1H-1,2,4-triazol-1-yl}ethyl)-N-cyclopentyl-3-(2-nitrophenyl)-2-oxopropanamide |
| 273 | N-(2-{5-[3-chloro-4-(methyloxy)phenyl]-3-pyridin-4-yl-1H-1,2,4-triazol-1-yl}ethyl)-N-cyclopentyl-2,3,5,6-tetrafluoro-4-methylbenzamide |
| 274 | 3-(aminosulfonyl)-4-chloro-N-(2-{5-[3-chloro-4-(methyloxy)phenyl]-3-pyridin-4-yl-1H-1,2,4-triazol-1-yl}ethyl)-N-cyclopentylbenzamide |
| 275 | N-(2-{5-[3-chloro-4-(methyloxy)phenyl]-3-pyridin-4-yl-1H-1,2,4-triazol-1-yl}ethyl)-N-cyclopentyl-2-methylpent-4-enamide |
| 276 | (3E)-N-(2-{5-[3-chloro-4-(methyloxy)phenyl]-3-pyridin-4-yl-1H-1,2,4-triazol-1-yl}ethyl)-N-cyclopentyloct-3-enamide |
| 277 | 2-bromo-N-(2-{5-[3-chloro-4-(methyloxy)phenyl]-3-pyridin-4-yl-1H-1,2,4-triazol-1-yl}ethyl)-N-cyclopentyl-4,5-bis(methyloxy)benzamide |
| 278 | N-(2-{5-[3-chloro-4-(methyloxy)phenyl]-3-pyridin-4-yl-1H-1,2,4-triazol-1-yl}ethyl)-N-cyclopentyl-2-methyl-4-(methyloxy)benzamide |
| 279 | N-(2-{5-[3-chloro-4-(methyloxy)phenyl]-3-pyridin-4-yl-1H-1,2,4-triazol-1-yl}ethyl)-N-cyclopentyl-2-(ethylthio)acetamide |
| 280 | N-(2-{5-[3-chloro-4-(methyloxy)phenyl]-3-pyridin-4-yl-1H-1,2,4-triazol-1-yl}ethyl)-N-cyclopentyl-2-(methylthio)benzamide |
| 281 | N-(2-{5-[3-chloro-4-(methyloxy)phenyl]-3-pyridin-4-yl-1H-1,2,4-triazol-1-yl}ethyl)-N-cyclopentyl-2-(2,3-difluorophenyl)acetamide |
| 282 | N-(2-{5-[3-chloro-4-(methyloxy)phenyl]-3-pyridin-4-yl-1H-1,2,4-triazol-1-yl}ethyl)-N-cyclopentyl-4'-methylbiphenyl-2-carboxamide |
| 283 | 3,5-dibromo-N-(2-{5-[3-chloro-4-(methyloxy)phenyl]-3-pyridin-4-yl-1H-1,2,4-triazol-1-yl}ethyl)-N-cyclopentylbenzamide |
| 284 | 3-chloro-N-(2-{5-[3-chloro-4-(methyloxy)phenyl]-3-pyridin-4-yl-1H-1,2,4-triazol-1-yl}ethyl)-N-cyclopentyl-2-methylbenzamide |
| 285 | N-(2-{5-[3-chloro-4-(methyloxy)phenyl]-3-pyridin-4-yl-1H-1,2,4-triazol-1-yl}ethyl)-N-cyclopentyl-3-(methylthio)propanamide |
| 286 | N-(2-{5-[3-chloro-4-(methyloxy)phenyl]-3-pyridin-4-yl-1H-1,2,4-triazol-1-yl}ethyl)-N-cyclopentyl-3-methylcyclohexanecarboxamide |
| 287 | N-(2-{5-[3-chloro-4-(methyloxy)phenyl]-3-pyridin-4-yl-1H-1,2,4-triazol-1-yl}ethyl)-N-cyclopentyl-4-methylcyclohexanecarboxamide |
| 288 | N-(2-{5-[3-chloro-4-(methyloxy)phenyl]-3-pyridin-4-yl-1H-1,2,4-triazol-1-yl}ethyl)-5-cyclohexyl-N-cyclopentylpentanamide |
| 289 | N-(2-{5-[3-chloro-4-(methyloxy)phenyl]-3-pyridin-4-yl-1H-1,2,4-triazol-1-yl}ethyl)-N-cyclopentyl-2-(4-methylcyclohexyl)acetamide |
| 290 | N-(2-{5-[3-chloro-4-(methyloxy)phenyl]-3-pyridin-4-yl-1H-1,2,4-triazol-1-yl}ethyl)-N-cyclopentyl-2-(methylthio)acetamide |
| 291 | (1R,4R)-N-(2-{5-[3-chloro-4-(methyloxy)phenyl]-3-pyridin-4-yl-1H-1,2,4-triazol-1-yl}ethyl)-N-cyclopentylbicyclo[2.2.1]hept-5-ene-2-carboxamide |
| 292 | N-(2-{5-[3-chloro-4-(methyloxy)phenyl]-3-pyridin-4-yl-1H-1,2,4-triazol-1-yl}ethyl)-N-cyclopentyl-4,4,4-trifluoro-2-methylbutanamide |
| 293 | N-(2-{5-[3-chloro-4-(methyloxy)phenyl]-3-pyridin-4-yl-1H-1,2,4-triazol-1-yl}ethyl)-N-cyclopentyl-2-methyl-3-phenylpropanamide |
| 294 | N-(2-{5-[3-chloro-4-(methyloxy)phenyl]-3-pyridin-4-yl-1H-1,2,4-triazol-1-yl}ethyl)-N-cyclopentyl-2-[4-(methylthio)phenyl]acetamide |
| 295 | N-(2-{5-[3-chloro-4-(methyloxy)phenyl]-3-pyridin-4-yl-1H-1,2,4-triazol-1-yl}ethyl)-N-cyclopentyl-2-(methyloxy)-4-nitrobenzamide |
| 296 | N-(2-{5-[3-chloro-4-(methyloxy)phenyl]-3-pyridin-4-yl-1H-1,2,4-triazol-1-yl}ethyl)-5-[2-chloro-5-(trifluoromethyl)phenyl]-N-cyclopentylfuran-2-carboxamide |
| 297 | N-(2-{5-[3-chloro-4-(methyloxy)phenyl]-3-pyridin-4-yl-1H-1,2,4-triazol-1-yl}ethyl)-N-cyclopentyl-5-fluoro-2-(methyloxy)benzamide |
| 298 | 3-[3,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylpropanamide |
| 299 | N-(2-{5-[3-chloro-4-(methyloxy)phenyl]-3-pyridin-4-yl-1H-1,2,4-triazol-1-yl}ethyl)-N-cyclopentyl-4-(3,5-difluorophenyl)-4-oxobutanamide |
| 300 | N-(2-{5-[3-chloro-4-(methyloxy)phenyl]-3-pyridin-4-yl-1H-1,2,4-triazol-1-yl}ethyl)-N-cyclopentyl-1-methyl-1H-indole-3-carboxamide |
| 301 | N-(2-{5-[3-chloro-4-(methyloxy)phenyl]-3-pyridin-4-yl-1H-1,2,4-triazol-1-yl}ethyl)-N-cyclopentyl-4-(phenyloxy)benzamide |
| 302 | N-(2-{5-[3-chloro-4-(methyloxy)phenyl]-3-pyridin-4-yl-1H-1,2,4-triazol-1-yl}ethyl)-N-cyclopentyl-2-[(1E)-3,3-dimethyltriaz-1-en-1-yl]benzamide |
| 303 | N-(2-{5-[3-chloro-4-(methyloxy)phenyl]-3-pyridin-4-yl-1H-1,2,4-triazol-1-yl}ethyl)-N-cyclopentyl-2-[(3-methylphenyl)oxy]acetamide |
| 304 | N-(2-{5-[3-chloro-4-(methyloxy)phenyl]-3-pyridin-4-yl-1H-1,2,4-triazol-1-yl}ethyl)-N-cyclopentyl-2-{[4-(1-methylethyl)phenyl]oxy}acetamide |
| 305 | N-(2-{5-[3-chloro-4-(methyloxy)phenyl]-3-pyridin-4-yl-1H-1,2,4-triazol-1-yl}ethyl)-N-cyclopentyl-N'-(4-nitrophenyl)ethanediamide |
| 306 | N-(2-{5-[3-chloro-4-(methyloxy)phenyl]-3-pyridin-4-yl-1H-1,2,4-triazol-1-yl}ethyl)-N-cyclopentyl-3-(ethyloxy)benzamide |
| 307 | N-(2-{5-[3-chloro-4-(methyloxy)phenyl]-3-pyridin-4-yl-1H-1,2,4-triazol-1-yl}ethyl)-N-cyclopentyl-4-(methyloxy)-3-[(phenylmethyl)oxy]benzamide |

TABLE 1-continued

| Entry | Name |
|---|---|
| 308 | N-(2-{5-[3-chloro-4-(methyloxy)phenyl]-3-pyridin-4-yl-1H-1,2,4-triazol-1-yl}ethyl)-N-cyclopentyl-4-[(phenylmethyl)oxy]benzamide |
| 309 | N-(2-{5-[3-chloro-4-(methyloxy)phenyl]-3-pyridin-4-yl-1H-1,2,4-triazol-1-yl}ethyl)-N-cyclopentyl-4-oxo-4-(2-thienyl)butanamide |
| 310 | N-(2-{5-[3-chloro-4-(methyloxy)phenyl]-3-pyridin-4-yl-1H-1,2,4-triazol-1-yl}ethyl)-N-cyclopentyl-3-nitro-5-(trifluoromethyl)benzamide |
| 311 | (4E)-4-[(aminocarbonyl)hydrazono]-N-(2-{5-[3-chloro-4-(methyloxy)phenyl]-3-pyridin-4-yl-1H-1,2,4-triazol-1-yl}ethyl)-N-cyclopentylpentanamide |
| 312 | N-(2-{5-[3-chloro-4-(methyloxy)phenyl]-3-pyridin-4-yl-1H-1,2,4-triazol-1-yl}ethyl)-4-cyclohexyl-N-cyclopentylbenzamide |
| 313 | 4-(1H-benzimidazol-1-ylmethyl)-N-(2-{5-[3-chloro-4-(methyloxy)phenyl]-3-pyridin-4-yl-1H-1,2,4-triazol-1-yl}ethyl)-N-cyclopentylbenzamide |
| 314 | 2-(acetylamino)-5-bromo-N-(2-{5-[3-chloro-4-(methyloxy)phenyl]-3-pyridin-4-yl-1H-1,2,4-triazol-1-yl}ethyl)-N-cyclopentylbenzamide |
| 315 | 4-bromo-N-(2-{5-[3-chloro-4-(methyloxy)phenyl]-3-pyridin-4-yl-1H-1,2,4-triazol-1-yl}ethyl)-N-cyclopentyl-2-methylbenzamide |
| 316 | N-(2-{5-[3-chloro-4-(methyloxy)phenyl]-3-pyridin-4-yl-1H-1,2,4-triazol-1-yl}ethyl)-N-cyclopentyl-2-(1,3-dioxo-1,3-dihydro-2H-isoindol-2-yl)benzamide |
| 317 | phenylmethyl 4-{[(2-{5-[3-chloro-4-(methyloxy)phenyl]-3-pyridin-4-yl-1H-1,2,4-triazol-1-yl}ethyl)(cyclopentyl)amino]carbonyl}piperidine-1-carboxylate |
| 318 | 4,5-dibromo-N-(2-{5-[3-chloro-4-(methyloxy)phenyl]-3-pyridin-4-yl-1H-1,2,4-triazol-1-yl}ethyl)-N-cyclopentylfuran-2-carboxamide |
| 319 | N-(2-{5-[3-chloro-4-(methyloxy)phenyl]-3-pyridin-4-yl-1H-1,2,4-triazol-1-yl}ethyl)-N-cyclopentyl-2-oxo-2-(2,4,6-trimethylphenyl)acetamide |
| 320 | N-(2-{5-[3-chloro-4-(methyloxy)phenyl]-3-pyridin-4-yl-1H-1,2,4-triazol-1-yl}ethyl)-N-cyclopentyl-4-(ethylthio)benzamide |
| 321 | N-(2-{5-[3-chloro-4-(methyloxy)phenyl]-3-pyridin-4-yl-1H-1,2,4-triazol-1-yl}ethyl)-N-cyclopentyl-2-(phenylthio)acetamide |
| 322 | 3,5-dibromo-N-(2-{5-[3-chloro-4-(methyloxy)phenyl]-3-pyridin-4-yl-1H-1,2,4-triazol-1-yl}ethyl)-N-cyclopentyl-4-methylbenzamide |
| 323 | N-(2-{5-[3-chloro-4-(methyloxy)phenyl]-3-pyridin-4-yl-1H-1,2,4-triazol-1-yl}ethyl)-2-cyano-N-cyclopentylacetamide |
| 324 | N-(2-{5-[3-chloro-4-(methyloxy)phenyl]-3-pyridin-4-yl-1H-1,2,4-triazol-1-yl}ethyl)-N-cyclopentyl-4-(1,3-dioxo-1,3-dihydro-2H-isoindol-2-yl)benzamide |
| 325 | N-(2-{5-[3-chloro-4-(methyloxy)phenyl]-3-pyridin-4-yl-1H-1,2,4-triazol-1-yl}ethyl)-1-cyano-N-cyclopentylcyclopropanecarboxamide |
| 326 | N-(2-{5-[3-chloro-4-(methyloxy)phenyl]-3-pyridin-4-yl-1H-1,2,4-triazol-1-yl}ethyl)-N-cyclopentylhex-5-ynamide |
| 327 | N-(2-{5-[3-chloro-4-(methyloxy)phenyl]-3-pyridin-4-yl-1H-1,2,4-triazol-1-yl}ethyl)-N-cyclopentyl-2-(2,3-dihydro-1H-inden-2-yl)acetamide |
| 328 | N-(2-{5-[3-chloro-4-(methyloxy)phenyl]-3-pyridin-4-yl-1H-1,2,4-triazol-1-yl}ethyl)-N-cyclopentyl-4-[4-(methylsulfonyl)phenyl]-4-oxobutanamide |
| 329 | N-(2-{5-[3-chloro-4-(methyloxy)phenyl]-3-pyridin-4-yl-1H-1,2,4-triazol-1-yl}ethyl)-N-cyclopentyl-2-(3,5-dimethylphenyl)acetamide |
| 330 | N-(2-{5-[3-chloro-4-(methyloxy)phenyl]-3-pyridin-4-yl-1H-1,2,4-triazol-1-yl}ethyl)-N-cyclopentyl-N',N'-bis[(1S)-1-phenylethyl]benzene-1,2-dicarboxamide |
| 331 | N-(2-{5-[3-chloro-4-(methyloxy)phenyl]-3-pyridin-4-yl-1H-1,2,4-triazol-1-yl}ethyl)-N-cyclopentyl-6-(methyloxy)naphthalene-2-carboxamide |
| 332 | N-(2-{5-[3-chloro-4-(methyloxy)phenyl]-3-pyridin-4-yl-1H-1,2,4-triazol-1-yl}ethyl)-2-cycloheptyl-N-cyclopentylacetamide |
| 333 | 2-chloro-N-(2-{5-[3-chloro-4-(methyloxy)phenyl]-3-pyridin-4-yl-1H-1,2,4-triazol-1-yl}ethyl)-N-cyclopentyl-6-fluorobenzamide |
| 334 | N-(2-{5-[3-chloro-4-(methyloxy)phenyl]-3-pyridin-4-yl-1H-1,2,4-triazol-1-yl}ethyl)-N-cyclopentyl-3,5-dimethylbenzamide |
| 335 | 4-(4-bromophenyl)-N-(2-{5-[3-chloro-4-(methyloxy)phenyl]-3-pyridin-4-yl-1H-1,2,4-triazol-1-yl}ethyl)-N-cyclopentyl-4-oxobutanamide |
| 336 | N-(2-{5-[3-chloro-4-(methyloxy)phenyl]-3-pyridin-4-yl-1H-1,2,4-triazol-1-yl}ethyl)-N-cyclopentyl-2-[(4-methylphenyl)carbonyl]benzamide |
| 337 | N-(2-{5-[3-chloro-4-(methyloxy)phenyl]-3-pyridin-4-yl-1H-1,2,4-triazol-1-yl}ethyl)-2-[(2-cyanophenyl)thio]-N-cyclopentylbenzamide |
| 338 | N-(2-{5-[3-chloro-4-(methyloxy)phenyl]-3-pyridin-4-yl-1H-1,2,4-triazol-1-yl}ethyl)-N-cyclopentyl-2-[(1R,2S,3R)-3-methyl-2-(nitromethyl)-5-oxocyclopentyl]acetamide |
| 339 | N-(2-{5-[3-chloro-4-(methyloxy)phenyl]-3-pyridin-4-yl-1H-1,2,4-triazol-1-yl}ethyl)-N-cyclopentyl-2-(phenyloxy)butanamide |
| 340 | N-(2-{5-[3-chloro-4-(methyloxy)phenyl]-3-pyridin-4-yl-1H-1,2,4-triazol-1-yl}ethyl)-N-cyclopentyl-2-[(2-{[2-(methyloxy)ethyl]oxy}ethyl)oxy]acetamide |
| 341 | N-(2-{5-[3-chloro-4-(methyloxy)phenyl]-3-pyridin-4-yl-1H-1,2,4-triazol-1-yl}ethyl)-N-cyclopentyl-1,5-dimethyl-1H-pyrazole-3-carboxamide |
| 342 | 2-chloro-N-(2-{5-[3-chloro-4-(methyloxy)phenyl]-3-pyridin-4-yl-1H-1,2,4-triazol-1-yl}ethyl)-N-cyclopentyl-5-(methylthio)benzamide |
| 343 | N-(2-{5-[3-chloro-4-(methyloxy)phenyl]-3-pyridin-4-yl-1H-1,2,4-triazol-1-yl}ethyl)-2,2-dicyclohexyl-N-cyclopentylacetamide |
| 344 | N-(2-{5-[3-chloro-4-(methyloxy)phenyl]-3-pyridin-4-yl-1H-1,2,4-triazol-1-yl}ethyl)-N-cyclopentyl-2-oxo-3-phenylpropanamide |
| 345 | N-(2-{5-[3-chloro-4-(methyloxy)phenyl]-3-pyridin-4-yl-1H-1,2,4-triazol-1-yl}ethyl)-N-cyclopentylprop-2-ynamide |

TABLE 1-continued

| Entry | Name |
|---|---|
| 346 | N-alpha-acetyl-N-(2-{5-[3-chloro-4-(methyloxy)phenyl]-3-pyridin-4-yl-1H-1,2,4-triazol-1-yl}ethyl)-N-cyclopentyltryptophanamide |
| 347 | N-(2-{5-[3-chloro-4-(methyloxy)phenyl]-3-pyridin-4-yl-1H-1,2,4-triazol-1-yl}ethyl)-N-cyclopentyl-2-(1,3-dioxo-1,3-dihydro-2H-isoindol-2-yl)acetamide |
| 348 | N-(2-{5-[3-chloro-4-(methyloxy)phenyl]-3-pyridin-4-yl-1H-1,2,4-triazol-1-yl}ethyl)-2-cyclopent-2-en-1-yl-N-cyclopentylacetamide |
| 349 | 2,5-dichloro-N-(2-{5-[3-chloro-4-(methyloxy)phenyl]-3-pyridin-4-yl-1H-1,2,4-triazol-1-yl}ethyl)-N-cyclopentylbenzamide |
| 350 | N-(2-{5-[3-chloro-4-(methyloxy)phenyl]-3-pyridin-4-yl-1H-1,2,4-triazol-1-yl}ethyl)-N-cyclopentyl-2,5-dimethylbenzamide |
| 351 | N-(2-{5-[3-chloro-4-(methyloxy)phenyl]-3-pyridin-4-yl-1H-1,2,4-triazol-1-yl}ethyl)-N-cyclopentyl-2,6-dimethylbenzamide |
| 352 | 3-bromo-N-(2-{5-[3-chloro-4-(methyloxy)phenyl]-3-pyridin-4-yl-1H-1,2,4-triazol-1-yl}ethyl)-N-cyclopentyl-4-methylbenzamide |
| 353 | N-(2-{5-[3-chloro-4-(methyloxy)phenyl]-3-pyridin-4-yl-1H-1,2,4-triazol-1-yl}ethyl)-3-cyclohexyl-N-cyclopentylpropanamide |
| 354 | 5-bromo-2-chloro-N-(2-{5-[3-chloro-4-(methyloxy)phenyl]-3-pyridin-4-yl-1H-1,2,4-triazol-1-yl}ethyl)-N-cyclopentylbenzamide |
| 355 | N-(2-{5-[3-chloro-4-(methyloxy)phenyl]-3-pyridin-4-yl-1H-1,2,4-triazol-1-yl}ethyl)-N-cyclopentyl-2-(phenylmethyl)benzamide |
| 356 | N-(2-{5-[3-chloro-4-(methyloxy)phenyl]-3-pyridin-4-yl-1H-1,2,4-triazol-1-yl}ethyl)-N-cyclopentyl-4-methyl-3-(methyloxy)benzamide |
| 357 | N-(2-{5-[3-chloro-4-(methyloxy)phenyl]-3-pyridin-4-yl-1H-1,2,4-triazol-1-yl}ethyl)-N-cyclopentyl-2-[6-(methyloxy)-3-oxo-2,3-dihydro-1H-inden-1-yl]acetamide |
| 358 | N-(2-{5-[3-chloro-4-(methyloxy)phenyl]-3-pyridin-4-yl-1H-1,2,4-triazol-1-yl}ethyl)-N-cyclopentyl-5-oxo-5-phenylpentanamide |
| 359 | N-(2-{5-[3-chloro-4-(methyloxy)phenyl]-3-pyridin-4-yl-1H-1,2,4-triazol-1-yl}ethyl)-N-cyclopentyl-2-nitro-4-(trifluoromethyl)benzamide |
| 360 | N-(2-{5-[3-chloro-4-(methyloxy)phenyl]-3-pyridin-4-yl-1H-1,2,4-triazol-1-yl}ethyl)-N-cyclopentyl-5-methyl-2-nitrobenzamide |
| 361 | N-(2-{5-[3-chloro-4-(methyloxy)phenyl]-3-pyridin-4-yl-1H-1,2,4-triazol-1-yl}ethyl)-N-cyclopentyl-2-(4-nitrophenyl)propanamide |
| 362 | 3-(1H-benzimidazol-2-yl)-N-(2-{5-[3-chloro-4-(methyloxy)phenyl]-3-pyridin-4-yl-1H-1,2,4-triazol-1-yl}ethyl)-N-cyclopentylpropanamide |
| 363 | N-(2-{5-[3-chloro-4-(methyloxy)phenyl]-3-pyridin-4-yl-1H-1,2,4-triazol-1-yl}ethyl)-N-cyclopentyl-5-fluoro-2-methylbenzamide |
| 364 | 2,6-dichloro-N-(2-{5-[3-chloro-4-(methyloxy)phenyl]-3-pyridin-4-yl-1H-1,2,4-triazol-1-yl}ethyl)-N-cyclopentylpyridine-3-carboxamide |
| 365 | N-(2-{5-[3-chloro-4-(methyloxy)phenyl]-3-pyridin-4-yl-1H-1,2,4-triazol-1-yl}ethyl)-N-cyclopentyl-4-nitro-1H-pyrazole-3-carboxamide |
| 366 | N-(2-{5-[3-chloro-4-(methyloxy)phenyl]-3-pyridin-4-yl-1H-1,2,4-triazol-1-yl}ethyl)-N-cyclopentyl-5-nitro-1H-pyrazole-3-carboxamide |
| 367 | N-(2-{5-[3-chloro-4-(methyloxy)phenyl]-3-pyridin-4-yl-1H-1,2,4-triazol-1-yl}ethyl)-N-cyclopentyl-3-(phenylcarbonyl)pyridine-2-carboxamide |
| 368 | N-(2-{5-[3-chloro-4-(methyloxy)phenyl]-3-pyridin-4-yl-1H-1,2,4-triazol-1-yl}ethyl)-N-cyclopentyl-3-[(trifluoromethyl)thio]benzamide |
| 369 | N-(2-{5-[3-chloro-4-(methyloxy)phenyl]-3-pyridin-4-yl-1H-1,2,4-triazol-1-yl}ethyl)-N-cyclopentyl-4-[(phenylmethyl)oxy]butanamide |
| 370 | N-(2-{5-[3-chloro-4-(methyloxy)phenyl]-3-pyridin-4-yl-1H-1,2,4-triazol-1-yl}ethyl)-N-cyclopentyl-2-(propyloxy)benzamide |
| 371 | 2-acetyl-N-(2-{5-[3-chloro-4-(methyloxy)phenyl]-3-pyridin-4-yl-1H-1,2,4-triazol-1-yl}ethyl)-N-cyclopentylbenzamide |
| 372 | N-(2-{5-[3-chloro-4-(methyloxy)phenyl]-3-pyridin-4-yl-1H-1,2,4-triazol-1-yl}ethyl)-N-cyclopentyl-4-(4-nitrophenyl)butanamide |
| 373 | N-(2-{5-[3-chloro-4-(methyloxy)phenyl]-3-pyridin-4-yl-1H-1,2,4-triazol-1-yl}ethyl)-N-cyclopentyl-9-oxo-9H-fluorene-1-carboxamide |
| 374 | N-(2-{5-[3-chloro-4-(methyloxy)phenyl]-3-pyridin-4-yl-1H-1,2,4-triazol-1-yl}ethyl)-N-cyclopentyl-2,2,3,3-tetramethylcyclopropanecarboxamide |
| 375 | 2-[(4-acetylphenyl)oxy]-N-(2-{5-[3-chloro-4-(methyloxy)phenyl]-3-pyridin-4-yl-1H-1,2,4-triazol-1-yl}ethyl)-N-cyclopentylacetamide |
| 376 | N-(2-{5-[3-chloro-4-(methyloxy)phenyl]-3-pyridin-4-yl-1H-1,2,4-triazol-1-yl}ethyl)-N-cyclopentyl-3-fluoro-2-methylbenzamide |
| 377 | N-(2-{5-[3-chloro-4-(methyloxy)phenyl]-3-pyridin-4-yl-1H-1,2,4-triazol-1-yl}ethyl)-N-cyclopentyl-N'-[(1R)-1-phenylethyl]butanediamide |
| 378 | N-(2-{5-[3-chloro-4-(methyloxy)phenyl]-3-pyridin-4-yl-1H-1,2,4-triazol-1-yl}ethyl)-N-cyclopentyl-5-(4-nitrophenyl)furan-2-carboxamide |
| 379 | N-(2-{5-[3-chloro-4-(methyloxy)phenyl]-3-pyridin-4-yl-1H-1,2,4-triazol-1-yl}ethyl)-N-cyclopentyl-3-[4-(trifluoromethyl)phenyl]propanamide |
| 380 | N-(2-{5-[3-chloro-4-(methyloxy)phenyl]-3-pyridin-4-yl-1H-1,2,4-triazol-1-yl}ethyl)-N-cyclopentyl-5-(3-nitrophenyl)furan-2-carboxamide |
| 381 | N-(2-{5-[3-chloro-4-(methyloxy)phenyl]-3-pyridin-4-yl-1H-1,2,4-triazol-1-yl}ethyl)-N-cyclopentyl-3-(3,4-difluorophenyl)propanamide |
| 382 | 5-(aminosulfonyl)-2-chloro-N-(2-{5-[3-chloro-4-(methyloxy)phenyl]-3-pyridin-4-yl-1H-1,2,4-triazol-1-yl}ethyl)-N-cyclopentyl-4-fluorobenzamide |
| 383 | N-(2-{5-[3-chloro-4-(methyloxy)phenyl]-3-pyridin-4-yl-1H-1,2,4-triazol-1-yl}ethyl)-N-cyclopentyl-2-(2-oxocyclopentyl)acetamide |

TABLE 1-continued

| Entry | Name |
|---|---|
| 384 | N-(2-{5-[3-chloro-4-(methyloxy)phenyl]-3-pyridin-4-yl-1H-1,2,4-triazol-1-yl}ethyl)-N-cyclopentyl-2-[(4-fluorophenyl)carbonyl]benzamide |
| 385 | N-(2-{5-[3-chloro-4-(methyloxy)phenyl]-3-pyridin-4-yl-1H-1,2,4-triazol-1-yl}ethyl)-2-[(4-chlorophenyl)carbonyl]-N-cyclopentylbenzamide |
| 386 | N-{3-[(2-{5-[3-chloro-4-(methyloxy)phenyl]-3-pyridin-4-yl-1H-1,2,4-triazol-1-yl}ethyl)(cyclopentyl)amino]-3-oxopropyl}-4-nitrobenzamide |
| 387 | N-(2-{5-[3-chloro-4-(methyloxy)phenyl]-3-pyridin-4-yl-1H-1,2,4-triazol-1-yl}ethyl)-N-cyclopentyl-2-(methyloxy)-4-(methylthio)benzamide |
| 388 | N-(2-{5-[3-chloro-4-(methyloxy)phenyl]-3-pyridin-4-yl-1H-1,2,4-triazol-1-yl}ethyl)-N-cyclopentyl-3-(4-methylphenyl)propanamide |
| 389 | 5-chloro-N-(2-{5-[3-chloro-4-(methyloxy)phenyl]-3-pyridin-4-yl-1H-1,2,4-triazol-1-yl}ethyl)-N-cyclopentyl-2-(methyloxy)benzamide |
| 390 | 4-acetyl-N-(2-{5-[3-chloro-4-(methyloxy)phenyl]-3-pyridin-4-yl-1H-1,2,4-triazol-1-yl}ethyl)-N-cyclopentyl-3,5-dimethyl-1H-pyrrole-2-carboxamide |
| 391 | N-(2-{5-[3-chloro-4-(methyloxy)phenyl]-3-pyridin-4-yl-1H-1,2,4-triazol-1-yl}ethyl)-N-cyclopentyl-6-oxoheptanamide |
| 392 | N-(2-{5-[3-chloro-4-(methyloxy)phenyl]-3-pyridin-4-yl-1H-1,2,4-triazol-1-yl}ethyl)-N-cyclopentyl-3,3-dimethyl-2-(phenylmethyl)butanamide |
| 393 | N-(2-{5-[3-chloro-4-(methyloxy)phenyl]-3-pyridin-4-yl-1H-1,2,4-triazol-1-yl}ethyl)-N-cyclopentyl-2-(2-fluorobiphenyl-4-yl)propanamide |
| 394 | N-(2-{5-[3-chloro-4-(methyloxy)phenyl]-3-pyridin-4-yl-1H-1,2,4-triazol-1-yl}ethyl)-N-cyclopentyl-3-oxo-2,3-dihydro-1H-indene-1-carboxamide |
| 395 | 2-{[2,4-bis(1,1-dimethylpropyl)phenyl]oxy}-N-(2-{5-[3-chloro-4-(methyloxy)phenyl]-3-pyridin-4-yl-1H-1,2,4-triazol-1-yl}ethyl)-N-cyclopentylacetamide |
| 396 | 4-{[2,4-bis(1,1-dimethylpropyl)phenyl]oxy}-N-(2-{5-[3-chloro-4-(methyloxy)phenyl]-3-pyridin-4-yl-1H-1,2,4-triazol-1-yl}ethyl)-N-cyclopentylbutanamide |
| 397 | 4-[3,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylbutanamide |
| 398 | N-(2-{5-[3-chloro-4-(methyloxy)phenyl]-3-pyridin-4-yl-1H-1,2,4-triazol-1-yl}ethyl)-N-cyclopentyl-4-(1,2-dihydroacenaphthylen-5-yl)-4-oxobutanamide |
| 399 | N-(2-{5-[3-chloro-4-(methyloxy)phenyl]-3-pyridin-4-yl-1H-1,2,4-triazol-1-yl}ethyl)-N-cyclopentyl-5-[3-(trifluoromethyl)phenyl]furan-2-carboxamide |
| 400 | N-(2-{5-[3-chloro-4-(methyloxy)phenyl]-3-pyridin-4-yl-1H-1,2,4-triazol-1-yl}ethyl)-N-cyclopentyl-1-{[4-(1,1-dimethylethyl)phenyl]sulfonyl}-L-prolinamide |
| 401 | N-(2-{5-[3-chloro-4-(methyloxy)phenyl]-3-pyridin-4-yl-1H-1,2,4-triazol-1-yl}ethyl)-N-cyclopentyl-2-(1H-indol-3-yl)-2-oxoacetamide |
| 402 | N-(2-{5-[3-chloro-4-(methyloxy)phenyl]-3-pyridin-4-yl-1H-1,2,4-triazol-1-yl}ethyl)-2-[(4-chloro-3-nitrophenyl)carbonyl]-N-cyclopentylbenzamide |
| 403 | N-(2-{5-[3-chloro-4-(methyloxy)phenyl]-3-pyridin-4-yl-1H-1,2,4-triazol-1-yl}ethyl)-N-cyclopentyl-2-(ethylthio)-2,2-diphenylacetamide |
| 404 | N-(2-{5-[3-chloro-4-(methyloxy)phenyl]-3-pyridin-4-yl-1H-1,2,4-triazol-1-yl}ethyl)-N-cyclopentyl-2,2-dimethylpent-4-enamide |
| 405 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]benzene-1,2-dicarboxamide |
| 406 | N-(2-{5-[3-chloro-4-(methyloxy)phenyl]-3-pyridin-4-yl-1H-1,2,4-triazol-1-yl}ethyl)-N-cyclopentyl-6-nitrohexanamide |
| 407 | N-(2-{5-[3-chloro-4-(methyloxy)phenyl]-3-pyridin-4-yl-1H-1,2,4-triazol-1-yl}ethyl)-N-cyclopentyl-N~2~-(1H-indol-3-ylacetyl)-L-valinamide |
| 408 | 2,6-dichloro-N-(2-{5-[3-chloro-4-(methyloxy)phenyl]-3-pyridin-4-yl-1H-1,2,4-triazol-1-yl}ethyl)-N-cyclopentyl-3-nitrobenzamide |
| 409 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]butanediamide |
| 410 | N-(2-{5-[3-chloro-4-(methyloxy)phenyl]-3-pyridin-4-yl-1H-1,2,4-triazol-1-yl}ethyl)-N-cyclopentyl-2-fluoro-5-methylbenzamide |
| 411 | N-(2-{5-[3-chloro-4-(methyloxy)phenyl]-3-pyridin-4-yl-1H-1,2,4-triazol-1-yl}ethyl)-N-cyclopentyl-N',N'-bis[(1R)-1-phenylethyl]benzene-1,2-dicarboxamide |
| 412 | 3-[2,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylpropanamide |
| 413 | N-(2-{5-[3-chloro-4-(methyloxy)phenyl]-3-pyridin-4-yl-1H-1,2,4-triazol-1-yl}ethyl)-2-[(2-chlorophenyl)oxy]-N-cyclopentylacetamide |
| 414 | N-(2-{5-[3-chloro-4-(methyloxy)phenyl]-3-pyridin-4-yl-1H-1,2,4-triazol-1-yl}ethyl)-N-cyclopentyl-3,5-dimethyl-4-nitrobenzamide |
| 415 | 3-(1,3-benzodioxol-5-yl)-N-(2-{5-[3-chloro-4-(methyloxy)phenyl]-3-pyridin-4-yl-1H-1,2,4-triazol-1-yl}ethyl)-N-cyclopentylpropanamide |
| 416 | N-(2-{5-[3-chloro-4-(methyloxy)phenyl]-3-pyridin-4-yl-1H-1,2,4-triazol-1-yl}ethyl)-N-cyclopentyl-2-[(2-nitrophenyl)oxy]acetamide |
| 417 | 3-bromo-N-(2-{5-[3-chloro-4-(methyloxy)phenyl]-3-pyridin-4-yl-1H-1,2,4-triazol-1-yl}ethyl)-N-cyclopentyl-4-(methyloxy)benzamide |
| 418 | N-(2-{5-[3-chloro-4-(methyloxy)phenyl]-3-pyridin-4-yl-1H-1,2,4-triazol-1-yl}ethyl)-N-cyclopentyl-3-(1,3-dioxo-1,3-dihydro-2H-isoindol-2-yl)propanamide |
| 419 | 5-chloro-N-(2-{5-[3-chloro-4-(methyloxy)phenyl]-3-pyridin-4-yl-1H-1,2,4-triazol-1-yl}ethyl)-N-cyclopentylthiophene-2-carboxamide |

TABLE 1-continued

| Entry | Name |
|---|---|
| 420 | N-(2-{5-[3-chloro-4-(methyloxy)phenyl]-3-pyridin-4-yl-1H-1,2,4-triazol-1-yl}ethyl)-N-cyclopentyl-2-phenyl-2-(phenylthio)acetamide |
| 421 | N-(2-{5-[3-chloro-4-(methyloxy)phenyl]-3-pyridin-4-yl-1H-1,2,4-triazol-1-yl}ethyl)-N-cyclopentyl-2-(phenylcarbonyl)benzamide |
| 422 | 5-acetyl-N-(2-{5-[3-chloro-4-(methyloxy)phenyl]-3-pyridin-4-yl-1H-1,2,4-triazol-1-yl}ethyl)-N-cyclopentylthiophene-2-carboxamide |
| 423 | N-(2-{5-[3-chloro-4-(methyloxy)phenyl]-3-pyridin-4-yl-1H-1,2,4-triazol-1-yl}ethyl)-N-cyclopentyl-4-[4-(methyloxy)phenyl]butanamide |
| 424 | 5-bromo-N-(2-{5-[3-chloro-4-(methyloxy)phenyl]-3-pyridin-4-yl-1H-1,2,4-triazol-1-yl}ethyl)-N-cyclopentylthiophene-2-carboxamide |
| 425 | N-(2-{5-[3-chloro-4-(methyloxy)phenyl]-3-pyridin-4-yl-1H-1,2,4-triazol-1-yl}ethyl)-N-cyclopentyl-4-nitrobenzamide |
| 426 | N-(2-{5-[3-chloro-4-(methyloxy)phenyl]-3-pyridin-4-yl-1H-1,2,4-triazol-1-yl}ethyl)-N-cyclopentyl-9H-xanthene-9-carboxamide |
| 427 | N~2~-acetyl-N-(2-{5-[3-chloro-4-(methyloxy)phenyl]-3-pyridin-4-yl-1H-1,2,4-triazol-1-yl}ethyl)-N-cyclopentylvalinamide |
| 428 | N-cyclopentyl-N-{2-[5-methyl-3-(2-{[(3R)-pyrrolidin-3-ylmethyl]amino}pyridin-4-yl)-1H-1,2,4-triazol-1-yl]ethyl}-2-naphthalen-1-ylacetamide |
| 429 | N-cyclopentyl-N-{2-[5-methyl-3-(2-{[(3S)-pyrrolidin-3-ylmethyl]amino}pyridin-4-yl)-1H-1,2,4-triazol-1-yl]ethyl}-2-naphthalen-1-ylacetamide |
| 430 | N-[4-(1-{2-[cyclopentyl(naphthalen-1-ylacetyl)amino]ethyl}-5-methyl-1H-1,2,4-triazol-3-yl)pyridin-2-yl]-N~2~,N~2~-dimethylglycinamide |
| 431 | N-cyclopentyl-N-{2-[5-methyl-3-(2-{[(methyloxy)acetyl]amino}pyridin-4-yl)-1H-1,2,4-triazol-1-yl]ethyl}-2-naphthalen-1-ylacetamide |
| 432 | N-[4-(1-{2-[cyclopentyl(naphthalen-1-ylacetyl)amino]ethyl}-5-methyl-1H-1,2,4-triazol-3-yl)pyridin-2-yl]propanamide |
| 433 | N-cyclopentyl-N-[2-(5-methyl-3-{2-[(phenylacetyl)amino]pyridin-4-yl}-1H-1,2,4-triazol-1-yl)ethyl]-2-naphthalen-1-ylacetamide |
| 434 | N-[4-(1-{2-[cyclopentyl(naphthalen-1-ylacetyl)amino]ethyl}-5-methyl-1H-1,2,4-triazol-3-yl)pyridin-2-yl]benzamide |
| 435 | N-(2-{3-[2-(acetylamino)pyridin-4-yl]-5-methyl-1H-1,2,4-triazol-1-yl}ethyl)-N-cyclopentyl-2-naphthalen-1-ylacetamide |
| 436 | 2-(5-bromo-1H-indol-3-yl)-N-cyclopentyl-N-[2-(5-methyl-3-pyridin-4-yl-1H-1,2,4-triazol-1-yl)ethyl]acetamide |
| 437 | N-cyclopentyl-2-[5-(methyloxy)-1H-indol-3-yl]-N-[2-(5-methyl-3-pyridin-4-yl-1H-1,2,4-triazol-1-yl)ethyl]acetamide |
| 438 | N-cyclopentyl-2-(1H-indol-3-yl)-N-[2-(5-methyl-3-pyridin-4-yl-1H-1,2,4-triazol-1-yl)ethyl]acetamide |
| 439 | methyl [4-(1-{2-[cyclopentyl(naphthalen-1-ylacetyl)amino]ethyl}-5-methyl-1H-1,2,4-triazol-3-yl)pyridin-2-yl]carbamate |
| 440 | phenylmethyl [4-(1-{2-[cyclopentyl(naphthalen-1-ylacetyl)amino]ethyl}-5-methyl-1H-1,2,4-triazol-3-yl)pyridin-2-yl]carbamate |
| 441 | propyl [4-(1-{2-[cyclopentyl(naphthalen-1-ylacetyl)amino]ethyl}-5-methyl-1H-1,2,4-triazol-3-yl)pyridin-2-yl]carbamate |
| 442 | N-[4-(1-{2-[cyclopentyl(naphthalen-1-ylacetyl)amino]ethyl}-5-methyl-1H-1,2,4-triazol-3-yl)pyridin-2-yl]furan-3-carboxamide |
| 443 | N-cyclopentyl-N-[2-(5-methyl-3-{2-[(methylsulfonyl)amino]pyridin-4-yl}-1H-1,2,4-triazol-1-yl)ethyl]-2-naphthalen-1-ylacetamide |
| 444 | N-cyclopentyl-N-[2-(5-methyl-3-{2-[(phenylsulfonyl)amino]pyridin-4-yl}-1H-1,2,4-triazol-1-yl)ethyl]-2-naphthalen-1-ylacetamide |
| 445 | N-cyclopentyl-N-{2-[5-methyl-3-(2-{[(phenylmethyl)sulfonyl]amino}pyridin-4-yl)-1H-1,2,4-triazol-1-yl]ethyl}-2-naphthalen-1-ylacetamide |
| 446 | N-cyclopentyl-N-(2-{5-methyl-3-[2-({[(phenylmethyl)amino]carbonyl}amino)pyridin-4-yl]-1H-1,2,4-triazol-1-yl}ethyl)-2-naphthalen-1-ylacetamide |
| 447 | N-[4-(1-{2-[cyclopentyl(naphthalen-1-ylacetyl)amino]ethyl}-5-methyl-1H-1,2,4-triazol-3-yl)pyridin-2-yl]-1-ethylpiperidine-4-carboxamide |
| 448 | N-cyclopentyl-2-(2-methyl-3H-indol-3-yl)-N-[2-(5-methyl-3-pyridin-4-yl-1H-1,2,4-triazol-1-yl)ethyl]acetamide |
| 449 | N-cyclopentyl-N-[2-(5-methyl-3-pyridin-4-yl-1H-1,2,4-triazol-1-yl)ethyl]-2-naphthalen-1-ylpropanamide |
| 450 | N-[4-(1-{2-[cyclopentyl(naphthalen-1-ylacetyl)amino]ethyl}-5-methyl-1H-1,2,4-triazol-3-yl)pyridin-2-yl]-N~3~,N~3~-dimethyl-beta-alaninamide |
| 451 | N-[4-(1-{2-[cyclopentyl(naphthalen-1-ylacetyl)amino]ethyl}-5-methyl-1H-1,2,4-triazol-3-yl)pyridin-2-yl]pentanamide |
| 452 | N-{2-[3-(2-aminopyrimidin-4-yl)-5-methyl-1H-1,2,4-triazol-1-yl]ethyl}-N-cyclopentyl-2-naphthalen-1-ylacetamide |
| 453 | N-[4-(1-{2-[cyclopentyl(naphthalen-1-ylacetyl)amino]ethyl}-5-methyl-1H-1,2,4-triazol-3-yl)pyridin-2-yl]-1-methylpiperidine-3-carboxamide |
| 454 | 2-(4-methylpiperazin-1-yl)ethyl [4-(1-{2-[cyclopentyl(naphthalen-1-ylacetyl)amino]ethyl}-5-methyl-1H-1,2,4-triazol-3-yl)pyridin-2-yl]carbamate |
| 455 | 2-(methyloxy)ethyl [4-(1-{2-[cyclopentyl(naphthalen-1-ylacetyl)amino]ethyl}-5-methyl-1H-1,2,4-triazol-3-yl)pyridin-2-yl]carbamate |
| 456 | 2-morpholin-4-ylethyl [4-(1-{2-[cyclopentyl(naphthalen-1-ylacetyl)amino]ethyl}-5-methyl-1H-1,2,4-triazol-3-yl)pyridin-2-yl]carbamate |

TABLE 1-continued

| Entry | Name |
|---|---|
| 457 | N-{2-[5-(2-aminopyrimidin-4-yl)-3-methyl-1H-1,2,4-triazol-1-yl]ethyl}-N-cyclopentyl-2-naphthalen-1-ylacetamide |
| 458 | methyl {4-[1-(2-{cyclopropyl[(naphthalen-1-ylamino)carbonyl]amino}ethyl)-1H-1,2,4-triazol-3-yl]pyridin-2-yl}carbamate |
| 459 | methyl [4-(1-{2-[{[(3-chloro-2-methylphenyl)amino]carbonyl}(cyclopentyl)amino]ethyl}-5-methyl-1H-1,2,4-triazol-3-yl)pyridin-2-yl]carbamate |
| 460 | methyl {4-[1-(2-{cyclopentyl[(naphthalen-1-ylamino)carbonyl]amino}ethyl)-5-methyl-1H-1,2,4-triazol-3-yl]pyridin-2-yl}carbamate |
| 461 | methyl {4-[1-(2-{cyclopentyl[(1-naphthalen-1-ylcyclopropyl)carbonyl]amino}ethyl)-5-methyl-1H-1,2,4-triazol-3-yl]pyridin-2-yl}carbamate |
| 462 | 2-piperidin-1-ylethyl [4-(1-{2-[cyclopentyl(naphthalen-1-ylacetyl)amino]ethyl}-5-methyl-1H-1,2,4-triazol-3-yl)pyridin-2-yl]carbamate |
| 463 | N-{2-[3-(2-aminopyrimidin-4-yl)-5-(trifluoromethyl)-1H-1,2,4-triazol-1-yl]ethyl}-N-cyclopentyl-2-naphthalen-1-ylacetamide |
| 464 | N-{2-[5-(2-aminopyrimidin-4-yl)-3-(trifluoromethyl)-1H-1,2,4-triazol-1-yl]ethyl}-N-cyclopentyl-2-naphthalen-1-ylacetamide |
| 465 | N-cyclopentyl-N-[2-(5-methyl-3-pyrimidin-4-yl-1H-1,2,4-triazol-1-yl)ethyl]-2-naphthalen-1-ylacetamide |
| 466 | N-{2-[3-(2-aminopyrimidin-4-yl)-1H-1,2,4-triazol-1-yl]ethyl}-N-cyclopentyl-2-naphthalen-1-ylacetamide |
| 467 | methyl (4-{1-[2-(cyclopentyl{[(2-ethylphenyl)amino]carbonyl}amino)ethyl]-5-methyl-1H-1,2,4-triazol-3-yl}pyridin-2-yl)carbamate |
| 468 | methyl [4-(1-{2-[{[(3-bromo-2-methylphenyl)amino]carbonyl}(cyclopentyl)amino]ethyl}-5-methyl-1H-1,2,4-triazol-3-yl)pyridin-2-yl]carbamate |
| 469 | methyl [4-(1-{2-[cyclopentyl({[4-fluoro-2-(trifluoromethyl)phenyl]amino}carbonyl)amino]ethyl}-5-methyl-1H-1,2,4-triazol-3-yl)pyridin-2-yl]carbamate |
| 470 | methyl (4-{1-[2-(cyclopentyl{[(2-methylphenyl)amino]carbonyl}amino)ethyl]-5-methyl-1H-1,2,4-triazol-3-yl}pyridin-2-yl)carbamate |
| 471 | methyl (4-{1-[2-(cyclopentyl{[(3-fluoro-2-methylphenyl)amino]carbonyl}amino)ethyl]-5-methyl-1H-1,2,4-triazol-3-yl}pyridin-2-yl)carbamate |
| 472 | methyl (4-{1-[2-(cyclopentyl{[(4-fluoro-2-methylphenyl)amino]carbonyl}amino)ethyl]-5-methyl-1H-1,2,4-triazol-3-yl}pyridin-2-yl)carbamate |
| 473 | methyl [4-(1-{2-[cyclopentyl(phenylacetyl)amino]ethyl}-5-ethyl-1H-1,2,4-triazol-3-yl)pyridin-2-yl]carbamate |
| 474 | methyl {4-[1-{2-[cyclopentyl(naphthalen-1-ylacetyl)amino]ethyl}-5-(trifluoromethyl)-1H-1,2,4-triazol-3-yl]pyridin-2-yl}carbamate |
| 475 | methyl [4-(1-{2-[acetyl(cyclopropyl)amino]ethyl}-5-ethyl-1H-1,2,4-triazol-3-yl)pyridin-2-yl]carbamate |
| 476 | methyl [4-(1-{2-[acetyl(cyclopentyl)amino]ethyl}-5-ethyl-1H-1,2,4-triazol-3-yl)pyridin-2-yl]carbamate |
| 477 | 2-(4-methylpiperazin-1-yl)ethyl {4-[1-(2-{cyclopentyl[(naphthalen-1-ylamino)carbonyl]amino}ethyl)-5-methyl-1H-1,2,4-triazol-3-yl]pyridin-2-yl}carbamate |

Another aspect of the invention is the method according to any of paragraphs [0021]-[0039], wherein treating said kinase-dependent disease or condition comprises modulating the in vivo activity of Tie-2.

Another aspect of the invention is the method according to paragraph [0040], wherein modulating the in vivo activity of Tie-2 comprises inhibition of Tie-2.

Another aspect of the invention is a method of treating diseases or disorders associated with uncontrolled, abnormal, and/or unwanted cellular activities, the method comprising administering, to a mammal in need thereof, a therapeutically effective amount of a composition comprising the compound according to any of paragraphs [0021]-[0039].

Another aspect of the invention is the method of paragraph [0042], wherein the composition is a pharmaceutical composition and the mammal is a human.

Another aspect of the invention is a method of screening for a modulator of Tie-2, the method comprising combining a composition comprising the compound according to any of paragraphs [0021]-[0039] and at least one candidate agent and determining the effect of the candidate agent on the activity of Tie-2.

Another aspect of the invention is a method of inhibiting proliferative activity in a cell, the method comprising administering an effective amount of the compound according to any of paragraphs [0021]-[0039] to a cell or a plurality of cells.

Another aspect of the invention is a method of inhibiting Tie-2, the method comprising exposing either a natural or modified form of Tie-2 to a compound according to any of paragraphs [0021]-[0039]

The present invention also comprises a compound for modulating kinase activity, according to Formula II,

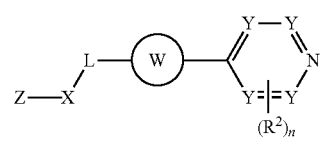

II or a pharmaceutically acceptable salt, hydrate, or prodrug thereof, wherein,

W is selected from one of the following formulae:

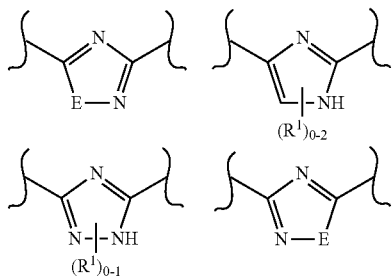

provided Z-X-L- is bonded to the left side of W as depicted, and the ring containing Y is bonded to the right side of W as depicted;
E is —S— or —O—;
$R^1$ and $R^2$, at each occurrence, are independently selected from —H, halogen, —CN, —NH$_2$, —CF$_3$, —NO$_2$, —OR$^6$, —N(R$^6$)R$^7$, —N(R$^6$)N(R$^6$)R$^7$, —S(O)$_{0-2}$R$^7$, —SO$_2$N(R$^6$)R$^7$, —CO$_2$R$^6$, —C(O)N(R$^6$)R$^7$, —N(R$^6$)SO$_2$R$^7$, —N(R$^6$)C(O)R$^7$, —N(R$^6$)C(O)C$_{0-6}$alkyl-N(R$^6$)R$^7$, —N(R$^6$)CO$_2$R$^7$, —C(O)R$^6$, optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl;
n is zero to four;
L is optionally substituted C$_{1-6}$ alkylene;
X is —N(R$^3$)—;
$R^3$ is selected from —H, optionally substituted alkyl, optionally substituted aryl, optionally substituted aryl C$_{1-6}$ alkyl, optionally substituted heterocyclyl, and optionally substituted heterocyclyl C$_{1-6}$ alkyl;
Z is selected from R$^4$, R$^4$C(=O)—, R$^3$(R$^4$)NC(=O)—, R$^4$SO$_2$—, R$^3$(R$^4$)NSO$_2$—, and R$^4$C(=NR$^5$)—;
$R^4$ is selected from optionally substituted aryl, optionally substituted aryl C$_{1-6}$ alkyl, optionally substituted heterocyclyl, and optionally substituted heterocyclyl C$_{1-6}$ alkyl;
optionally R$^3$ and R$^4$, together with the atoms to which they are attached and any additional atoms that link Z with X, are combined to form a first optionally substituted five-to seven-membered heterocyclyl ring, said first optionally substituted five- to seven-membered heterocyclyl ring optionally containing at least one additional heteroatom selected from N, O, S, and P;
$R^5$ is selected from —H, —NO$_2$, —NH$_2$, —N(R$^6$)R$^7$, —CN, —OR$^6$, and optionally substituted C$_{1-6}$ alkyl;
Y is independently either =C(H)— or =N—, provided that there are no more than three of =N— in the ring bearing Y;
each R$^6$ is —H or R$^7$;
each R$^7$ is independently selected from optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl; and
optionally R$^6$ and R$^7$, when taken together with a common nitrogen to which they are attached, form a second optionally substituted five- to seven-membered heterocyclyl ring, said second optionally substituted five- to seven-membered heterocyclyl ring optionally containing at least one additional heteroatom selected from N, O, S, and P.

In another example, the compound is according to paragraph [0047], wherein L is optionally substituted C$_{1-4}$ alkylene.

In another example, the compound is according to paragraph [0048], wherein zero or one of Y is =(N)—.

In another example, the compound is according to paragraph [0049], wherein R$^3$ is either —H or optionally substituted alkyl.

In another example, the compound is according to paragraph [0050], wherein Z is either R$^4$C(=O)— or R$^4$SO$_2$—.

In another example, the compound is according to paragraph [0051], wherein Y is =C(H)—.

In another example, the compound is according to paragraph [0052], wherein R$^4$ is either optionally substituted aryl C$_{1-6}$ alkyl or optionally substituted heteroaryl C$_{1-6}$ alkyl.

In another example, the compound is according to paragraph [0053], wherein R$^1$ is either optionally substituted aryl or optionally substituted heteroaryl.

In another example, the method is according to paragraph [0054], wherein L is optionally substituted —CH$_2$CH$_2$—.

In another example, the compound is according to paragraph [0055], wherein R$^3$ is optionally substituted cycloalkyl or optionally substituted branched alkyl.

In another example, the compound is according to paragraph [0056], wherein Z is R$^4$C(=O)—.

In another example, the compound is according to paragraph [0057], wherein L is —CH$_2$CH$_2$—.

In another example, the compound is according to paragraph [0058], wherein R$^4$ is optionally substituted aryl C$_{1-6}$ alkyl.

In another example, the compound is according to paragraph [0059], wherein R$^4$ is optionally substituted —CH$_2$-naphthylene.

In another example, the compound is according to paragraph [0060], wherein R$^4$ is optionally substituted —CH$_2$-1-naphthylene.

In another example, the compound is according to paragraph [0061], wherein R$^4$ is —CH$_2$-1-naphthylene.

In another example, the compound is according to paragraph [0062], wherein at least one of R$^2$ is selected from —NH$_2$, —N(R$^6$)R$^7$, —N(R$^6$)N(R$^6$)R$^7$, —N(R$^6$)C(O)R$^7$, —N(R$^6$)C(O)C$_{0-6}$alkyl-N(R$^6$)R$^7$, and —N(R$^6$)CO$_2$R$^7$.

In another example, the compound is according to paragraph [0063], wherein said at least one of R$^2$ is ortho to the nitrogen of the pyridine ring bearing R$^2$.

In another example, the compound is according to paragraph [0047], selected from N-cyclopentyl-2-naphthalen-1-yl-N-[2-(5-pyridin-4-yl-1H-1,2,4-triazol-3-yl)ethyl]acetamide, N-cyclopentyl-2-naphthalen-1-yl-N-[2-(3-pyridin-4-yl-1,2,4-oxadiazol-5-yl)ethyl]acetamide, and N-cyclopentyl-N-(2-{4-[4-(methyloxy)phenyl]-2-pyridin-4-yl-1H-imidazol-5-yl}ethyl)-2-naphthalen-1-ylacetamide.

Another aspect of the invention is a pharmaceutical composition comprising a compound according to any one of paragraphs [0047]-[0065] and a pharmaceutically acceptable carrier.

Another aspect of the invention is a metabolite of the compound or the pharmaceutical composition according to any one of paragraphs [0047]-[0066].

Another aspect of the invention is a method of treating a kinase-dependent disease or condition comprising administering to a mammal in need of such treatment a therapeutically effective amount of the compound or the pharmaceutical composition according to any one of paragraphs [0047]-[0066].

Another aspect of the invention is a method of modulating the in vivo activity of a kinase, the method comprising administering to a subject an effective amount of the compound or the pharmaceutical composition according to any one of paragraphs [0047]-[0066].

Another aspect of the invention is the method according to paragraph [0069], wherein the kinase is Tie-2.

Another aspect of the invention is the method according to paragraph [0070], wherein modulating the in vivo activity of Tie-2 comprises inhibition of Tie-2.

Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition according to any one of paragraphs [0047]-[0066].

Another aspect of the invention is a method of screening for a modulator of Tie-2, the method comprising combining either the compound or the pharmaceutical composition according to any one of paragraphs [0047]-[0066] and at least one candidate agent and determining the effect of the candidate agent on the activity of Tie-2.

Another aspect of the invention is a method of inhibiting proliferative activity in a cell, the method comprising administering an effective amount of the compound according to any of paragraphs [0047]-[0065] to a cell or a plurality of cells.

Definitions

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "⁓" symbol will be used at the end of the bond which was theoretically cleaved in order to separate the group from its parent structural formula.

Chemical formulae use descriptors such as "R¹" accompanied by a list of formulae or verbage describing the scope of what is meant by the descriptor. A subsequent descriptor such as "R^{1a}" is used to describe some subset of the scope of R¹, and "R^{1b}" is used to describe another subset of the scope of R¹, and so on. In such subsequent cases, all other formulae containing simply "R¹" are meant to include the entire scope of the descriptor.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

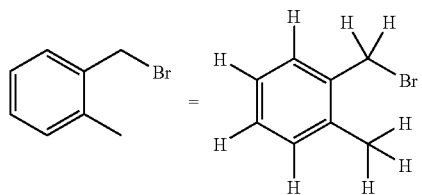

In this application, some ring structures are depicted generically and will be described textually. For example, in the schematic-below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

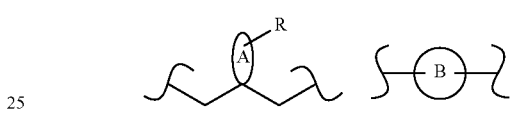

If a group "R" is depicted as "floating" on a ring system, as for example in the formula:

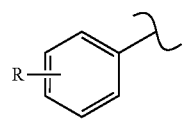

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

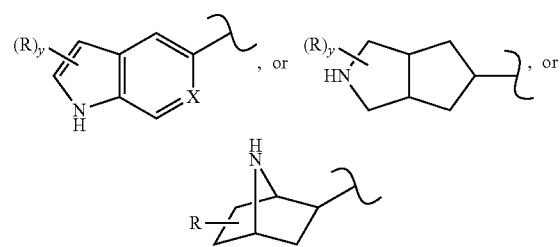

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

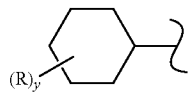

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

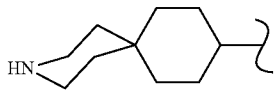

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl ($C_{1-6}$ alkyl) refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl. Otherwise, if alkenyl and/or alkynyl descriptors are used in a particular definition of a group, for example "$C_4$ alkyl" along "$C_4$ alkenyl," then $C_4$alkenyl geometric isomers are not meant to be included in "$C_4$ alkyl," but other 4-carbon isomers are, for example $C_4$ alkynyl. For example, a more general description, intending to encompass the invention as a whole may describe a particular group as "$C_{1-8}$ alkyl" while a preferred species may describe the same group as including, "$C_{1-8}$ alkyl," "$C_{1-6}$ alkenyl" and "$C_{1-5}$ alkynyl."

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene ($—CH_2CH_2—$), propylene ($—CH_2CH_2CH_2—$), dimethylpropylene ($—CH_2C(CH_3)_2CH_2—$), and cyclohexylpropylene ($—CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as C$_{1-6}$ arylalkyl.

"Exo-alkenyl" refers to a double bond that emanates from an annular carbon, and is not within the ring system, for example the double bond depicted in the formula below.

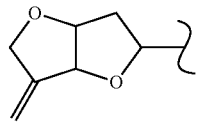

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl$C_{1-8}$alkyl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

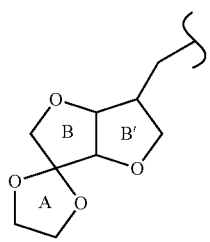

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl, hydroxypropyl, nitromethyl, aminoethyl and the like), optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—$CO_2H$), optionally substituted carboalkoxy (that is, acyloxy or —OC(=O)R), optionally substituted carboxyalkyl (that is, esters or —$CO_2R$), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, oxo, carbamyl, optionally substituted acylamino, optionally substituted hydrazino, optionally substituted hydroxylamino, and optionally substituted sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH₂—" is meant to mean not only "—OCH₂—" as drawn, but also "—CH₂O—," unless the limitation is stated explicitly.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one of ordinary skill in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration; the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

Utility of Compounds of the Invention as Screening Agents

To employ the compounds of the invention in a method of screening for candidate agents that bind to, for example a Tie-2 receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, a Tie-2 protein may be done in a number of ways. In one example, the candidate agent (the compound of the invention) is labeled, for example, with a fluorescent or radioactive moiety and binding determined directly. For example, thus may be done by attaching all or a portion of the Tie-2 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, a Tie-2 protein may be labeled at tyrosine positions using $^{125}I$, or with fluorophores. Alternatively, more than one component may be labeled with different labels; using $^{125}I$ for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to Tie-2's.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to Tie-2's, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to a Tie-2 for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to a Tie-2 and thus is capable of binding to, and potentially modulating, the activity of the Tie-2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to a Tie-2 with a higher affinity. Thus, if the candidate agent is labeled, the presence of the label on the support, coupled with a lack of competitor binding, may indicate the candidate agent is capable of binding to a Tie-2.

It may be of value to identify the binding site of a Tie-2. This can be done in a variety of ways. In one embodiment, once a Tie-2 has been identified as binding to the candidate agent, the Tie-2 is fragmented or modified and the assays repeated to identify the necessary components for binding.

Modulation is tested by screening for candidate agents capable of modulating the activity of Tie-2's comprising the steps of combining a candidate agent with a Tie-2, as above, and determining an alteration in the biological activity of the Tie-2. Thus, in this embodiment, the candidate agent should both bind to (although this may not be necessary), and alter its biological or biochemical activity as defined herein. The methods include both if: vitro screening methods and in vivo screening of cells for alterations in cell viability, morphorlogy, and the like.

Alternatively, differential screening may be used to identify drug candidates that bind to native Tie-2's, but cannot bind to modified Tie-2's.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Abbreviations and their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ene |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |

| Abbreviation | Meaning |
| --- | --- |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |

Synthesis of Compounds

Schemes 1-4 depict general synthetic routes for compounds of the invention and are not intended to be limiting. Specific examples are described subsequently to these general synthetic descriptions. In the generalizations below, specific reaction conditions, for example, added bases, acids, solvents, temperature, and the like are not described so as not to complicate the discussion. The general routes, in conjunction with the specific examples, contain sufficient information to allow one of ordinary skill in the art to synthesize compounds of the invention. In Schemes 1-4, some substituents (e.g. -L-X-Z, Y, $R^1$, and $R^2$) are not described as reactive partners in the synthesis of compounds of the invention. This is done purely for descriptive simplification. Such substituents in Formula I may or may not be reactive partners in particular synthetic schemes described herein as would be understood by one of ordinary skill in the art. Thus, such substituents may be appended to the scaffold of Formula I at any time during synthesis or may pre-exist on intermediates or starting materials used to make compounds of the invention, as would be understood by one of ordinary skill in the art. More specific examples are presented below to more fully describe the invention.

Scheme 1 depicts an example of how certain triazole regioisomers, consistent with Formula I, are made. Hydrazide (i) and amidine (ii) (or a corresponding nitrile) are combined under heat and pressure, for example, to afford compounds (iii). In this example, -L-X-Z is generally attached after formation (i.e. combining (i) and (ii) as described) of the triazole ring system. Thus (iii) is typically, but not necessarily, made as a regioisomeric mixture (having -L-X-Z attached via trapping out one of the triazole tautomeric forms) and the resultant regioisomers isolated subsequently.

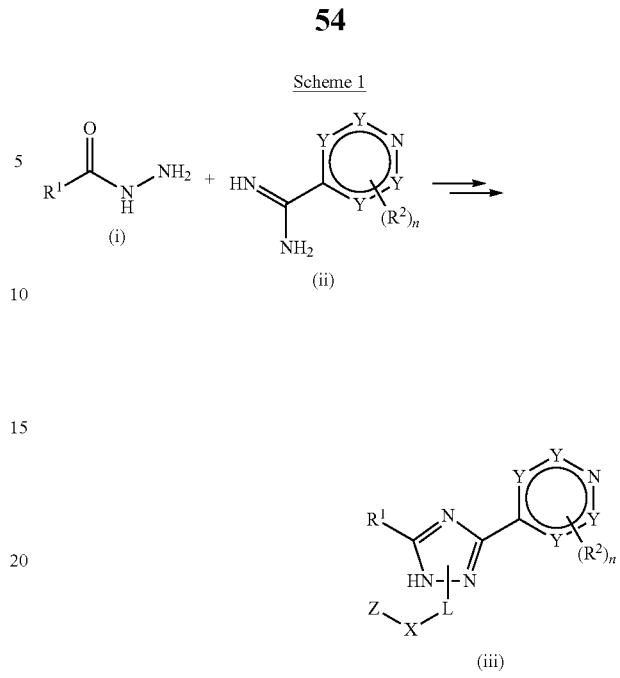

Scheme 2 depicts one method to synthesize triazole regioisomers having -L-X-Z bound to a carbon of the triazole, rather than a nitrogen of the triazole, as in Scheme 1. In this example, nitrile (iv) is combined with hydrazide (v) to ultimately give compounds (vi). Analogous to the above example, (vi) is typically but not necessarily, made as a regioisomeric mixture (having —$R^1$ attached via trapping out one of the triazole tautomeric forms) and the resultant regioisomers isolated subsequently.

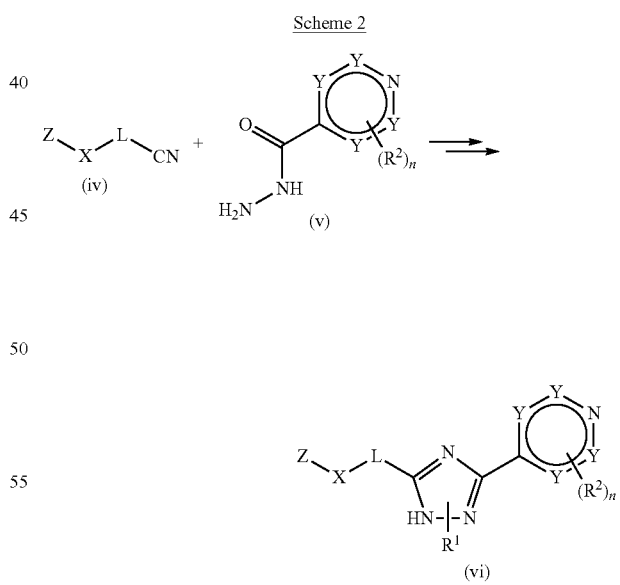

Scheme 3 depicts how regioisomeric oxadiazoles, (ix) and (xii), according to Formula I of the invention are made, respectively. For example, carboxylic acid (vii) is coupled to oxime (viii) and the resultant aldoxime cyclized to give compounds (ix). In another example, carboxylic acid (xi) is coupled to oxime (x) and the resultant aldoxime cyclized to give compounds (xii).

Scheme 3

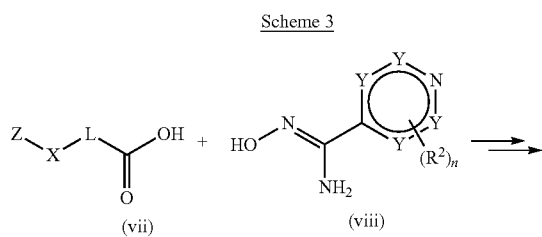

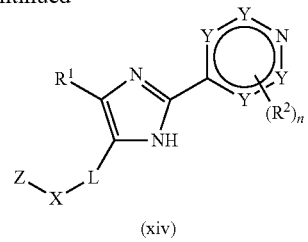

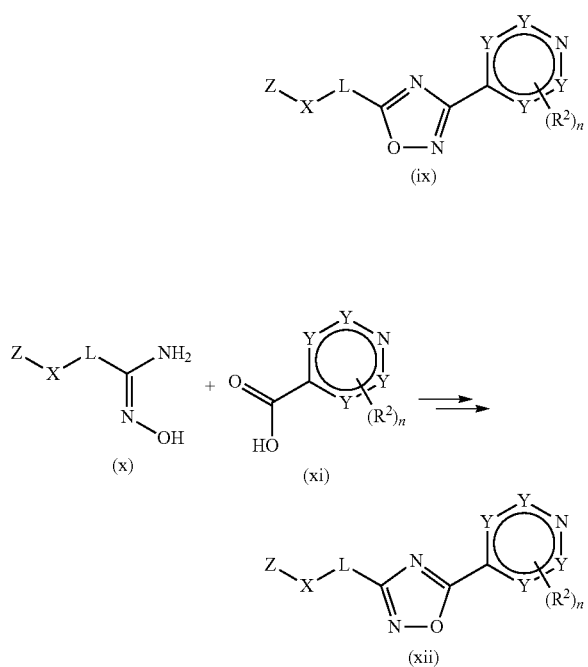

Scheme 4 depicts synthesis of imidazoles of the invention. Diketone (xiii) is combined with amidine (ii) to give imidazole (xiv). For example, diketones (xiii) were obtained via RuO$_4$ oxidation of a corresponding propargyl derivative. Again, Scheme 4 is illustrative of the general synthetic procedure. Generally, but not necessarily, -L-X-Z is installed into the molecule after combination of (xiii) and (ii) to make (xiv). For example, Sonogashira addition of homopropargyl alcohol to 2-chloro-4-iodoanisole followed by RuO$_4$ oxidation of the corresponding aryl propargyl alcohol derivative gave the corresponding 1,2-diketone. The imidazole was then made by cyclization of the 1,2-diketone with a 4-amidinopyridine, for example. The alcohol functionality (ultimately from the propargyl alcohol intermediate) appended to the imidazole was subsequently transformed into -L-X-Z.

Scheme 4

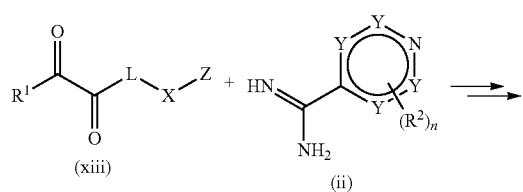

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example is set out below as a multi-step synthesis. In some instances, following specific examples are lists of compounds that were made in a similar way.

Example 1

Ethyl[5-(3,5-dichlorophenyl)-3-pyridin-4-yl-1H-1,2,4-triazol-1-yl]acetate: Iso-nicotinic hydrazide (1.0 g, 7.3 mmol), 3,5-dichlorobenzonitrile (1.5 g, 8.8 mmol), and sodium ethoxide (1.5 g, 22 mmol) were transferred to a pressure tube. Ethanol (4 mL) was added and the reaction was stirred at 120° C. overnight. The reaction was monitored by LCMS. Upon completion, the ethanol was removed in vacuo to afford the triazole as a solid and carried on to the next step without purification. This material was dissolved in DMF (10 mL), and potassium carbonate (1.5 g, 11 mmol) and ethyl bromoacetate (1.2 mL, 11 mmol) were added. The reaction was stirred at room temperature overnight. The reaction was monitored by LCMS. Upon completion, the reaction mixture was diluted with water. The precipitate was collected via vacuum filtration and the filtrate was discarded. The crude product was purified by silica gel chromatography (3:2 hexanes/ethyl acetate) to afford two regioisomers as solids. $^1$H NMR (400 MHz, d$_6$-DMSO): δ 8.7 (d, 21, 7.95 (s, 2H), 7.9 (d, 1H), 7.8 (d, 2H), 5.5 (s, 2H), 4.1 (q, 2H), 1.1 (t, 3H). MS (EI) for C$_{17}$H$_{14}$N$_4$O$_2$Cl$_2$: 377 (MH$^+$). Ethyl[3-(3,5-dichlorophenyl)-5-pyridin-4-yl-1H-1,2,4-triazol-1-yl]acetate: $^1$H NMR (400 MHz, d$_6$-DMSO): δ 8.8 (d, 2H), 8.0 (s, 2H), 7.8 (m, 3H), 5.5 (s, 2H), 4.1 (q, 2H), 1.2 (t, 3H). MS (EI) for C$_{17}$H$_{14}$N$_4$O$_2$Cl$_2$: 377 (MH$^+$).

2-{5-[3-Chloro-4-(methyloxy)phenyl]-3-pyridin-4-yl-1H-1,2,4-triazol-1-yl}-N-cyclopentylacetamide: A mixture of ethyl {5-[3-chloro-4-(methyloxy)phenyl]-3-pyridin-4-yl-1H-1,2,4-triazol-1-yl}acetate (0.2 mmol) and cyclopentylamine (4 mL) were heated to reflux for 2 h. The mixture was cooled to room temperature and the excess cyclopentylamine was removed in vacuo. The crude solid was then triturated with methanol to afford the pure product (0.061 g, 75%). $^1$H NMR (400 MHz, d$_6$-DMSO): δ 8.68 (dd, 2H), 7.92 (22, 2H), 7.82 (m, 1H), 7.75 (dd, 1H), 7.33 (d, 1H), 4.95 (s, 2H), 4.00 (m, 1H), 3.94 (s, 3H), 1.80 (m, 2H), 1.64 (m, 2H), 1.51 (m, 2H), 1.40 (m, 2H). MS (EI) for C$_{21}$H$_{23}$ClN$_5$O$_2$: 412 (MH$^+$).

N-(2-{5-[3-Chloro-4-(methyloxy)phenyl]-3-pyridin-4-yl-1H-1,2,4-triazol-1-yl}ethyl)-N-cyclopentyl-2-naphthalen-1-ylacetamide: A solution of 2-{5-[3-chloro-4-(methyloxy)

phenyl]-3-pyridin-4-yl-1H-1,2,4-triazol-1-yl}-N-cyclopentylacetamide (1.11 g, 2.69 mmol) in THF (34 mL) was stirred under nitrogen and borane-THF complex (10.8 mL, 1 M solution in THF, 10.8 mmol) and boron trifluoride etherate (0.34 mL, 2.69 mmol) were added. The reaction mixture was heated to reflux for 12 h. An aqueous solution of hydrochloric acid (1 M, 20 mL) was added and the heterogeneous mixture was stirred vigorously for 1 h. The mixture was made basic (pH >8) with 5N aqueous sodium hydroxide and extracted with ethyl acetate (3×). The combined organic layers were washed with brine, dried over sodium sulfate, filtered and concentrated in vacuo. The crude material was purified by silica gel chromatography (1:3:96 triethylamine/methanol/dichloromethane) to afford the secondary amine as a viscous oil (0.91 g, 85%). The secondary amine (0.88 g, 2.2 mmol) was added to a stirring solution of HATU (0.93 g, 2.4 mmol), 1-naphthylacetic acid (0.41 g, 2.2 mmol) and diisopropylethylamine (0.77 mL, 4.4 mmol) in DMF (6 mL). The mixture was stirred at room temperature for 3 h. Aqueous LiCl (5%) was added and the mixture was extracted with ethyl acetate (3×). The combined organic layers were washed with brine, dried over sodium sulfate, filtered and concentrated in vacuo. The crude product was purified by silica gel chromatography (5:95 methanol/dichloromethane) to afford pure product (0.60 g, 48%). $^1$H NMR (400 MHz, $d_6$-DMSO) 2:1 mixture of amide rotamers: δ 8.68 (d, 2H), 7.94-7.72 (m, 6H), 7.49-7.21 (m, 6H), 4.50 (m, 1H), 4.35 (t, 2H), 4.29 (t, 1H), 4.12 (s, 1H), 3.94 (s, 3H), 3.8.6 (m, 1H), 3.56 (t, 1H), 1.60 (m, 2H), 1.51 (m, 2H), 1.39 (m, 2H), 1.24 (m, 2H). MS (EI) for $C_{33}H_{33}ClN_5O_2$: 566 (MH$^+$).

N-Cyclopentyl-N-[2-(5-furan-2-yl-3-pyridin-4-yl-1H-1,2,4-triazol-1-yl)ethyl]-2-naphthalen-1-ylacetamide: A slurry of 4-(5-furan-2-yl-1H-1,2,4-triazol-3-yl)pyridine (740 mg, 3.5 mmol), 2-iodoethanol (2.0 g, 12 mmol), and cesium carbonate (3.4 g, 3.4 mmol) were slurried in DMF (15 mL) and heated at 85° C. for 12 h. The reaction mixture was cooled to room temperature and neutralized to pH 7 with 5% citric acid. The mixture was extracted with ethyl acetate (3×) and the combined organic layers were then extracted with 5% LiCl (2×) and brine, dried over sodium sulfate, filtered, and concentrated in vacuo to afford the corresponding alcohol (0.82 mg, 91%). This material was dissolved in dichloromethane (30 mL) and triethylamine (2.2 mL). Methanesulfonic anhydride (2.8 g, 16 mmol) was added dropwise and the reaction mixture was stirred for 4 h. The mixture was concentrated in vacuo, redissolved in ethyl acetate, and washed with saturated, aqueous sodium bicarbonate. The ethyl acetate phase was dried over sodium sulfate, filtered, and concentrated in vacuo to afford the mesylate (0.65 g, 65%). A solution of the mesylate, cyclopentylamine (0.3 mL, 3 mmol) and 2,6-lutidine (0.4 mL, 3.3 mmol) in DMF (15 mL) was heated to 80° C. for 18 h. The mixture was cooled to room temperature, diluted with 5% LiCl and extracted with ethyl acetate (3×). The combined organic layers were washed with brine, dried over sodium sulfate, filtered and concentrated in vacuo to afford the amine (0.33 g, 54%). The amine was added to a stirring solution of HATU (0.46 g, 1.2 mmol), 1-naphthylacetic acid (0.21 g, 1.1 mmol) and diisopropylethylamine (0.39 mL, 2.2 mmol) in DMF (5 mL). The mixture was stirred at room temperature for 3 h. Aqueous LiCl (5%) was added and the mixture was extracted with ethyl acetate (3×). The combined organic layers were washed with brine, dried over sodium sulfate, filtered and concentrated in vacuo. The crude product was purified by preparative HPLC to afford pure product (0.15 g, 28%). $^1$H NMR (400 MHz, $d_6$-DMSO): δ 8.82 (d, 2H), 8.18 (d, 2H), 8.0 (d, 1H), 7.86-7.78 (m, 3H), 7.5-7.26 (m, 5H), 6.8 (m, 1H), 4.8-4.68 (tt, 2H), 4.35 (m, 1H), 4.2 (s, 2H), 3.65 (t, 2H), 1.7-1.35 (m, 8H). MS (EI) for $C_{30}H_{29}N_5O_2$: 492 (MH$^+$).

Using analogous synthetic technique, substituting with the appropriate reagents, such as the respective amines, the following compounds of the invention were prepared:

N-{2-[5-(3-Chloro-4-hydroxyphenyl)-3-pyridin-4-yl-1H-1,2,4-triazol-1-yl]ethyl}-N-cyclopentyl-2-naphthalen-1-ylacetamide: $^1$H NMR (400 MHz, $d_6$-DMSO): δ 10.94 (s, 1H), 8.70 (d, 2H), 7.96-7.77 (m, 6H), 7.60 (dd, 1H), 7.50 (m, 2H), 7.42 (m 1H), 7.25 (d, 1H), 7.13 (d, 1H), 4.50 (m, 2H), 4.30 (m, 0.5H), 4.14 (s, 2H), 3.87 (m, 0.5H), 3.54 (t, 2H), 1.60 (m, 2H), 1.51 (m, 2H), 1.39 (m, 2H), 1.24 (m, 2H). MS (EI) for $C_{32}H_{31}ClN_5O_2$: 552 (MH$^+$).

Ethyl{5-[3-chloro-4-(methyloxy)phenyl]-3-pyridin-4-yl-1H-1,2,4-triazol-1-yl}acetate: $^1$H NMR (400 MHz, $d_6$-DMSO): δ 8.69 (m, 2H), 7.94 (m, 2H), 7.80 (m, 1H), 7.69 (dd, 1H), 7.34 (d, 1H), 5.36 (s, 2H), 4.13 (q, 2H), 3.94 (s, 3H), 1.16 (t, 3H). MS (EI) for $C_{18}H_{18}ClN_4O_3$: 373 (MH$^+$).

Ethyl{3-[3-chloro-4-(methyloxy)phenyl]-5-pyridin-4-yl-1H-1,2,4-triazol-1-yl}acetate: $^1$H NMR (400 MHz, $d_6$-DMSO): δ 8.76-8.79 (m, 2H), 7.95-8.00 (m, 2H), 7.76-7.78 (m, 2H), 7.26-7.29 (m, 1H), 5.40 (s, 2H), 4.13-4.15 (m, 2H), 3.92 (s, 3H), 1.15 (t, 3H). MS (EI) for $C_{18}H_{17}ClN_4O_3$: 373 (MH$^+$).

2-{3-[3-Chloro-4-(methyloxy)phenyl]-5-pyridin-4-yl-1H-1,2,4-triazol-1-yl}-N-cyclopentylacetamide: $^1$H NMR (400 MHz, $d_6$-DMSO): δ 8.72-8.77 (m, 2H), 8.38-8.42 (m, 1H), 7.95-8.00 (m, 1H), 7.75-7.78 (m, 2H), 7.22-7.24 (m, 1H), 5.02 (s, 2H), 3.90-3.98 (m, 1H), 3.88 (s, 3H), 1.31-1.83 (m, 8H). MS (EI) for $C_{21}H_{22}ClN_5O_2$: 412 (MH$^+$).

Methyl3-{5-[3-chloro-4-(methyloxy)phenyl]-3-pyridin-4-yl-1H-1,2,4-triazol-1-yl}propanoate: $^1$H NMR (400 MHz, $d_6$-DMSO): δ 8.83 (d, 2H), 8.20 (d, 2H), 7.89 (d, 1H), 7.78 (dd, 1H), 7.36 (d, 1H), 4.53 (t, 2H), 3.95 (s, 3H), 3.55 (s, 3H), 3.05 (t, 2H). MS (EI) for $C_{18}H_{17}ClN_4O_3$: 373 (MH$^+$).

Methyl3-{3-[3-chloro-4-(methyloxy)phenyl]-5-pyridin-4-yl-1H-1,2,4-triazol-1-yl}propanoate: $^1$H NMR (400 MHz, $d_6$-DMSO): δ 8.82 (d, 2H), 7.97 (d, 1H), 7.94 (dd, 1H), 7.88-7.87 (m, 2H), 7.26 (d, 1H), 4.52 (t, 2H), 3.91 (s, 3H), 3.54 (s, 3H), 3.04 (t, 2H). MS (EI) for $C_{18}H_{17}ClN_4O_3$: 373 (MH$^+$).

N-(3-{5-[3-Chloro-4-(methyloxy)phenyl]-3-pyridin-4-yl-1H-1,2,4-triazol-1-yl}propyl)-N-cyclopentyl-2-naphthalen-1-ylacetamide: $^1$H NMR (400 MHz, $d_6$-DMSO): δ 8.87-8.60 (m, 2H), 8.36-8.03 (m, 2H), 7.88-7.63 (m, 5H), 7.42-7.21 (m, 5H), 4.26 (t, 2H), 4.22-4.14 (m, 1H), 4.10 (s, 2H), 3.87 (s, 3H), 3.10-3.07 (m, 2H), 2.02 (t, 2H), 1.76-1.31 (m, 8H). MS (EI) for $C_{34}H_{34}ClN_5O_2$: 581 (MH$^+$).

N-(3-{3-[3-Chloro-4-(methyloxy)phenyl]-5-pyridin-4-yl-1H-1,2,4-triazol-1-yl}propyl)-N-cyclopentyl-2-naphthalen-1-ylacetamide: $^1$H NMR (400 MHz, $d_6$-DMSO): δ 8.75-8.72 (m, 2H), 7.93-7.88 (m, 1H), 7.88-7.77 (m, 5H), 7.73-7.69 (m, 1H), 7.43-7.19 (m, 5H), 4.28 (t, 2H), 4.24-4.20 (m, 1H), 4.10 (s, 2H), 3.84 (s, 3H), 3.12-3.08 (m, 2H), 2.08-2.00 (m, 2H), 1.61-1.33 (m, 8H). MS (EI) for $C_{34}H_{34}ClN_5O_2$: 581 (MH$^+$).

N-(2-{3-[3-Chloro-4-hydroxyphenyl]-5-pyridin-4-yl-1H-1,2,4-triazol-1-yl}ethyl)-N-cyclopentyl-2-naphthalen-1-ylacetamide: $^1$H NMR (400 MHz, $d_6$-DMSO): δ 10.62 (s, 1H), 8.8 (d, 2H), 7.95-7.7 (m, 7H), 7.5-7.3 (m, 3H), 7.22 (d, 1H), 7.05 (d, 1H), 4.5 (t, 2H), 4.25 (t, 1H), 4.1 (s, 2H), 3.6 (t, 2H), 1.65-1.2 (m, 8H). MS (EI) for $C_{32}H_{30}ClN_5O_2$: 552 (MH$^+$).

2-{3-[3-Chloro-4-(methyloxy)phenyl]-5-pyridin-3-yl-1H-1,2,4-triazol-1-yl}-N-cyclopentylacetamide: $^1$H NMR (400, $d_6$-DMSO): δ 9.0 (s, 1H), 8.8 (s, 1H), 8.45 (d, 1H), 8.3 (d, 1H), 8.0 (s, 1H), 7.96 (d, 1H), 7.65 (d, 1H), 7.25 (d, 1H), 4.95 (s, 2H), 3.95 (m, 1H), 3.9 (s, 3H), 1.85-1.3 (m, 8H). MS (EI) for $C_{21}H_{22}ClN_5O_2$: 412 (MH$^+$).

N-(2-{5-[3-Chloro-4-(methyloxy)phenyl]-3-pyridin-3-yl-1H-1,2,4-triazol-1-yl}ethyl)-N-cyclopentyl-2-naphthalen-1-ylacetamide: $^1$H NMR (400 MHz, d$_6$-DMSO): δ 9.2 (s, 1H), 8.62 (s, 1H), 8.34 (d, 1H), 7.9-7.7 (m, 5H), 7.95-7.2 (m, 6H), 4.45 (t, 2H), 4.3 (m, 1H), 4.1 (s, 2H), 3.93 (s, 3H), 3.6 (t, 2H), 1.65-1.2 (m, 8H). MS (EI) for $C_{33}H_{32}ClN_5O_2$: 566 (MH$^+$).

Ethyl[5-(4-nitrophenyl)-3-pyridin-4-yl-1H-1,2,4-triazol-1-yl]acetate: $^1$H NMR (400 MHz, d$_6$-DMSO): δ 8.8 (d, 2H), 8.4 (d, 2H), 8.05 (d, 2H), 8.0 (d, 2H), 5.5 (s, 2H), 4.04 (q, 2H), 1.1 (t, 3H). MS (E) for $C_{17}H_{15}N_5O_4$: 354 (MH$^+$).

N-Cyclopentyl-N-[2-(3-furan-2-yl-5-pyridin-4-yl-1H-1,2,4-triazol-1-yl)ethyl]-2-naphthalen-1-ylacetamide: $^1$H NMR (400 MHz, d$_6$-DMSO): δ 8.8 (d, 2H), 7.9-7.78 (m, 6H), 7.48 (m, 2H), 7.38 (m, 1H), 7.22 (d, 1H), 7.0 (d, 1H), 6.65 (m, 1H), 4.6-4.5 (t, 2H), 4.3 (m, 1H), 4.1 (s, 2H), 3.58 (t, 2H), 1.65-1.25 (m, 8H). MS (EI) for $C_{30}H_{29}N_5O_2$: 492 (MH$^+$).

N-Cyclopentyl-2-naphthalen-1-yl-N-{2-[5-pyridin-4-yl-3-(2-thienyl)-1H-1,2,4-triazol-1-yl]ethyl}acetamide: $^1$H NMR (400 MHz, d$_6$-DMSO): δ 8.75 (d, 2H), 7.9-7.75 (m, 5H), 7.65 (m, 2H), 7.5-7.35 (m, 4H), 7.22 (d, 1H), 7.18 (t, 1H), 4.55-4.45 (m, 2H), 4.3 (m, 1H), 3.55 (t, 2H), 1.6-1.2 (m, 8H). MS (EI) for $C_{30}H_{29}N_5OS$: 508 (MH$^+$).

N-(2-{5-[3-Chloro-4-(methyloxy)phenyl]-3-pyridin-4-yl-1H-1,2,4-triazol-1-yl}ethyl)-N-cyclopentylnaphthalene-1-carboxamide: $^1$H NMR (400 MHz, d$_6$-DMSO) 1:1 mixture of 2 isomers: δ 8.82 (m, 4H), 8.22 (m, 4H), 7.97 (d, 2H), 7.92-7.86 (m, 6H), 7.58 (d, 2H), 7.51-7.40 (m, 6H), 7.35 (d, 2H), 7.16-7.14 (d, 2H), 4.81-4.70 (m, 4H), 4.36 (d, 2H), 3.87 (s, 3H), 3.86 (s, 3H), 3.59-3.50 (m, 4H), 1.46-1.16 (m, 12H), 1.13-1.05 (m, 4H). MS (EI) for $C_{32}H_{30}ClN_5O_2$: 552 (MH$^+$).

N-(2-{5-[3-Chloro-4-(methyloxy)phenyl]-3-pyridin-4-yl-1H-1,2,4-triazol-1-yl}ethyl)-N-cyclopentylnaphthalene-2-carboxamide: $^1$H NMR (400 MHz, d$_6$-DMSO) 1:1 mixture of 2 isomers: δ 8.80-8.75 (m, 4H), 8.27-8.14 (m, 4H), 7.96-7.81 (m, 10H), 7.65-7.59 (m, 2H), 7.53-7.50 (m, 4H), 7.30 (m, 2H), 7.22-7.20 (m, 2H), 4.83-4.80 (m, 4H), 4.69-4.65 (m, 2H), 3.86 (s, 3H), 3.74 (s, 3H), 3.71 (m, 4H), 1.51-1.41 (m, 8H), 1.20 (m, 8H). MS (EI) for $C_{32}H_{30}ClN_5O_2$: 552 (MH$^+$).

N-Cyclopentyl-N-(2-{5-[3-(methyloxy)phenyl]-3-pyridin-4-yl-1H-1,2,4-triazol-1-yl}ethyl)-2-naphthalen-1-ylacetamide: $^1$H NMR (400 MHz, d$_6$-DMSO): δ 8.85-8.78 (dd, 2H), 8.2-8.1 (m, 2H), 7.9-7.8 (m, 3H), 7.5-7.2 (m, 8H), 4.6-4.5 (t, 2H), 4.3 (m, 1H), 4.15 (s, 2H), 3.85 (s, 3H), 3.55 (t, 2H), 1.65-1.15 (m, 8H). MS (EI) for $C_{33}H_{33}N_5O_2$: 532 (MH$^+$).

N-Cyclopentyl-N-(2-{3-[3-(methyloxy)phenyl]-5-pyridin-4-yl-1H-1,2,4-triazol-1-yl}ethyl)-2-naphthalen-1-ylacetamide: $^1$H NMR (400 MHz, d$_6$-DMSO): δ 8.85 (d, 2H), 7.96-7.76 (m, 5H), 7.68-7.58 (m, 2H), 7.55-7.32 (m, 4H), 7.24 (d, 1H), 7.05 (m, 1H), 4.6-4.5 (m, 2H), 4.4 (m, 1H), 4.1 (s, 2H), 3.85 (s, 3H), 3.6 (t, 2H), and 1.65-1.2 (m 8H). MS (EI) for $C_{33}H_{33}N_5O_2$: 532 (MH$^+$).

N-(4-{5-[3-Chloro-4-(methyloxy)phenyl]-3-pyridin-4-yl-1H-1,2,4-triazol-1-yl}butyl)-N-cyclopentyl-2-naphthalen-1-ylacetamide: $^1$H NMR (400 MHz, d$_6$-DMSO): δ 8.75-8.65 (m, 2H), 8.08-7.99 (m, 2H), 7.85-7.65 (m, 5H), 7.43-7.17 (m, 5H), 4.30-4.25 (m, 2H), 4.21-4.15 (m, 1H), 4.09 (s, 2H), 3.89 (s, 3H), 3.02 (t, 2H), 1.76-1.73 (m, 4H), 1.57-1.33 (m, 8H). MS (EI) for $C_{35}H_{36}ClN_5O_2$: 595 (MH$^+$).

N-(4-{3-[3-Chloro-4-(methyloxy)phenyl]-5-pyridin-4-yl-1H-1,2,4-triazol-1-yl}butyl)-N-cyclopentyl-2-naphthalen-1-ylacetamide: $^1$H NMR (400 MHz, d$_6$-DMSO): δ 8.77-8.74 (m, 2H), 7.96-7.95 (m, 1H), 7.93-7.90 (m, 1H), 7.87-7.80 (m, 2H), 7.78-7.77 (m, 1H), 7.74-7.71 (m, 2H), 7.43-7.31 (m, 3H), 7.23-7.19 (m, 2H), 4.32-4.26 (m, 2H), 4.18-4.14 (m, 1H), 4.09 (s, 2H), 3.86 (s, 3H), 3.10-3.01 (m, 2H), 1.78-1.73 (m, 4H), 1.55-1.34 (m, 8H). MS (EI) for $C_{35}H_{36}ClN_5O_2$: 595 (MH$^+$).

N-(2-{5-[3-Chloro-4-(methyloxy)phenyl]-3-pyridin-4-yl-1H-1,2,4-triazol-1-yl}ethyl)-N-cyclopentylbenzamide: $^1$H NMR (400 MHz, d$_6$-DMSO): δ 8.79 (m, 2H), 8.12 (m, 2H), 8.00-7.93 (m, 1H), 7.85 (m, 1H), 7.40-731 (m, 4H), 7.16-7.12 (m, 2H), 4.65-4.52 (m, 2H), 3.95 (s, 3H), 3.84 (m, 1H), 3.70 (t, 2H), 1.51-1.49 (m, 4H), 1.27-1.51 (m, 4H). MS (EI) for $C_{28}H_{28}ClN_5O_2$: 502 (MH$^+$).

N-(2-{3-[3-Chloro-4-(methyloxy)phenyl]-5-pyridin-4-yl-1H-1,2,4-triazol-1-yl}ethyl)-N-cyclopentylbenzamide: $^1$H NMR (400 MHz, d$_6$-DMSO): δ 8.73 (d, 2H), 7.95-7.91 (m, 2H), 7.85-7.84 (m, 2H), 7.31-7.29 (m, 3H), 7.22 (d, 1H), 7.06 (d, 2H), 4.60 (m, 2H), 3.86 (s, 3H), 3.76 (m, 1H), 3.63 (t, 2H), 1.42 (m, 4H), 1.22-1.19 (m, 4H). MS (EI) for $C_{28}H_{28}ClN_5O_2$: 502 (MH$^+$).

N-(2-{5-[3-Chloro-4-(methyloxy)phenyl]-3-pyridin-4-yl-1H-1,2,4-triazol-1-yl}ethyl)-N-cyclopentylquinoline-4-carboxamide: $^1$H NMR (400 MHz, d$_6$-DMSO) mixture of 2 isomers: δ 8.99-8.98 (d, 2H), 8.93-8.91 (m, 2H), 8.81-8.80 (m, 2H), 8.16-8.08 (m, 6H), 8.04-8.02 (m, 2H), 7.90-7.82 (m, 3H), 7.82-7.75 (m, 3H), 7.66-7.61 (m, 2H), 7.45 (d, 1H), 7.40 (d, 1H), 7.36-7.34 (m, 2H), 4.91-4.84 (m, 4H), 4.03 (s, 3H), 4.01 (s, 3H), 3.99-3.91 (m, 4H), 3.64-3.42 (m, 2H), 1.89-1.82 (m, 2H), 1.62 (m, 2H), 1.50-1.40 (m, 8H), 1.39-1.20 (m, 4H). MS (EI) for $C_{31}H_{29}ClN_6O_2$: 553 (MH$^+$).

N-(2-{5-[3-Chloro-4-(methyloxy)phenyl]-3-pyridin-4-yl-1H-1,2,4-triazol-1-yl}ethyl)-N-cyclopentyl-N'-naphthalen-1-ylurea: $^1$H NMR (400 MHz, d$_6$-DMSO) mixture of 2 isomers: δ 8.68-8.62 (m, 4H), 8.42 (m, 2H), 7.97-7.74 (m, 10H), 7.72-7.33 (m, 10H), 7.23-7.13 (m, 4H), 4.50-4.45 (m, 4H), 4.29-4.23 (m, 2H), 3.86 (s, 3H), 3.82 (s, 3H), 3.63 (m, 4H), 1.69-1.23 (m, 16H). MS (EI) for $C_{32}H_{31}ClN_6O_2$: 567 (MH$^+$).

N-(2-{5-[3-Chloro-4-(methyloxy)phenyl]-3-pyridin-4-yl-1H-1,2,4-triazol-1-yl}ethyl)-N-cyclopentyl-N'-phenylurea: $^1$H NMR (400 MHz, d$_6$-DMSO) mixture of 2 isomers: δ 8.77-8.75 (m, 4H), 8.34-8.32 (m, 4H), 8.08-8.01 (m, 4H), 7.90-7.74 (m, 4H), 7.39-7.34 (m, 5H), 7.28-7.23 (m, 5H), 7.02-6.97 (m, 2H), 4.56 (t, 4H), 4.29-4.04 (m, 2H), 3.99 (s, 3H), 3.89 (s, 3H), 3.70-3.64 (m, 4H), 1.65-1.21 (m, 16H). MS (EI) for $C_{28}H_{29}ClN_6O_2$: 517 (MH$^+$).

N-(2-{5-[3-Chloro-4-(methyloxy)phenyl]-3-pyridin-4-yl-1H-1,2,4-triazol-1-yl}ethyl)-N-cyclopentyl-2-phenylacetamide: $^1$H NMR (400 MHz, d$_6$-DMSO) mixture of 2 isomers: δ 8.77-8.67 (m, 4H), 8.00-7.92 (m, 4H), 7.85-7.72 (m, 4H), 7.30-7.16 (m, 12H), 4.50-4.43 (m, 4H), 4.16-4.12 (m, 2H), 3.95 (s, 3H), 3.91 (s, 3H), 3.65 (s, 2H), 3.61 (s, 2H), 3.52-3.49 (m, 4H), 1.56-1.11 (m, 16H). MS (EI) for $C_{29}H_{30}ClN_5O_2$: 516 (MH$^+$).

N-(2-{5-[3-Chloro-4-(methyloxy)phenyl]-3-phenyl-1H-1,2,4-triazol-1-yl}ethyl)-N-cyclopentyl-2-naphthalen-1-ylacetamide: $^1$H NMR (400 MHz, CDCl$_3$): δ 8.11-6.99 (m, 15H), 4.58 (m, 2H), 4.37-3.86 (m, 8H), 1.82-1.23 (m, 8H). MS (EI) for $C_{34}H_{33}ClN_4O_2$: 566 (MH$^+$).

N-(2-{5-[3-Chloro-4-(methyloxy)phenyl]-3-phenyl-1H-1,2,4-triazol-1-yl}ethyl)cyclopentanamine: $^1$H NMR (400 MHz, CDCl$_3$): δ 8.19-6.93 (m, 9H), 6.38 (m, 1H), 4.82 (m, 2H), 4.23 (m, 1H), 3.87 (m, 3H), 2.04-1.28 (m, 8H). MS (EI) for $C_{22}H_{24}ClN_4O_2$: 411 (MH$^+$).

N-(2-{5-[3-Chloro-4-(methyloxy)phenyl]-3-pyridin-4-yl-1H-1,2,4-triazol-1-yl}ethyl)-N-(1-methylethyl)-2-naphthalen-1-ylacetamide: $^1$H NMR (400 MHz, d$_6$-DMSO): δ 8.76-8.77 (m, 2H), 7.98-8.03 (m, 1H), 7.85-7.88 (d, 1H), 7.77-7.79 (d, 1H), 7.72-7.73 (m, 2H), 7.66-7.68 (m, 1H), 7.41-7.46 (m, 1H), 7.25-7.37 (m, 4H), 4.50-4.58 (m, 4H), 3.96 (d, 5H). MS (EI) for $C_{28}H_{24}ClN_5O_2$: 499 (MH$^+$).

N-(2-{3-[3-Chloro-4-(methyloxy)phenyl]-5-pyridin-4-yl-1H-1,2,4-triazol-1-yl}ethyl)-N-(1-methylethyl)-2-naphthalen-1-ylacetamide: $^1$H NMR (400 MHz, d$_6$-DMSO): δ 8.77-8.78 (m, 2H), 8.03-8.08 (m, 2H), 7.88-7.89 (m, 1H), 7.79-7.81 (m, 3H), 7.66-7.68 (m, 1H), 7.45-7.49 (t, 1H), 7.30-7.41 (m, 3H), 7.10-7.12 (m, 1H), 4.52-4.55 (m, 2H), 4.14 (s, 2H), 3.93 (s, 3H), 3373-3.76 (m, 2H), 2.71-2.78 (m, 1H), 0.78-0.85 (m, 6H). MS (EI) for C$_{31}$H$_{30}$ClN$_5$O$_2$: 541 (MH$^+$).

N-(2-{5-[3-Chloro-4-(methyloxy)phenyl]-3-pyridin-4-yl-1H-1,2,4-triazol-1-yl}ethyl)-N-cyclohexyl-2-naphthalen-1-ylacetamide: $^1$H NMR (400 MHz, d$_6$-DMSO): δ 8.69-8.71 (m, 2H), 7.88-7.97 (m, 5H), 7.75-7.83 (m, 2H), 7.48-7.51 (m, 2H), 7.39-7.44 (m, 1H), 7.29-7.33 (m, 2H), 4.38-4.41 (t, 2H), 4.16 (s, 2H), 3.90-3.95 (m, 4H), 3.55-3.59 (m, 2H), 1.06-1.56 (m, 10H). MS (EI) for C$_{34}$H$_{34}$ClN$_5$O$_2$: 581 (MH$^+$).

N-(2-{3-[3-Chloro-4-(methyloxy)phenyl]-5-pyridin-4-yl-1H-1,2,4-triazol-1-yl}ethyl)-N-cyclohexyl-2-naphthalen-1-ylacetamide: $^1$H NMR (400 MHz, d$_6$-DMSO): δ 8.77-8.78 (m, 2H), 7.98-8.03 (m, 2H), 7.91-7.96 (m, 2H), 7.81-7.84 (m, 3H), 7.49-7.52 (m, 1H), 7.40-7.44 (m, 1H), 7.28-7.31 (m, 3H), 4.41-4.45 (m, 2H), 4.14 (s, 2H), 3.93 (s, 3H), 3.65-3.77 (m, 1H), 3.56-3.62 (m, 2H), 0.94-1.57 (m, 10H). MS (EI) for C$_{34}$H$_{34}$ClN$_5$O$_2$: 581 (MH$^+$).

N-(2-{3-[3-Chloro-4-(methyloxy)phenyl]-5-pyridin-4-yl-1H-1,2,4-triazol-1-yl}ethyl)-N-cyclopropyl-2-naphthalen-1-ylacetamide: $^1$H NMR (400 MHz, d$_6$-DMSO): δ 8.76-8.78 (m, 2H), 7.87-8.05 (m, 5H), 7.81-7.83 (m, 2H), 7.49-7.51 (m, 2H), 7.39-7.44 (m, 1H), 7.24-7.31 (m, 2H), 4.45-4.54 (m, 2H), 4.17-4.24 (m, 1H), 4.10 (s, 2H), 3.92-3.95 (s, 3H), 3.60-3.64 (m, 2H), 0.97-1.10 (m, 4H). MS (EI) for C$_{31}$H$_{28}$ClN$_5$O$_2$: 539 (MH$^+$).

N-Cyclopentyl-N-(2-{5-[4-(methyloxy)phenyl]-3-pyridin-4-yl-1H-1,2,4-triazol-1-yl}ethyl)-2-naphthalen-1-ylacetamide: $^1$H NMR (400 MHz, d$_6$-DMSO): δ 8.8 (d, 2H), 8.18 (d, 2H), 7.8-7.6 (m, 5H), 7.5-7.35 (m, 3H), 7.25 (d, 2H), 7.1 (d, 2H), 4.5 (t, 2H), 4.3 (m, 1H), 4.15 (s, 2H), 3.85 (s, 2H), 3.58 (t, 2H), 1.7-1.2 (m, 8H). MS (EI) for C$_{33}$H$_{33}$N$_5$O$_2$: 532 (MH$^+$).

N-Cyclopentyl-N-(2-{3-[4-(methyloxy)phenyl]-5-pyridin-4-yl-1H-1,2,4-triazol-1-yl}ethyl)-2-naphthalen-1-ylacetamide: $^1$H NMR (400 MHz, d$_6$-DMSO): δ 8.8 (d, 2H), 8.0-7.78 (m, 7H), 7.5-7.35 (m, 3H), 7.2 (d, 2H), 7.05 (d, 2H), 4.5 (t, 2H), 4.3 (m, 1H), 4.1 (s, 2H), 3.8 (s, 2H), 3.55 (t, 2H), 1.65-1.2 (m, 8H). MS (1) for C$_{33}$H$_{33}$N$_5$O$_2$: 532 (MH$^+$).

N-(2-{5-[3,4-Bis(methyloxy)phenyl]-3-pyridin-4-yl-1H-1,2,4-triazol-1-yl}ethyl)-N-cyclopentyl-2-naphthalen-1-ylacetamide: $^1$H NMR (400 MHz, d$_6$-DMSO): δ 8.7 (d, 2H), 7.95-7.8 (m, 5H), 7.5-7.2 (m, 6H), 7.1 (d, 1H), 4.55-4.5 (t, 2H), 4.3 (m, 1H), 4.15 (s, 2H), 3.85 (s, 3H), 3.75 (s, 3H), 3.55 (t, 2H) and 1.65-1.2 (m 8H). MS (EI) for C$_{34}$H$_{35}$N$_5$O$_3$: 562 (MH$^+$).

N-(2-{3-[3,4-Bis(methyloxy)phenyl]-5-pyridin-4-yl-1H-1,2,4-triazol-1-yl}ethyl)-N-cyclopentyl-2-naphthalen-1-ylacetamide: $^1$H NMR (400 MHz, d$_6$-DMSO): δ 8.8 (d, 2H), 7.9-7.8 (m, 5H), 7.6-7.35 (m, 5H), 7.25 (d, 1H), 7.05 (m, 1H), 4.6-4.5 (t, 2H), 4.3 (m, 1H), 4.1 (s, 2H), 3.8 (s, s, 6H), 3.6 (m, 2H) and 1.65-1.2 (m, 8H). MS (EI) for C$_{34}$H$_{35}$N$_5$O$_3$: 562 (MH$^+$).

N-Cyclopentyl-N-[2-(5-methyl-3-pyridin-4-yl-1H-1,2,4-triazol-1-yl)ethyl]-2-naphthalen-1-ylacetamide: $^1$H NMR (400 MHz, d$_6$-DMSO): δ 8.8 (d, 2H), 8.15-8.05 (d, 2H), 7.95-7.8 (m, 3H), 7.5-7.3 (m, 4H), 4.5-5.35 (m, 3H), 4.25 (s, 2H), 3.55 (t, 2H), 2.45 (s, 3H), and 1.8-1.3 (m, 8H). MS (EI) for C$_{27}$H$_{29}$N$_5$O: 440 (MH$^+$).

N-Cyclopentyl-2-naphthalen-1-yl-N-[2-(3-pyridin-4-yl-1H-1,2,4-triazol-1-yl)ethyl]acetamide: $^1$H NMR (400 MHz, d$_6$-DMSO): δ 8.9-8.8 (m, 2H), 8.65 (s, 1H), 8.2-8.1 (d, 2H), 7.95-7.75 (m, 3H), 7.6-7.3 (m, 4H), 4.6-4.45 (t, 2H), 4.3 (m, 1H), 4.25 (s, 2H), 3.6 (t, 2H) and 1.8-1.3 (m, 8H). MS (EI) for C$_{26}$H$_{27}$N$_5$O: 426 (MH$^+$).

N-Cyclopentyl-2-naphthalen-1-yl-N-(2-{3-pyridin-4-yl-5-[3-(trifluoromethyl)phenyl]-1H-1,2,4-triazol-1-yl}ethyl) acetamide: $^1$H NMR (400 MHz, (d$_6$-DMSO): δ 8.8 (d, 2H), 8-2-8.05 (m, 4H), 8.0 (d, 1H), 7.9-7.75 (m, 4H), 7.5-7.3 (m, 3H), 7.2 (d, 1H), 4.6-4.5 (t, 2H), 4.25 (m, 1H), 4.1 (s, 2H), 3.6 (t, 2H), 1.6-1.2 (m, 8H). MS (EI) for C$_{33}$H$_{30}$N$_5$OF$_3$: 570 (MH$^+$).

N-Cyclopentyl-2-naphthalen-1-yl-N-(2-{5-pyridin-4-yl-3-[3-(trifluoromethyl)phenyl]-1H-1,2,4-triazol-1-yl}ethyl) acetamide: $^1$H NMR (400 MHz, d$_6$-DMSO): δ 8.8 (d, 2H), 8.35-8.3 (d, 2H), 7.9-7.7 (m, 7H), 7.5-7.1 (m, 4H), 4.65-4.5 (t, 2H), 4.3 (m, 1H), 4.1 (s, 2H), 3.6 (t, 2H), 1.65-1.35 (m, 8H). MS (EI) for C$_{33}$H$_{30}$N$_5$OF$_3$: 570 (MH$^+$).

N-Cyclopentyl-N-{2-[5-(3,5-dichlorophenyl)-3-pyridin-4-yl-1H-1,2,4-triazol-1-yl]ethyl}-2-naphthalen-1-ylacetamide: $^1$H NMR (400 MHz, d$_6$-DMSO): δ 8.7 (m, 2H), 7.95-7.75 (m, 8H), 7.5-7.2 (m, 4H), 4.55-4.45 (t, 2H), 4.25 (m, 1H), 3.55 (t, 2H), 1.65-1.2 (m, 8H). MS (EI) for C$_{32}$H$_{29}$N$_5$OCl$_2$: 570 (MH$^+$).

N-(2-{5-[3-Chloro-4-(methyloxy)phenyl]-3-pyridin-4-yl-1H-1,2,4-triazol-1-yl}ethyl)-N-cyclopentyl-2-naphthalen-2-ylacetamide: $^1$H NMR (400 MHz, d$_6$-DMSO) mixture of 2 isomers: δ 8.73 (dd, 2H), 8.63 (dd, 2H), 7.96-7.88 (m, 4H), 7.83-7.73 (m, 8H), 7.45-7.38 (m, 7H), 7.28-7.19 (m, 5H), 4.47-4.04 (m, 4H), 4.22-4.16 (m, 2H), 3.87 (s, 3H), 3.86 (s, 3H), 3.77 (s, 3H), 3.73 (s, 2H), 3.53-3.47 (m, 4H), 1.41-1.31 (m, 12H), 1.11-1.08 (m, 4H). MS (EI) for C$_{33}$H$_{32}$ClN$_5$O$_2$: 566 (MH$^+$).

N-Cyclopentyl-2-naphthalen-1-yl-N-[2-(5-phenyl-3-pyridin-4-yl-1H-1,2,4-triazol-1-yl)ethyl]acetamide: $^1$H NMR (400 MHz, d$_6$-DMSO): δ 8.65 (m, 2H), 8.15-7.7 (m, 7H), 7.6-7.05 (m, 4H), 4.6-4.4 (m, 3H), 4.4-4.0 (m, 3H), 3.8 (m, 1H), 3.6 (m, 2H), 1.65-1.20 (m, 8H). MS (EI) for C$_{32}$H$_{31}$N$_5$O: 502 (MH$^+$).

N-Cyclopentyl-2-naphthalen-1-yl-N-[2-(3-phenyl-5-pyridin-4-yl-1H-1,2,4-triazol-1-yl)ethyl]acetamide: $^1$H NMR (400 MHz, d$_6$-DMSO): δ 8.8 (m, 2H), 8.05 (m, 2H), 7.7-7.95 (m, 5H), 7.6-7.1 (m, 7H), 4.6-4.4 (m, 2H), 4.4-4.0 (m, 3H), 3.6 (m, 2H), 1.65-1.20 (m, 8H) MS (EI) for C$_{32}$H$_{31}$N$_5$O: 502 (MH$^+$).

Example 2

N-Cyclopentyl-2-naphthalen-1-yl-N-[2-(3-pyridin-4-yl-1H-1,2,4-triazol-5-yl)ethyl]acetamide: A DMF (5 mL) solution of N-(2-cyanoethyl)cyclopentylamine (4.7 mL, 32. mmol) was added to a stirred solution of HATU (15.3 g, 40.3 mmol), 1-naphthylacetic acid (5.0 g, 27 mmol), and diisopropylethylamine (7.0 mL, 40 mmol) in DMF (40 mL). The mixture stirred at room temperature overnight. Aqueous LiCl (5%) was added and the mixture was extracted three times with ethyl acetate (100 mL). The combined organic layers were washed with brine, dried over sodium sulfate, filtered, and concentrated in vacuo. The crude product was carried to next step without further purification. A sample of this product (3.35 g, 11.0 mmol), isonicotinic hydrazide (1.0 g, 7.3 mmol) and sodium methoxide (600 mg, 11 mmol) was transferred to a pressure tube. Ethanol (4 mL) was added and the reaction was stirred at 120° C. overnight. The reaction was monitored by LCMS. Upon completion, the ethanol was removed in vacuo to afford the product as a solid. The crude mixture was separated by preparative HPLC and lyophilized to afford a solid. $^1$H NMR (400 MHz, d$_6$-DMSO): δ 8.8 (m, 2H), 8.2 (m, 2H), 8.0-7.85 (m, 2H), 7.8-7.7 (m, 1H), 7.6-7.3

(m, 4H), 4.5-4.3 (m, 2H), 3.5 (t, 2H), 3.3-3.0 (m, 2H), 1.8-1.3 (m, 9H). MS (EI) for $C_{26}H_{27}N_5O$: 426 ($MH^+$).

Example 3

N-Cyclopentyl-2-naphthalen-1-yl-N-[2-(3-pyridin-4-yl-1,2,4-oxadiazol-5-yl)ethyl]acetamide: A mixture of 4-cyanopyridine (10.0 g, 96.0 mmol) and hydroxylamine (17.6 mL, 50 wt. % solution in water, 288 mmol) in ethanol (100 mL) was heated to reflux overnight. Upon cooling, a white solid precipitated. This material was collected by filtration and recrystallized from ethanol to give the aldoxime as white needles (10.1 g, 77%). To a solution of Boc-β-alanine (2.95 g, 15.6 mmol) and diisopropylethylamine (6.8 mL, 39 mmol) in DMF (100 mL) was added HOBt (2.3 g, 17 mmol) and EDCI (3.3 g, 17 mmol). The mixture was stirred at room temperature for 1 h, then a portion of the aldoxime obtained above (1.8 g, 13 mmol) was added. The reaction was allowed to stir at room temperature overnight, was then diluted with 5% lithium chloride (100 mL). The mixture was extracted with ethyl acetate (3×) and the combined organic layers were washed with saturated sodium bicarbonate and brine, dried over sodium sulfate and concentrated on a rotary evaporator. The residue was dissolved in THF (200 mL) and tetrabutylammonium fluoride (13 mL, 1 M solution in THF, 13 mmol) was added. The solution was stirred at room temperature for 4 h and the solvent was removed on a rotary evaporator. The residue was taken up in ethyl acetate and the organic layer was washed with water and brine, dried over sodium sulfate and concentrated on a rotary evaporator. The residue was purified by silica gel chromatography to give the oxadiazole as a white solid (2.4 g, 64%). A portion of this oxadiazole (1.0 g, 3.4 mmol) was dissolved in dioxane (20 mL) and methanol (10 mL) and then treated with a solution of HCl in dioxane (10 mL, 4 M solution, 40 mmol). The mixture was stirred at room temperature overnight and the solvent was removed on a rotary evaporator to give a white solid. This residue was taken up in methanol (25 mL) and cyclopentanone (330 μL, 3.7 mmol) was added. The mixture was stirred at room temperature for 1 h, sodium cyanoborohydride (3.7 mL, 1 M solution in THF, 3.7 mmol) was then added. Acetic acid was added dropwise to bring the pH of the reaction to 5, the reaction was then stirred at room temperature overnight. The reaction was concentrated on a rotary evaporator and the residue was purified by silica gel chromatography to give a white solid (515 mg, 59%). A portion of this solid (300 mg, 1.16 mmol), 1-naphthylacetic acid (180 mg, 1.0 mmol), HATU (4351.1 mmol) and diisopropylethylamine (400 μL, 2.3 mmol) were stirred in DMF (10 mL) at room temperature overnight. The residue was then diluted with 5% lithium chloride (10 mL) and the mixture was extracted with ethyl acetate (3×). The combined organic extracts were washed with brine, dried over sodium sulfate and concentrated on a rotary evaporator. The residue was purified by preparative HPLC to give the title compound as a white solid (155 mg, 31%). $^1$H NMR (400 MHz, $d_6$-DMSO): δ 8.82 (m, 2H), 7.90 (m, 5H), 7.41 (m, 4H), 4.37 (m, 1H), 4.24 (s, 2H), 3.66 (t, 2H), 3.27 (t, 2H), 1.60 (m, 8H). MS (EI) for $C_{26}H_{26}N_4O_2$: 427 ($MH^+$).

Assays

For assay of activity, generally Tie-2, or a compound according to the invention is non-diffusably bound to an insoluble support having isolated sample-receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is $K_i$. For compounds with $IC_{50}$'s less than 1 μM, the $K_i$ or $K_d$ is defined as the dissociation rate constant for the interaction of the agent with a Tie-2. Exemplary compositions have $K_i$'s of, for example, less than about 100 μM, less than about 10 μM, less than about 1 μM, and further for example having $K_i$'s of less than about 100 nM, and still further, for example, less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 mM, less than about 10 μM, less than about 1 μM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption by in the presence of a generic substrate such as polyglutamine, tyrosine (pEY), by luciferase/luciferin-mediated chemiluminescence or; 2) incorporation of radioactive phosphate derived from $^{33}$P-ATP into a generic substrate which has been absorbed onto the well surface of polystyrene microtiter plates. Phosphorylated substrate products are quantified by scintillation spectrometry.

Structure Activity Relationships

Table 2 shows structure activity relationship data for selected compounds of the invention. Inhibition is indicated as $IC_{50}$ with following key: A=$IC_{50}$ less than 50 nM, B=$IC_{50}$ greater than 50 nM, but less than or equal to 1000 nM, C=$IC_{50}$ greater than 1000 nM, but less than 10,000 nM, and D=$IC_{50}$ 10,000 nM or greater. The abbreviation for human enzyme, Tie-2, is defined as tyrosine kinase with immunoglobulin and EGF repeats.

TABLE 2

| Entry | Name | IC$_{50}$ |
|---|---|---|
| 1 | N-{2-[5-(3-chloro-4-hydroxyphenyl)-3-pyridin-4-yl-1H-1,2,4-triazol-1-yl]ethyl}-N-cyclopentyl-2-naphthalen-1-ylacetamide | A |
| 2 | ethyl {5-[3-chloro-4-(methyloxy)phenyl]-3-pyridin-4-yl-1H-1,2,4-triazol-1-yl}acetate | D |
| 3 | 2-{5-[3-chloro-4-(methyloxy)phenyl]-3-pyridin-4-yl-1H-1,2,4-triazol-1-yl}-N-cyclopentylacetamide | D |
| 4 | ethyl {3-[3-chloro-4-(methyloxy)phenyl]-5-pyridin-4-yl-1H-1,2,4-triazol-1-yl}acetate | D |
| 5 | 2-{3-[3-chloro-4-(methyloxy)phenyl]-5-pyridin-4-yl-1H-1,2,4-triazol-1-yl}-N-cyclopentylacetamide | D |
| 6 | methyl 3-{5-[3-chloro-4-(methyloxy)phenyl]-3-pyridin-4-yl-1H-1,2,4-triazol-1-yl}propanoate | D |
| 7 | methyl 3-{3-[3-chloro-4-(methyloxy)phenyl]-5-pyridin-4-yl-1H-1,2,4-triazol-1-yl}propanoate | D |
| 8 | N-(3-{5-[3-chloro-4-(methyloxy)phenyl]-3-pyridin-4-yl-1H-1,2,4-triazol-1-yl}propyl)-N-cyclopentyl-2-naphthalen-1-ylacetamide | D |
| 9 | N-(3-{3-[3-chloro-4-(methyloxy)phenyl]-5-pyridin-4-yl-1H-1,2,4-triazol-1-yl}propyl)-N-cyclopentyl-2-naphthalen-1-ylacetamide | D |
| 10 | N-(2-{5-[3-chloro-4-(methyloxy)phenyl]-3-pyridin-4-yl-1H-1,2,4-triazol-1-yl}ethyl)-N-cyclopentyl-2-naphthalen-1-ylacetamide | A |
| 11 | N-{2-[3-(3-chloro-4-hydroxyphenyl)-5-pyridin-4-yl-1H-1,2,4-triazol-1-yl]ethyl}-N-cyclopentyl-2-naphthalen-1-ylacetamide | B |
| 12 | 2-{3-[3-chloro-4-(methyloxy)phenyl]-5-pyridin-3-yl-1H-1,2,4-triazol-1-yl}-N-cyclopentylacetamide | D |
| 13 | N-(2-{5-[3-chloro-4-(methyloxy)phenyl]-3-pyridin-3-yl-1H-1,2,4-triazol-1-yl}ethyl)-N-cyclopentyl-2-naphthalen-1-ylacetamide | D |
| 14 | ethyl [5-(4-nitrophenyl)-3-pyridin-4-yl-1H-1,2,4-triazol-1-yl]acetate | D |
| 15 | ethyl [5-(3,5-dichlorophenyl)-3-pyridin-4-yl-1H-1,2,4-triazol-1-yl]acetate | D |
| 16 | ethyl [3-(3,5-dichlorophenyl)-5-pyridin-4-yl-1H-1,2,4-triazol-1-yl]acetate | D |
| 17 | N-cyclopentyl-N-[2-(5-furan-2-yl-3-pyridin-4-yl-1H-1,2,4-triazol-1-yl)ethyl]-2-naphthalen-1-ylacetamide | A |
| 18 | N-cyclopentyl-N-[2-(3-furan-2-yl-5-pyridin-4-yl-1H-1,2,4-triazol-1-yl)ethyl]-2-naphthalen-1-ylacetamide | B |
| 19 | N-cyclopentyl-2-naphthalen-1-yl-N-{2-[5-pyridin-4-yl-3-(2-thienyl)-1H-1,2,4-triazol-1-yl]ethyl}acetamide | B |
| 20 | N-(2-{5-[3-chloro-4-(methyloxy)phenyl]-3-pyridin-4-yl-1H-1,2,4-triazol-1-yl}ethyl)-N-cyclopentylnaphthalene-1-carboxamide | C |
| 21 | N-(2-{5-[3-chloro-4-(methyloxy)phenyl]-3-pyridin-4-yl-1H-1,2,4-triazol-1-yl}ethyl)-N-cyclopentylnaphthalene-2-carboxamide | D |
| 22 | N-cyclopentyl-N-(2-{5-[3-(methyloxy)phenyl]-3-pyridin-4-yl-1H-1,2,4-triazol-1-yl}ethyl)-2-naphthalen-1-ylacetamide | A |
| 23 | N-cyclopentyl-N-(2-{3-[3-(methyloxy)phenyl]-5-pyridin-4-yl-1H-1,2,4-triazol-1-yl}ethyl)-2-naphthalen-1-ylacetamide | B |
| 24 | N-(4-{5-[3-chloro-4-(methyloxy)phenyl]-3-pyridin-4-yl-1H-1,2,4-triazol-1-yl}butyl)-N-cyclopentyl-2-naphthalen-1-ylacetamide | C |
| 25 | N-(4-{3-[3-chloro-4-(methyloxy)phenyl]-5-pyridin-4-yl-1H-1,2,4-triazol-1-yl}butyl)-N-cyclopentyl-2-naphthalen-1-ylacetamide | D |
| 26 | N-(2-{5-[3-chloro-4-(methyloxy)phenyl]-3-pyridin-4-yl-1H-1,2,4-triazol-1-yl}ethyl)-N-cyclopentylbenzamide | D |
| 27 | N-(2-{3-[3-chloro-4-(methyloxy)phenyl]-5-pyridin-4-yl-1H-1,2,4-triazol-1-yl}ethyl)-N-cyclopentylbenzamide | D |
| 28 | N-(2-{5-[3-chloro-4-(methyloxy)phenyl]-3-pyridin-4-yl-1H-1,2,4-triazol-1-yl}ethyl)-N-cyclopentylquinoline-4-carboxamide | D |
| 29 | N-(2-{5-[3-chloro-4-(methyloxy)phenyl]-3-pyridin-4-yl-1H-1,2,4-triazol-1-yl}ethyl)-N-cyclopentyl-N'-naphthalen-1-ylurea | A |
| 30 | N-(2-{5-[3-chloro-4-(methyloxy)phenyl]-3-pyridin-4-yl-1H-1,2,4-triazol-1-yl}ethyl)-N-cyclopentyl-N'-phenylurea | D |
| 31 | N-(2-{5-[3-chloro-4-(methyloxy)phenyl]-3-pyridin-4-yl-1H-1,2,4-triazol-1-yl}ethyl)-N-cyclopentyl-2-phenylacetamide | C |
| 32 | N-(2-{5-[3-chloro-4-(methyloxy)phenyl]-3-phenyl-1H-1,2,4-triazol-1-yl}ethyl)-N-cyclopentyl-2-naphthalen-1-ylacetamide | D |
| 33 | 2-{5-[3-chloro-4-(methyloxy)phenyl]-3-phenyl-1H-1,2,4-triazol-1-yl}-N-cyclopentylacetamide | D |
| 34 | N-(2-{5-[3-chloro-4-(methyloxy)phenyl]-3-pyridin-4-yl-1H-1,2,4-triazol-1-yl}ethyl)-2-naphthalen-1-ylacetamide | C |
| 35 | N-(2-{3-[3-chloro-4-(methyloxy)phenyl]-5-pyridin-4-yl-1H-1,2,4-triazol-1-yl}ethyl)-N-(1-methylethyl)-2-naphthalen-1-ylacetamide | D |
| 36 | N-(2-{5-[3-chloro-4-(methyloxy)phenyl]-3-pyridin-4-yl-1H-1,2,4-triazol-1-yl}ethyl)-N-cyclohexyl-2-naphthalen-1-ylacetamide | A |
| 37 | N-(2-{3-[3-chloro-4-(methyloxy)phenyl]-5-pyridin-4-yl-1H-1,2,4-triazol-1-yl}ethyl)-N-cyclohexyl-2-naphthalen-1-ylacetamide | B |
| 38 | N-(2-{3-[3-chloro-4-(methyloxy)phenyl]-5-pyridin-4-yl-1H-1,2,4-triazol-1-yl}ethyl)-N-cyclopropyl-2-naphthalen-1-ylacetamide | B |
| 39 | N-cyclopentyl-N-(2-{5-[4-(methyloxy)phenyl]-3-pyridin-4-yl-1H-1,2,4-triazol-1-yl}ethyl)-2-naphthalen-1-ylacetamide | A |
| 40 | N-cyclopentyl-N-(2-{3-[4-(methyloxy)phenyl]-5-pyridin-4-yl-1H-1,2,4-triazol-1-yl}ethyl)-2-naphthalen-1-ylacetamide | C |

TABLE 2-continued

| Entry | Name | IC$_{50}$ |
|---|---|---|
| 41 | N-(2-{5-[3,4-bis(methyloxy)phenyl]-3-pyridin-4-yl-1H-1,2,4-triazol-1-yl}ethyl)-N-cyclopentyl-2-naphthalen-1-ylacetamide | A |
| 42 | N-(2-{3-[3,4-bis(methyloxy)phenyl]-5-pyridin-4-yl-1H-1,2,4-triazol-1-yl}ethyl)-N-cyclopentyl-2-naphthalen-1-ylacetamide | B |
| 43 | N-cyclopentyl-N-[2-(5-methyl-3-pyridin-4-yl-1H-1,2,4-triazol-1-yl)ethyl]-2-naphthalen-1-ylacetamide | A |
| 44 | N-cyclopentyl-2-naphthalen-1-yl-N-[2-(3-pyridin-4-yl-1H-1,2,4-triazol-1-yl)ethyl]acetamide | A |
| 45 | N-cyclopentyl-2-naphthalen-1-yl-N-(2-{3-pyridin-4-yl-5-[3-(trifluoromethyl)phenyl]-1H-1,2,4-triazol-1-yl}ethyl)acetamide | A |
| 46 | N-cyclopentyl-2-naphthalen-1-yl-N-(2-{5-pyridin-4-yl-3-[3-(trifluoromethyl)phenyl]-1H-1,2,4-triazol-1-yl}ethyl)acetamide | D |
| 47 | N-cyclopentyl-N-{2-[5-(3,5-dichlorophenyl)-3-pyridin-4-yl-1H-1,2,4-triazol-1-yl]ethyl}-2-naphthalen-1-ylacetamide | A |
| 48 | N-(2-{5-[3-chloro-4-(methyloxy)phenyl]-3-pyridin-4-yl-1H-1,2,4-triazol-1-yl}ethyl)-N-cyclopentyl-2-naphthalen-2-ylacetamide | D |
| 49 | N-cyclopentyl-2-naphthalen-1-yl-N-[2-(5-pyridin-4-yl-1H-1,2,4-triazol-3-yl)ethyl]acetamide | A |
| 50 | N-cyclopentyl-2-naphthalen-1-yl-N-[2-(5-phenyl-3-pyridin-4-yl-1H-1,2,4-triazol-1-yl)ethyl]acetamide | A |
| 51 | N-cyclopentyl-2-naphthalen-1-yl-N-[2-(3-phenyl-5-pyridin-4-yl-1H-1,2,4-triazol-1-yl)ethyl]acetamide | C |
| 52 | N-cyclopentyl-2-naphthalen-1-yl-N-[2-(3-pyridin-4-yl-1,2,4-oxadiazol-5-yl)ethyl]acetamide | B |
| 53 | N-{2-[5-[3-chloro-4-(methyloxy)phenyl]-3-(2-chloropyridin-4-yl)-1H-1,2,4-triazol-1-yl]ethyl}-N-cyclopentyl-2-naphthalen-1-ylacetamide | D |
| 54 | N-cyclopentyl-N-(2-{4-[4-(methyloxy)phenyl]-2-pyridin-4-yl-1H-imidazol-5-yl}ethyl)-2-naphthalen-1-ylacetamide | B |
| 55 | N-(2-{3-[3-chloro-4-(methyloxy)phenyl]-5-pyridin-4-yl-1H-1,2,4-triazol-1-yl}ethyl)-N-cyclopentyl-N'-naphthalen-1-ylurea | D |
| 56 | N-cyclopentyl-N-{2-[5-(3-fluorophenyl)-3-pyridin-4-yl-1H-1,2,4-triazol-1-yl]ethyl}-2-naphthalen-1-ylacetamide | A |
| 57 | N-cyclopentyl-N-{2-[3-(3-fluorophenyl)-5-pyridin-4-yl-1H-1,2,4-triazol-1-yl]ethyl}-2-naphthalen-1-ylacetamide | C |
| 58 | N-{2-[5-(3-chlorophenyl)-3-pyridin-4-yl-1H-1,2,4-triazol-1-yl]ethyl}-N-cyclopentyl-2-naphthalen-1-ylacetamide | A |
| 59 | N-{2-[3-(3-chlorophenyl)-5-pyridin-4-yl-1H-1,2,4-triazol-1-yl]ethyl}-N-cyclopentyl-2-naphthalen-1-ylacetamide | C |
| 60 | N-cyclopentyl-2-naphthalen-1-yl-N-[2-(5-piperidin-4-yl-3-pyridin-4-yl-1H-1,2,4-triazol-1-yl)ethyl]acetamide | A |
| 61 | N-{2-[5-(2-chlorophenyl)-3-pyridin-4-yl-1H-1,2,4-triazol-1-yl]ethyl}-N-cyclopentyl-2-naphthalen-1-ylacetamide | A |
| 62 | N-{2-[3-(2-chlorophenyl)-5-pyridin-4-yl-1H-1,2,4-triazol-1-yl]ethyl}-N-cyclopentyl-2-naphthalen-1-ylacetamide | C |
| 63 | N-{2-[5-(1,3-benzodioxol-5-yl)-3-pyridin-4-yl-1H-1,2,4-triazol-1-yl]ethyl}-N-cyclopentyl-2-naphthalen-1-ylacetamide | A |
| 64 | N-{2-[3-(1,3-benzodioxol-5-yl)-5-pyridin-4-yl-1H-1,2,4-triazol-1-yl]ethyl}-N-cyclopentyl-2-naphthalen-1-ylacetamide | C |
| 65 | N-{2-[5-(3-bromophenyl)-3-pyridin-4-yl-1H-1,2,4-triazol-1-yl]ethyl}-N-cyclopentyl-2-naphthalen-1-ylacetamide | A |
| 66 | N-{2-[3-(3-bromophenyl)-5-pyridin-4-yl-1H-1,2,4-triazol-1-yl]ethyl}-N-cyclopentyl-2-naphthalen-1-ylacetamide | D |
| 67 | N-{2-[5-(4-bromophenyl)-3-pyridin-4-yl-1H-1,2,4-triazol-1-yl]ethyl}-N-cyclopentyl-2-naphthalen-1-ylacetamide | A |
| 68 | N-{2-[3-(4-bromophenyl)-5-pyridin-4-yl-1H-1,2,4-triazol-1-yl]ethyl}-N-cyclopentyl-2-naphthalen-1-ylacetamide | A |
| 69 | N-cyclopentyl-N-[2-(5-methyl-3-pyridazin-4-yl-1H-1,2,4-triazol-1-yl)ethyl]-2-naphthalen-1-ylacetamide | B |
| 70 | N-cyclopentyl-N-{2-[5-(4-methylphenyl)-3-pyridin-4-yl-1H-1,2,4-triazol-1-yl]ethyl}-2-naphthalen-1-ylacetamide | A |
| 71 | N-cyclopentyl-N-{2-[3-(4-methylphenyl)-5-pyridin-4-yl-1H-1,2,4-triazol-1-yl]ethyl}-2-naphthalen-1-ylacetamide | C |
| 72 | N-cyclopentyl-N-{2-[5-(3-methylphenyl)-3-pyridin-4-yl-1H-1,2,4-triazol-1-yl]ethyl}-2-naphthalen-1-ylacetamide | A |
| 73 | N-cyclopentyl-N-{2-[3-(3-methylphenyl)-5-pyridin-4-yl-1H-1,2,4-triazol-1-yl]ethyl}-2-naphthalen-1-ylacetamide | C |
| 74 | N-cyclopentyl-N-{2-[5-(2,4-dichlorophenyl)-3-pyridin-4-yl-1H-1,2,4-triazol-1-yl]ethyl}-2-naphthalen-1-ylacetamide | A |
| 75 | N-cyclopentyl-N-{2-[3-(2,4-dichlorophenyl)-5-pyridin-4-yl-1H-1,2,4-triazol-1-yl]ethyl}-2-naphthalen-1-ylacetamide | C |
| 76 | N-cyclopentyl-2-naphthalen-1-yl-N-(2-{3-pyridin-4-yl-5-[4-(trifluoromethyl)phenyl]-1H-1,2,4-triazol-1-yl}ethyl)acetamide | A |
| 77 | N-cyclopentyl-2-naphthalen-1-yl-N-(2-{5-pyridin-4-yl-3-[4-(trifluoromethyl)phenyl]-1H-1,2,4-triazol-1-yl}ethyl)acetamide | D |
| 78 | N-(2-{5-[3-chloro-4-(methyloxy)phenyl]-3-pyridin-4-yl-1H-1,2,4-triazol-1-yl}ethyl)-N-cyclopropyl-2-naphthalen-1-ylacetamide | A |
| 79 | N-(2-{5-[3-chloro-4-(methyloxy)phenyl]-3-pyridin-4-yl-1H-1,2,4-triazol-1-yl}ethyl)-N-(1-methylethyl)-2-naphthalen-1-ylacetamide | D |

TABLE 2-continued

| Entry | Name | IC$_{50}$ |
|---|---|---|
| 80 | N-cyclopentyl-N-[2-(5-ethyl-3-pyridin-4-yl-1H-1,2,4-triazol-1-yl)ethyl]-2-naphthalen-1-ylacetamide | A |
| 81 | N-(2-{5-[3-chloro-4-(methyloxy)phenyl]-3-pyridin-4-yl-1H-1,2,4-triazol-1-yl}ethyl)-N-(1-methylpiperidin-4-yl)-2-naphthalen-1-ylacetamide | D |
| 82 | N-(2-{5-[3-chloro-4-(methyloxy)phenyl]-3-pyridin-4-yl-1H-1,2,4-triazol-1-yl}ethyl)-N-cyclopentyl-N'-[(1R,2S)-2-phenylcyclopropyl]urea | C |
| 83 | N-(2-{5-[3-chloro-4-(methyloxy)phenyl]-3-pyridin-4-yl-1H-1,2,4-triazol-1-yl}ethyl)-N-cyclopentyl-N'-(2,4-dichlorophenyl)urea | D |
| 84 | N-(2-{5-[3-chloro-4-(methyloxy)phenyl]-3-pyridin-4-yl-1H-1,2,4-triazol-1-yl}ethyl)-N-cyclopentyl-N'-[2-(methyloxy)phenyl]urea | D |
| 85 | N'-[2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea | D |
| 86 | N-(2-{5-[3-chloro-4-(methyloxy)phenyl]-3-pyridin-4-yl-1H-1,2,4-triazol-1-yl}ethyl)-N-cyclopentyl-N'-(2-methylphenyl)urea | C |
| 87 | N-(2-{5-[3-chloro-4-(methyloxy)phenyl]-3-pyridin-4-yl-1H-1,2,4-triazol-1-yl}ethyl)-N-cyclopentyl-N'-(2-ethylphenyl)urea | C |
| 88 | N-(2-{5-[3-chloro-4-(methyloxy)phenyl]-3-pyridin-4-yl-1H-1,2,4-triazol-1-yl}ethyl)-N-cyclopentyl-N'-(3,4-dichlorophenyl)urea | D |
| 89 | N-(2-{5-[3-chloro-4-(methyloxy)phenyl]-3-pyridin-4-yl-1H-1,2,4-triazol-1-yl}ethyl)-N-cyclopentyl-N'-hexylurea | D |
| 90 | N-(2-{5-[3-chloro-4-(methyloxy)phenyl]-3-pyridin-4-yl-1H-1,2,4-triazol-1-yl}ethyl)-N-cyclopentyl-N'-(4-fluorophenyl)urea | D |
| 91 | N-(2-{5-[3-chloro-4-(methyloxy)phenyl]-3-pyridin-4-yl-1H-1,2,4-triazol-1-yl}ethyl)-N-cyclopentyl-N'-[4-(methyloxy)phenyl]urea | D |
| 92 | N-(2-{5-[3-chloro-4-(methyloxy)phenyl]-3-pyridin-4-yl-1H-1,2,4-triazol-1-yl}ethyl)-N-cyclopentyl-N'-(phenylmethyl)urea | C |
| 93 | N'-[3,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylurea | D |
| 94 | N-(2-{5-[3-chloro-4-(methyloxy)phenyl]-3-pyridin-4-yl-1H-1,2,4-triazol-1-yl}ethyl)-N-cyclopentyl-N'-[3,4,5-tris(methyloxy)phenyl]urea | D |
| 95 | N'-(3-acetylphenyl)-N-(2-{5-[3-chloro-4-(methyloxy)phenyl]-3-pyridin-4-yl-1H-1,2,4-triazol-1-yl}ethyl)-N-cyclopentylurea | D |
| 96 | N-(2-{5-[3-chloro-4-(methyloxy)phenyl]-3-pyridin-4-yl-1H-1,2,4-triazol-1-yl}ethyl)-N-cyclopentyl-N'-(3,4-dimethylphenyl)urea | D |
| 97 | N-(2-{5-[3-chloro-4-(methyloxy)phenyl]-3-pyridin-4-yl-1H-1,2,4-triazol-1-yl}ethyl)-N'-[4-chloro-2-(trifluoromethyl)phenyl]-N-cyclopentylurea | C |
| 98 | N-(2-{5-[3-chloro-4-(methyloxy)phenyl]-3-pyridin-4-yl-1H-1,2,4-triazol-1-yl}ethyl)-N-cyclopentyl-N'-[4-(methylthio)phenyl]urea | D |
| 99 | N'-(4-acetylphenyl)-N-(2-{5-[3-chloro-4-(methyloxy)phenyl]-3-pyridin-4-yl-1H-1,2,4-triazol-1-yl}ethyl)-N-cyclopentylurea | D |
| 100 | N-(2-{5-[3-chloro-4-(methyloxy)phenyl]-3-pyridin-4-yl-1H-1,2,4-triazol-1-yl}ethyl)-N-cyclopentyl-N'-[4-(1-methylethyl)phenyl]urea | D |
| 101 | N-(2-{5-[3-chloro-4-(methyloxy)phenyl]-3-pyridin-4-yl-1H-1,2,4-triazol-1-yl}ethyl)-N'-(4-cyanophenyl)-N-cyclopentylurea | D |
| 102 | N'-biphenyl-2-yl-N-(2-{5-[3-chloro-4-(methyloxy)phenyl]-3-pyridin-4-yl-1H-1,2,4-triazol-1-yl}ethyl)-N-cyclopentylurea | D |
| 103 | N-(2-{5-[3-chloro-4-(methyloxy)phenyl]-3-pyridin-4-yl-1H-1,2,4-triazol-1-yl}ethyl)-N-cyclopentyl-N'-pentylurea | D |
| 104 | N-(2-{5-[3-chloro-4-(methyloxy)phenyl]-3-pyridin-4-yl-1H-1,2,4-triazol-1-yl}ethyl)-N-cyclopentyl-N'-heptylurea | D |
| 105 | N-(2-{5-[3-chloro-4-(methyloxy)phenyl]-3-pyridin-4-yl-1H-1,2,4-triazol-1-yl}ethyl)-N'-(3-chlorophenyl)-N-cyclopentylurea | D |
| 106 | N-(2-{5-[3-chloro-4-(methyloxy)phenyl]-3-pyridin-4-yl-1H-1,2,4-triazol-1-yl}ethyl)-N-cyclopentyl-N'-(3-methylphenyl)urea | D |
| 107 | N-(2-{5-[3-chloro-4-(methyloxy)phenyl]-3-pyridin-4-yl-1H-1,2,4-triazol-1-yl}ethyl)-N-cyclopentyl-N'-(1,1-dimethylethyl)urea | D |
| 108 | N-(2-{5-[3-chloro-4-(methyloxy)phenyl]-3-pyridin-4-yl-1H-1,2,4-triazol-1-yl}ethyl)-N-cyclopentyl-N'-(1-methylethyl)urea | D |
| 109 | N-(2-{5-[3-chloro-4-(methyloxy)phenyl]-3-pyridin-4-yl-1H-1,2,4-triazol-1-yl}ethyl)-N-cyclopentyl-N'-ethylurea | D |
| 110 | N-(2-{5-[3-chloro-4-(methyloxy)phenyl]-3-pyridin-4-yl-1H-1,2,4-triazol-1-yl}ethyl)-N-cyclopentyl-N'-propylurea | D |
| 111 | N-(2-{5-[3-chloro-4-(methyloxy)phenyl]-3-pyridin-4-yl-1H-1,2,4-triazol-1-yl}ethyl)-N-cyclopentyl-N'-[4-(ethyloxy)phenyl]urea | C |
| 112 | N-(2-{5-[3-chloro-4-(methyloxy)phenyl]-3-pyridin-4-yl-1H-1,2,4-triazol-1-yl}ethyl)-N-cyclopentyl-N'-(4-ethylphenyl)urea | D |
| 113 | N-(2-{5-[3-chloro-4-(methyloxy)phenyl]-3-pyridin-4-yl-1H-1,2,4-triazol-1-yl}ethyl)-N-cyclopentyl-N'-(2-phenylethyl)urea | D |
| 114 | N-(2-{5-[3-chloro-4-(methyloxy)phenyl]-3-pyridin-4-yl-1H-1,2,4-triazol-1-yl}ethyl)-N-cyclopentyl-N'-{1-methyl-1-[3-(1-methylethenyl)phenyl]ethyl}urea | D |
| 115 | N-(2-{5-[3-chloro-4-(methyloxy)phenyl]-3-pyridin-4-yl-1H-1,2,4-triazol-1-yl}ethyl)-N-cyclopentyl-N'-(2-fluorophenyl)urea | D |
| 116 | N-(2-{5-[3-chloro-4-(methyloxy)phenyl]-3-pyridin-4-yl-1H-1,2,4-triazol-1-yl}ethyl)-N-cyclopentyl-N'-(2,4-difluorophenyl)urea | D |
| 117 | N-(2-{5-[3-chloro-4-(methyloxy)phenyl]-3-pyridin-4-yl-1H-1,2,4-triazol-1-yl}ethyl)-N-cyclopentyl-N'-(2,6-difluorophenyl)urea | D |
| 118 | N-(2-{5-[3-chloro-4-(methyloxy)phenyl]-3-pyridin-4-yl-1H-1,2,4-triazol-1-yl}ethyl)-N'-(2-chlorophenyl)-N-cyclopentylurea | C |

TABLE 2-continued

| Entry | Name | IC$_{50}$ |
|---|---|---|
| 119 | N-(2-{5-[3-chloro-4-(methyloxy)phenyl]-3-pyridin-4-yl-1H-1,2,4-triazol-1-yl}ethyl)-N-cyclopentyl-N'-(2,3-dichlorophenyl)urea | D |
| 120 | N'-[2,5-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea | D |
| 121 | N-(2-{5-[3-chloro-4-(methyloxy)phenyl]-3-pyridin-4-yl-1H-1,2,4-triazol-1-yl}ethyl)-N-cyclopentyl-N'-[2-(ethyloxy)phenyl]urea | C |
| 122 | N-(2-{5-[3-chloro-4-(methyloxy)phenyl]-3-pyridin-4-yl-1H-1,2,4-triazol-1-yl}ethyl)-N-cyclopentyl-N'-[2-(trifluoromethyl)phenyl]urea | D |
| 123 | N-(2-{5-[3-chloro-4-(methyloxy)phenyl]-3-pyridin-4-yl-1H-1,2,4-triazol-1-yl}ethyl)-N-cyclopentyl-N'-(2,6-dimethylphenyl)urea | D |
| 124 | N-(2-{5-[3-chloro-4-(methyloxy)phenyl]-3-pyridin-4-yl-1H-1,2,4-triazol-1-yl}ethyl)-N-cyclopentyl-N'-[4-(trifluoromethyl)phenyl]urea | D |
| 125 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]urea | C |
| 126 | N-(2-{5-[3-chloro-4-(methyloxy)phenyl]-3-pyridin-4-yl-1H-1,2,4-triazol-1-yl}ethyl)-N-cyclopentyl-N'-(2,4,5-trichlorophenyl)urea | D |
| 127 | N-(2-{5-[3-chloro-4-(methyloxy)phenyl]-3-pyridin-4-yl-1H-1,2,4-triazol-1-yl}ethyl)-N-cyclopentyl-N'-(2,3-dimethylphenyl)urea | C |
| 128 | N-(2-{5-[3-chloro-4-(methyloxy)phenyl]-3-pyridin-4-yl-1H-1,2,4-triazol-1-yl}ethyl)-N-cyclopentyl-N'-(2,4-dimethylphenyl)urea | D |
| 129 | N-(2-{5-[3-chloro-4-(methyloxy)phenyl]-3-pyridin-4-yl-1H-1,2,4-triazol-1-yl}ethyl)-N'-(3-chloro-4-methylphenyl)-N-cyclopentylurea | D |
| 130 | N-(2-{5-[3-chloro-4-(methyloxy)phenyl]-3-pyridin-4-yl-1H-1,2,4-triazol-1-yl}ethyl)-N-cyclopentyl-N'-[2-(1,1-dimethylethyl)-6-methylphenyl]urea | D |
| 131 | N'-[4-(butyloxy)phenyl]-N-(2-{5-[3-chloro-4-(methyloxy)phenyl]-3-pyridin-4-yl-1H-1,2,4-triazol-1-yl}ethyl)-N-cyclopentylurea | D |
| 132 | N-(2-{5-[3-chloro-4-(methyloxy)phenyl]-3-pyridin-4-yl-1H-1,2,4-triazol-1-yl}ethyl)-N-cyclopentyl-N'-(2-methyl-3-nitrophenyl)urea | D |
| 133 | N-(2-{5-[3-chloro-4-(methyloxy)phenyl]-3-pyridin-4-yl-1H-1,2,4-triazol-1-yl}ethyl)-N-cyclopentyl-N'-(2,5-dichlorophenyl)urea | D |
| 134 | N-(2-{5-[3-chloro-4-(methyloxy)phenyl]-3-pyridin-4-yl-1H-1,2,4-triazol-1-yl}ethyl)-N-cyclopentyl-N'-(3-fluorophenyl)urea | C |
| 135 | N-(2-{5-[3-chloro-4-(methyloxy)phenyl]-3-pyridin-4-yl-1H-1,2,4-triazol-1-yl}ethyl)-N'-(4-chlorophenyl)-N-cyclopentylurea | D |
| 136 | N-(2-{5-[3-chloro-4-(methyloxy)phenyl]-3-pyridin-4-yl-1H-1,2,4-triazol-1-yl}ethyl)-N-cyclopentyl-N'-(4-methylphenyl)urea | D |
| 137 | N-(2-{5-[3-chloro-4-(methyloxy)phenyl]-3-pyridin-4-yl-1H-1,2,4-triazol-1-yl}ethyl)-N-cyclopentyl-N'-(2,4,6-trichlorophenyl)urea | D |
| 138 | N-(2-{5-[3-chloro-4-(methyloxy)phenyl]-3-pyridin-4-yl-1H-1,2,4-triazol-1-yl}ethyl)-N-cyclopentyl-N'-[2-methyl-4-(methyloxy)phenyl]urea | C |
| 139 | N-(2-{5-[3-chloro-4-(methyloxy)phenyl]-3-pyridin-4-yl-1H-1,2,4-triazol-1-yl}ethyl)-N-cyclopentyl-N'-(2,5-dimethylphenyl)urea | C |
| 140 | N'-[5-chloro-2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea | D |
| 141 | N-(2-{5-[3-chloro-4-(methyloxy)phenyl]-3-pyridin-4-yl-1H-1,2,4-triazol-1-yl}ethyl)-N-cyclopentyl-N'-(3,5-dichlorophenyl)urea | D |
| 142 | N'-[5-chloro-2-(methyloxy)phenyl]-N-(2-{5-[3-chloro-4-(methyloxy)phenyl]-3-pyridin-4-yl-1H-1,2,4-triazol-1-yl}ethyl)-N-cyclopentylurea | D |
| 143 | N-(2-{5-[3-chloro-4-(methyloxy)phenyl]-3-pyridin-4-yl-1H-1,2,4-triazol-1-yl}ethyl)-N-cyclopentyl-N'-[3-(methylthio)phenyl]urea | D |
| 144 | N-(2-{5-[3-chloro-4-(methyloxy)phenyl]-3-pyridin-4-yl-1H-1,2,4-triazol-1-yl}ethyl)-N-cyclopentyl-N'-(3,5-dimethylphenyl)urea | D |
| 145 | N-(2-{5-[3-chloro-4-(methyloxy)phenyl]-3-pyridin-4-yl-1H-1,2,4-triazol-1-yl}ethyl)-N-cyclopentyl-N'-[5-methyl-2-(methyloxy)phenyl]urea | D |
| 146 | N-(2-{5-[3-chloro-4-(methyloxy)phenyl]-3-pyridin-4-yl-1H-1,2,4-triazol-1-yl}ethyl)-N-cyclopentyl-N'-(4-iodophenyl)urea | D |
| 147 | N-(2-{5-[3-chloro-4-(methyloxy)phenyl]-3-pyridin-4-yl-1H-1,2,4-triazol-1-yl}ethyl)-N-cyclopentyl-N'-[4-(phenyloxy)phenyl]urea | D |
| 148 | N-(2-{5-[3-chloro-4-(methyloxy)phenyl]-3-pyridin-4-yl-1H-1,2,4-triazol-1-yl}ethyl)-N-cyclopentyl-N'-(2,4,6-trimethylphenyl)urea | D |
| 149 | N-(2-{5-[3-chloro-4-(methyloxy)phenyl]-3-pyridin-4-yl-1H-1,2,4-triazol-1-yl}ethyl)-N'-(5-chloro-2-methylphenyl)-N-cyclopentylurea | C |
| 150 | N-(2-{5-[3-chloro-4-(methyloxy)phenyl]-3-pyridin-4-yl-1H-1,2,4-triazol-1-yl}ethyl)-N'-(4-chloro-2-methylphenyl)-N-cyclopentylurea | C |
| 151 | N-(2-{5-[3-chloro-4-(methyloxy)phenyl]-3-pyridin-4-yl-1H-1,2,4-triazol-1-yl}ethyl)-N'-(2-chloro-6-methylphenyl)-N-cyclopentylurea | D |
| 152 | N-(2-{5-[3-chloro-4-(methyloxy)phenyl]-3-pyridin-4-yl-1H-1,2,4-triazol-1-yl}ethyl)-N'-(3-chloro-2-methylphenyl)-N-cyclopentylurea | B |
| 153 | N'-(3-chloro-4-fluorophenyl)-N-(2-{5-[3-chloro-4-(methyloxy)phenyl]-3-pyridin-4-yl-1H-1,2,4-triazol-1-yl}ethyl)-N-cyclopentylurea | D |
| 154 | N-(2-{5-[3-chloro-4-(methyloxy)phenyl]-3-pyridin-4-yl-1H-1,2,4-triazol-1-yl}ethyl)-N-cyclopentyl-N'-[2-(methylthio)phenyl]urea | D |
| 155 | N-(2-{5-[3-chloro-4-(methyloxy)phenyl]-3-pyridin-4-yl-1H-1,2,4-triazol-1-yl}ethyl)-N-cyclopentyl-N'-[3-(trifluoromethyl)phenyl]urea | D |
| 156 | N-(2-{5-[3-chloro-4-(methyloxy)phenyl]-3-pyridin-4-yl-1H-1,2,4-triazol-1-yl}ethyl)-N-cyclopentyl-N'-prop-2-en-1-ylurea | D |
| 157 | N-(2-{5-[3-chloro-4-(methyloxy)phenyl]-3-pyridin-4-yl-1H-1,2,4-triazol-1-yl}ethyl)-N-cyclopentyl-N'-[2-(1-methylethyl)phenyl]urea | D |

TABLE 2-continued

| Entry | Name | IC$_{50}$ |
|---|---|---|
| 158 | N-(2-{5-[3-chloro-4-(methyloxy)phenyl]-3-pyridin-4-yl-1H-1,2,4-triazol-1-yl}ethyl)-N-cyclopentyl-N'-(5-fluoro-2-methylphenyl)urea | C |
| 159 | N-(2-{5-[3-chloro-4-(methyloxy)phenyl]-3-pyridin-4-yl-1H-1,2,4-triazol-1-yl}ethyl)-N-cyclopentyl-N'-(3,4-difluorophenyl)urea | C |
| 160 | N-[2-(5-methyl-3-pyridin-4-yl-1H-1,2,4-triazol-1-yl)ethyl]-N-(2-morpholin-4-ylethyl)-2-naphthalen-1-ylacetamide | D |
| 161 | N-cyclopentyl-N-(2-{5-methyl-3-[2-(methylamino)pyrimidin-4-yl]-1H-1,2,4-triazol-1-yl}ethyl)-2-naphthalen-1-ylacetamide | D |
| 162 | N-{2-[3-(2,1,3-benzothiadiazol-5-yl)-5-methyl-1H-1,2,4-triazol-1-yl]ethyl}-N-cyclopentyl-2-naphthalen-1-ylacetamide | B |
| 163 | N-cyclopentyl-N-{2-[5-methyl-3-(2-morpholin-4-ylpyridin-4-yl)-1H-1,2,4-triazol-1-yl]ethyl}-2-naphthalen-1-ylacetamide | C |
| 164 | N-cyclopentyl-N-{2-[3-(2-{[2-(dimethylamino)ethyl]amino}pyridin-4-yl)-5-methyl-1H-1,2,4-triazol-1-yl]ethyl}-2-naphthalen-1-ylacetamide | B |
| 165 | N-cyclopentyl-N-(2-{5-methyl-3-[2-(phenylamino)pyridin-4-yl]-1H-1,2,4-triazol-1-yl}ethyl)-2-naphthalen-1-ylacetamide | B |
| 166 | N-cyclopentyl-N-(2-{3-[2-(ethylamino)pyridin-4-yl]-5-methyl-1H-1,2,4-triazol-1-yl}ethyl)-2-naphthalen-1-ylacetamide | A |
| 167 | N-cyclopentyl-N-(2-{5-methyl-3-[2-(methylamino)pyridin-4-yl]-1H-1,2,4-triazol-1-yl}ethyl)-2-naphthalen-1-ylacetamide | A |
| 168 | N-cyclopropyl-N-[2-(5-methyl-3-pyridin-4-yl-1H-1,2,4-triazol-1-yl)ethyl]-2-naphthalen-1-ylacetamide | B |
| 169 | N-[2-(5-methyl-3-pyridin-4-yl-1H-1,2,4-triazol-1-yl)ethyl]-2-naphthalen-1-yl-N-(2-pyrrolidin-1-ylethyl)acetamide | D |
| 170 | N-[2-(dimethylamino)ethyl]-N-[2-(5-methyl-3-pyridin-4-yl-1H-1,2,4-triazol-1-yl)ethyl]-2-naphthalen-1-ylacetamide | C |
| 171 | N-[2-(5-methyl-3-pyridin-4-yl-1H-1,2,4-triazol-1-yl)ethyl]-2-naphthalen-1-yl-N-(tetrahydro-2H-pyran-4-yl)acetamide | B |
| 172 | N-cyclopentyl-N-[2-(5-methyl-3-{2-[(phenylmethyl)amino]pyridin-4-yl}-1H-1,2,4-triazol-1-yl)ethyl]-2-naphthalen-1-ylacetamide | B |
| 173 | N-(2-{3-[2-(butylamino)pyridin-4-yl]-5-methyl-1H-1,2,4-triazol-1-yl}ethyl)-N-cyclopentyl-2-naphthalen-1-ylacetamide | A |
| 174 | N-cyclopentyl-N-[2-(5-methyl-3-{2-[(2-morpholin-4-ylethyl)amino]pyridin-4-yl}-1H-1,2,4-triazol-1-yl)ethyl]-2-naphthalen-1-ylacetamide | A |
| 175 | N-cyclopentyl-N-{2-[5-methyl-3-(2-{[2-(methyloxy)ethyl]amino}pyridin-4-yl)-1H-1,2,4-triazol-1-yl]ethyl}-2-naphthalen-1-ylacetamide | A |
| 176 | N-{2-[3-(2-aminopyridin-4-yl)-5-methyl-1H-1,2,4-triazol-1-yl]ethyl}-N-cyclopentyl-2-naphthalen-1-ylacetamide | A |
| 177 | N-(1-methylethyl)-N-[2-(5-methyl-3-pyridin-4-yl-1H-1,2,4-triazol-1-yl)ethyl]-2-naphthalen-1-ylacetamide | A |
| 178 | N-[2-(5-methyl-3-pyridin-4-yl-1H-1,2,4-triazol-1-yl)ethyl]-2-naphthalen-1-yl-N-(2-piperidin-1-ylethyl)acetamide | D |
| 179 | N-cyclohexyl-N-[2-(5-methyl-3-pyridin-4-yl-1H-1,2,4-triazol-1-yl)ethyl]-2-naphthalen-1-ylacetamide | A |
| 180 | N-[2-(5-methyl-3-pyridin-4-yl-1H-1,2,4-triazol-1-yl)ethyl]-2-naphthalen-1-yl-N-(tetrahydrofuran-2-ylmethyl)acetamide | B |
| 181 | N-cyclopentyl-N-(2-{5-methyl-3-[2-(piperidin-3-ylamino)pyridin-4-yl]-1H-1,2,4-triazol-1-yl}ethyl)-2-naphthalen-1-ylacetamide | B |
| 182 | N-cyclopentyl-N-[2-(5-methyl-3-{2-[(3R)-pyrrolidin-3-ylamino]pyridin-4-yl}-1H-1,2,4-triazol-1-yl)ethyl]-2-naphthalen-1-ylacetamide | B |
| 183 | N-cyclopentyl-N-[2-(5-methyl-3-{2-[(2-piperidin-1-ylethyl)amino]pyrimidin-4-yl}-1H-1,2,4-triazol-1-yl)ethyl]-2-naphthalen-1-ylacetamide | A |
| 184 | N-cyclopentyl-N-[2-(5-methyl-3-{2-[(phenylmethyl)amino]pyrimidin-4-yl}-1H-1,2,4-triazol-1-yl)ethyl]-2-naphthalen-1-ylacetamide | B |
| 185 | N-{2-[3-(2-amino-6-chloropyridin-4-yl)-5-methyl-1H-1,2,4-triazol-1-yl]ethyl}-N-cyclopentyl-2-naphthalen-1-ylacetamide | B |
| 186 | N-cyclopentyl-N-{2-[3-(2,6-diaminopyridin-4-yl)-5-methyl-1H-1,2,4-triazol-1-yl]ethyl}-2-naphthalen-1-ylacetamide | B |
| 187 | N-(2-{3-[2-amino-6-(ethyloxy)pyridin-4-yl]-5-methyl-1H-1,2,4-triazol-1-yl}ethyl)-N-cyclopentyl-2-naphthalen-1-ylacetamide | C |
| 188 | N-(2-{5-[3-chloro-4-(methyloxy)phenyl]-3-pyridin-4-yl-1H-1,2,4-triazol-1-yl}ethyl)-N-cyclopentyl-2-{[2-(methyloxy)phenyl]oxy}acetamide | B |
| 189 | N-(2-{5-[3-chloro-4-(methyloxy)phenyl]-3-pyridin-4-yl-1H-1,2,4-triazol-1-yl}ethyl)-N-cyclopentyl-2-[(2-methylphenyl)oxy]acetamide | B |
| 190 | N-(2-{5-[3-chloro-4-(methyloxy)phenyl]-3-pyridin-4-yl-1H-1,2,4-triazol-1-yl}ethyl)-N-cyclopentyl-2-[(2,5-dimethylphenyl)oxy]acetamide | B |
| 191 | N-(2-{5-[3-chloro-4-(methyloxy)phenyl]-3-pyridin-4-yl-1H-1,2,4-triazol-1-yl}ethyl)-N-cyclopentyl-2-[(3-methylphenyl)oxy]acetamide | B |
| 192 | N-(2-{5-[3-chloro-4-(methyloxy)phenyl]-3-pyridin-4-yl-1H-1,2,4-triazol-1-yl}ethyl)-N-cyclopentyl-2-(phenylthio)acetamide | C |
| 193 | N-(2-{5-[3-chloro-4-(methyloxy)phenyl]-3-pyridin-4-yl-1H-1,2,4-triazol-1-yl}ethyl)-N-cyclopentyl-2-(3,5-dimethylphenyl)acetamide | C |
| 194 | N-(2-{5-[3-chloro-4-(methyloxy)phenyl]-3-pyridin-4-yl-1H-1,2,4-triazol-1-yl}ethyl)-N-cyclopentyl-3-oxo-2,3-dihydro-1H-indene-1-carboxamide | C |
| 195 | N-(2-{5-[3-chloro-4-(methyloxy)phenyl]-3-pyridin-4-yl-1H-1,2,4-triazol-1-yl}ethyl)-2-[(2-chlorophenyl)oxy]-N-cyclopentylacetamide | B |
| 196 | N-(2-{5-[3-chloro-4-(methyloxy)phenyl]-3-pyridin-4-yl-1H-1,2,4-triazol-1-yl}ethyl)-N-cyclopentyl-2-[(2-nitrophenyl)oxy]acetamide | C |

TABLE 2-continued

| Entry | Name | IC$_{50}$ |
|---|---|---|
| 197 | N-cyclopentyl-N-{2-[5-methyl-3-(2-{[(3R)-pyrrolidin-3-ylmethyl]amino}pyridin-4-yl)-1H-1,2,4-triazol-1-yl]ethyl}-2-naphthalen-1-ylacetamide | B |
| 198 | N-cyclopentyl-N-{2-[5-methyl-3-(2-{[(3S)-pyrrolidin-3-ylmethyl]amino}pyridin-4-yl)-1H-1,2,4-triazol-1-yl]ethyl}-2-naphthalen-1-ylacetamide | B |
| 199 | N-[4-(1-{2-[cyclopentyl(naphthalen-1-ylacetyl)amino]ethyl}-5-methyl-1H-1,2,4-triazol-3-yl)pyridin-2-yl]-N~2~,N~2~-dimethylglycinamide | A |
| 200 | N-cyclopentyl-N-{2-[5-methyl-3-(2-{[(methyloxy)acetyl]amino}pyridin-4-yl)-1H-1,2,4-triazol-1-yl]ethyl}-2-naphthalen-1-ylacetamide | A |
| 201 | N-[4-(1-{2-[cyclopentyl(naphthalen-1-ylacetyl)amino]ethyl}-5-methyl-1H-1,2,4-triazol-3-yl)pyridin-2-yl]propanamide | A |
| 202 | N-cyclopentyl-N-[2-(5-methyl-3-{2-[(phenylacetyl)amino]pyridin-4-yl}-1H-1,2,4-triazol-1-yl)ethyl]-2-naphthalen-1-ylacetamide | A |
| 203 | N-[4-(1-{2-[cyclopentyl(naphthalen-1-ylacetyl)amino]ethyl}-5-methyl-1H-1,2,4-triazol-3-yl)pyridin-2-yl]benzamide | B |
| 204 | N-(2-{3-[2-(acetylamino)pyridin-4-yl]-5-methyl-1H-1,2,4-triazol-1-yl}ethyl)-N-cyclopentyl-2-naphthalen-1-ylacetamide | A |
| 205 | 2-(5-bromo-1H-indol-3-yl)-N-cyclopentyl-N-[2-(5-methyl-3-pyridin-4-yl-1H-1,2,4-triazol-1-yl)ethyl]acetamide | B |
| 206 | N-cyclopentyl-2-[5-(methyloxy)-1H-indol-3-yl]-N-[2-(5-methyl-3-pyridin-4-yl-1H-1,2,4-triazol-1-yl)ethyl]acetamide | C |
| 207 | N-cyclopentyl-2-(1H-indol-3-yl)-N-[2-(5-methyl-3-pyridin-4-yl-1H-1,2,4-triazol-1-yl)ethyl]acetamide | B |
| 208 | methyl [4-(1-{2-[cyclopentyl(naphthalen-1-ylacetyl)amino]ethyl}-5-methyl-1H-1,2,4-triazol-3-yl)pyridin-2-yl]carbamate | A |
| 209 | phenylmethyl [4-(1-{2-[cyclopentyl(naphthalen-1-ylacetyl)amino]ethyl}-5-methyl-1H-1,2,4-triazol-3-yl)pyridin-2-yl]carbamate | A |
| 210 | propyl [4-(1-{2-[cyclopentyl(naphthalen-1-ylacetyl)amino]ethyl}-5-methyl-1H-1,2,4-triazol-3-yl)pyridin-2-yl]carbamate | A |
| 211 | N-[4-(1-{2-[cyclopentyl(naphthalen-1-ylacetyl)amino]ethyl}-5-methyl-1H-1,2,4-triazol-3-yl)pyridin-2-yl]furan-3-carboxamide | A |
| 212 | N-cyclopentyl-N-[2-(5-methyl-3-{2-[(methylsulfonyl)amino]pyridin-4-yl}-1H-1,2,4-triazol-1-yl)ethyl]-2-naphthalen-1-ylacetamide | B |
| 213 | N-cyclopentyl-N-[2-(5-methyl-3-{2-[(phenylsulfonyl)amino]pyridin-4-yl}-1H-1,2,4-triazol-1-yl)ethyl]-2-naphthalen-1-ylacetamide | B |
| 214 | N-cyclopentyl-N-{2-[5-methyl-3-(2-{[(phenylmethyl)sulfonyl]amino}pyridin-4-yl)-1H-1,2,4-triazol-1-yl]ethyl}-2-naphthalen-1-ylacetamide | C |
| 215 | N-cyclopentyl-N-(2-{5-methyl-3-[2-({[(phenylmethyl)amino]carbonyl}amino)pyridin-4-yl]-1H-1,2,4-triazol-1-yl}ethyl)-2-naphthalen-1-ylacetamide | A |
| 216 | N-[4-(1-{2-[cyclopentyl(naphthalen-1-ylacetyl)amino]ethyl}-5-methyl-1H-1,2,4-triazol-3-yl)pyridin-2-yl]-1-ethylpiperidine-4-carboxamide | A |
| 217 | N-cyclopentyl-2-(2-methyl-3H-indol-3-yl)-N-[2-(5-methyl-3-pyridin-4-yl-1H-1,2,4-triazol-1-yl)ethyl]acetamide | B |
| 218 | N-cyclopentyl-N-[2-(5-methyl-3-pyridin-4-yl-1H-1,2,4-triazol-1-yl)ethyl]-2-naphthalen-1-ylpropanamide | B |
| 219 | N-[4-(1-{2-[cyclopentyl(naphthalen-1-ylacetyl)amino]ethyl}-5-methyl-1H-1,2,4-triazol-3-yl)pyridin-2-yl]-N~3~,N~3~-dimethyl-beta-alaninamide | A |
| 220 | N-[4-(1-{2-[cyclopentyl(naphthalen-1-ylacetyl)amino]ethyl}-5-methyl-1H-1,2,4-triazol-3-yl)pyridin-2-yl]pentanamide | A |
| 221 | N-{2-[3-(2-aminopyrimidin-4-yl)-5-methyl-1H-1,2,4-triazol-1-yl]ethyl}-N-cyclopentyl-2-naphthalen-1-ylacetamide | A |
| 222 | N-[4-(1-{2-[cyclopentyl(naphthalen-1-ylacetyl)amino]ethyl}-5-methyl-1H-1,2,4-triazol-3-yl)pyridin-2-yl]-1-methylpiperidine-3-carboxamide | A |
| 223 | 2-(4-methylpiperazin-1-yl)ethyl [4-(1-{2-[cyclopentyl(naphthalen-1-ylacetyl)amino]ethyl}-5-methyl-1H-1,2,4-triazol-3-yl)pyridin-2-yl]carbamate | A |
| 224 | 2-(methyloxy)ethyl [4-(1-{2-[cyclopentyl(naphthalen-1-ylacetyl)amino]ethyl}-5-methyl-1H-1,2,4-triazol-3-yl)pyridin-2-yl]carbamate | A |
| 225 | 2-morpholin-4-ylethyl [4-(1-{2-[cyclopentyl(naphthalen-1-ylacetyl)amino]ethyl}-5-methyl-1H-1,2,4-triazol-3-yl)pyridin-2-yl]carbamate | A |
| 226 | N-{2-[5-(2-aminopyrimidin-4-yl)-3-methyl-1H-1,2,4-triazol-1-yl]ethyl}-N-cyclopentyl-2-naphthalen-1-ylacetamide | D |
| 227 | methyl {4-[1-(2-{cyclopropyl[(naphthalen-1-ylamino)carbonyl]amino}ethyl)-1H-1,2,4-triazol-3-yl]pyridin-2-yl}carbamate | B |
| 228 | methyl [4-(1-{2-[{[(3-chloro-2-methylphenyl)amino]carbonyl}(cyclopentyl)amino]ethyl}-5-methyl-1H-1,2,4-triazol-3-yl)pyridin-2-yl]carbamate | B |
| 229 | methyl {4-[1-(2-{cyclopentyl[(naphthalen-1-ylamino)carbonyl]amino}ethyl)-5-methyl-1H-1,2,4-triazol-3-yl]pyridin-2-yl}carbamate | A |
| 230 | 2-piperidin-1-ylethyl [4-(1-{2-[cyclopentyl(naphthalen-1-ylacetyl)amino]ethyl}-5-methyl-1H-1,2,4-triazol-3-yl)pyridin-2-yl]carbamate | A |
| 231 | N-{2-[3-(2-aminopyrimidin-4-yl)-5-(trifluoromethyl)-1H-1,2,4-triazol-1-yl]ethyl}-N-cyclopentyl-2-naphthalen-1-ylacetamide | A |
| 232 | N-{2-[5-(2-aminopyrimidin-4-yl)-3-(trifluoromethyl)-1H-1,2,4-triazol-1-yl]ethyl}-N-cyclopentyl-2-naphthalen-1-ylacetamide | D |
| 233 | N-cyclopentyl-N-[2-(5-methyl-3-pyrimidin-4-yl-1H-1,2,4-triazol-1-yl)ethyl]-2-naphthalen-1-ylacetamide | B |
| 234 | N-{2-[3-(2-aminopyrimidin-4-yl)-1H-1,2,4-triazol-1-yl]ethyl}-N-cyclopentyl-2-naphthalen-1-ylacetamide | A |

TABLE 2-continued

| Entry | Name | IC$_{50}$ |
|---|---|---|
| 235 | methyl (4-{1-[2-(cyclopentyl{[(2-ethylphenyl)amino]carbonyl}amino)ethyl]-5-methyl-1H-1,2,4-triazol-3-yl}pyridin-2-yl)carbamate | C |
| 236 | methyl [4-(1-{2-[{[(3-bromo-2-methylphenyl)amino]carbonyl}(cyclopentyl)amino]ethyl}-5-methyl-1H-1,2,4-triazol-3-yl)pyridin-2-yl]carbamate | B |
| 237 | methyl [4-(1-{2-[cyclopentyl({[4-fluoro-2-(trifluoromethyl)phenyl]amino}carbonyl)amino]ethyl}-5-methyl-1H-1,2,4-triazol-3-yl)pyridin-2-yl]carbamate | C |
| 238 | methyl (4-{1-[2-(cyclopentyl{[(2-methylphenyl)amino]carbonyl}amino)ethyl]-5-methyl-1H-1,2,4-triazol-3-yl}pyridin-2-yl)carbamate | C |
| 239 | methyl (4-{1-[2-(cyclopentyl{[(3-fluoro-2-methylphenyl)amino]carbonyl}amino)ethyl]-5-methyl-1H-1,2,4-triazol-3-yl}pyridin-2-yl)carbamate | B |
| 240 | methyl (4-{1-[2-(cyclopentyl{[(4-fluoro-2-methylphenyl)amino]carbonyl}amino)ethyl]-5-methyl-1H-1,2,4-triazol-3-yl}pyridin-2-yl)carbamate | B |
| 241 | methyl [4-(1-{2-[cyclopentyl(phenylacetyl)amino]ethyl}-5-ethyl-1H-1,2,4-triazol-3-yl)pyridin-2-yl]carbamate | B |
| 242 | methyl {4-[1-{2-[cyclopentyl(naphthalen-1-ylacetyl)amino]ethyl}-5-(trifluoromethyl)-1H-1,2,4-triazol-3-yl]pyridin-2-yl}carbamate | A |
| 243 | methyl [4-(1-{2-[acetyl(cyclopropyl)amino]ethyl}-5-ethyl-1H-1,2,4-triazol-3-yl)pyridin-2-yl]carbamate | D |
| 244 | methyl [4-(1-{2-[acetyl(cyclopentyl)amino]ethyl}-5-ethyl-1H-1,2,4-triazol-3-yl)pyridin-2-yl]carbamate | C |
| 245 | 2-(4-methylpiperazin-1-yl)ethyl {4-[1-(2-{cyclopentyl[(naphthalen-1-ylamino)carbonyl]amino}ethyl)-5-methyl-1H-1,2,4-triazol-3-yl]pyridin-2-yl}carbamate | A |

What is claimed is:

1. A method of treating a Tie-2 kinase-dependent disease or condition comprising administering to a mammal in need of such treatment a therapeutically effective amount of a compound according to one of the following formulae,

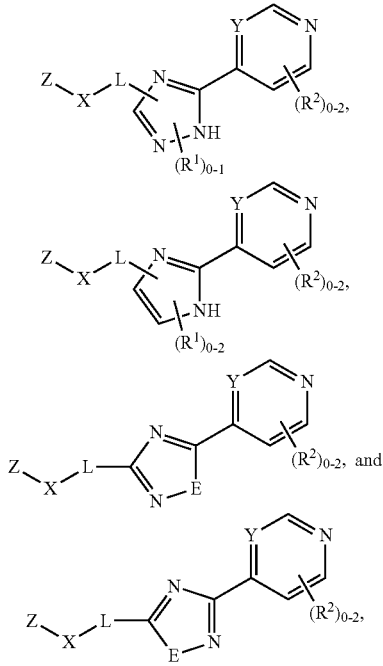

wherein E is —S— or —O—,
or a pharmaceutically acceptable salt thereof, wherein,
$R^1$ and $R^2$, at each occurrence, are independently selected from —H, halogen, —CN, —NH$_2$, —CF$_3$, —NO$_2$, —OR$^6$, —N(R$^6$)R$^7$, —N(R$^6$)N(R$^6$)R$^7$, —S(O)$_{0-2}$R$^7$, —SO$_2$N(R$^6$)R$^7$, —CO$_2$R$^6$, —C(O)N(R$^6$)R$^7$, —N(R$^6$)SO$_2$R$^7$, —N(R$^6$)C(O)R$^7$, —N(R$^6$)C(O)C$_{0-6}$alkyl-N(R$^6$)R$^7$, —N(R$^6$)CO$_2$R$^7$, —C(O)R$^6$, optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl;

L is optionally substituted C$_{1-4}$ alkylene;

X is —N(R$^3$)—;

R$^3$ is selected from —H or optionally substituted alkyl;

Z is R$^4$C(=O)— or R$^4$SO$_2$—;

R$^4$ is selected from optionally substituted aryl, optionally substituted aryl C$_{1-6}$ alkyl, optionally substituted heterocyclyl, and optionally substituted heterocyclyl C$_{1-6}$ alkyl;

optionally R$^3$ and R$^4$, together with the atoms to which they are attached and any additional atoms that link Z with X, are combined to form a first optionally substituted five- to seven-membered heterocyclyl ring, said first optionally substituted five- to seven-membered heterocyclyl ring optionally containing at least one additional heteroatom selected from N, O, S, and P;

R$^5$ is selected from —H, —NO$_2$, —NH$_2$, —N(R$^6$)R$^7$, —CN, —OR$^6$, and optionally substituted C$_{1-6}$ alkyl;

Y is independently either =C(H)— or =N—, provided that there are no more than three of =N— in the ring bearing Y;

each R$^6$ is —H or R$^7$;

each R$^7$ is independently selected from optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl; and optionally R$^6$ and R$^7$, when taken together with a common nitrogen to which they are attached, form a second optionally substituted five- to seven-membered heterocyclyl ring, said second optionally substituted five- to seven-membered heterocyclyl ring optionally containing at least one additional heteroatom selected from N, O, S, and P.

2. The method according to claim 1, wherein the compound is according to one of,

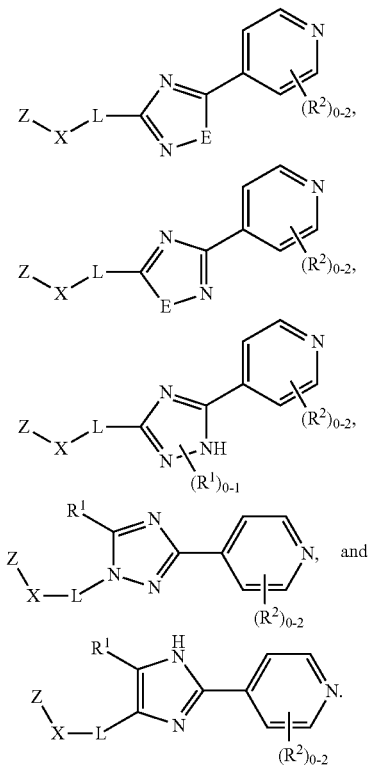

3. The method according to claim 2, wherein $R^4$ is either optionally substituted aryl $C_{1-6}$ alkyl or optionally substituted heteroaryl $C_{1-6}$ alkyl.

4. The method according to claim 3, wherein $R^1$ is selected from —H, optionally substituted $C_{1-6}$ alkyl, optionally substituted aryl, and optionally substituted heteroaryl.

5. The method according to claim 4, wherein L is optionally substituted —$CH_2CH_2$—.

6. The method according to claim 5, wherein $R^3$ is optionally substituted cycloalkyl or optionally substituted branched alkyl.

7. The method according to claim 6, wherein Z is $R^4C(=O)$—.

8. The method according to claim 7, wherein L is —$CH_2CH_2$—.

9. The method according to claim 8, wherein $R^4$ is optionally substituted aryl $C_{1-6}$ alkyl.

10. The method according to claim 9, wherein $R^4$ is optionally substituted —$CH_2$-naphthylene.

11. The method according to claim 10, wherein $R^4$ is optionally substituted —$CH_2$-1-naphthylene.

12. The method according to claim 11, wherein $R^4$ is —$CH_2$-1-naphthylene.

13. The method according to claim 12, wherein at least one of $R^2$ is selected from —$NH_2$, —$N(R^6)R^7$, —$N(R^6)N(R^6)R^7$, —$N(R^6)C(O)R^7$, —$N(R^6)C(O)C_{0-6}$alkyl-$N(R^6)R^7$, and —$N(R^6)CO_2R^7$.

14. The method according to claim 13, wherein said at least one of $R^2$ is ortho to the nitrogen of the pyridine ring bearing $R^2$.

15. A method of treating a Tie-2 kinase-dependent disease or condition comprising administering to a mammal in need of such treatment a therapeutically effective amount of a compound, wherein the compound is selected from Table 3, or a pharmaceutically acceptable salt thereof:

TABLE 3

| Entry | Name |
|---|---|
| 1 | N-{2-[5-(3-chloro-4-hydroxyphenyl)-3-pyridin-4-yl-1H-1,2,4-triazol-1-yl]ethyl}-N-cyclopentyl-2-naphthalen-1-ylacetamide |
| 2 | ethyl {5-[3-chloro-4-(methyloxy)phenyl]-3-pyridin-4-yl-1H-1,2,4-triazol-1-yl}acetate |
| 3 | 2-{5-[3-chloro-4-(methyloxy)phenyl]-3-pyridin-4-yl-1H-1,2,4-triazol-1-yl}-N-cyclopentylacetamide |
| 4 | ethyl {3-[3-chloro-4-(methyloxy)phenyl]-5-pyridin-4-yl-1H-1,2,4-triazol-1-yl}acetate |
| 5 | 2-{3-[3-chloro-4-(methyloxy)phenyl]-5-pyridin-4-yl-1H-1,2,4-triazol-1-yl}-N-cyclopentylacetamide |
| 6 | methyl 3-{5-[3-chloro-4-(methyloxy)phenyl]-3-pyridin-4-yl-1H-1,2,4-triazol-1-yl}propanoate |
| 7 | methyl 3-{3-[3-chloro-4-(methyloxy)phenyl]-5-pyridin-4-yl-1H-1,2,4-triazol-1-yl}propanoate |
| 8 | N-(3-{5-[3-chloro-4-(methyloxy)phenyl]-3-pyridin-4-yl-1H-1,2,4-triazol-1-yl}propyl)-N-cyclopentyl-2-naphthalen-1-ylacetamide |
| 9 | N-(3-{3-[3-chloro-4-(methyloxy)phenyl]-5-pyridin-4-yl-1H-1,2,4-triazol-1-yl}propyl)-N-cyclopentyl-2-naphthalen-1-ylacetamide |
| 10 | N-(2-{5-[3-chloro-4-(methyloxy)phenyl]-3-pyridin-4-yl-1H-1,2,4-triazol-1-yl}ethyl)-N-cyclopentyl-2-naphthalen-1-ylacetamide |
| 11 | N-{2-[3-(3-chloro-4-hydroxyphenyl)-5-pyridin-4-yl-1H-1,2,4-triazol-1-yl]ethyl}-N-cyclopentyl-2-naphthalen-1-ylacetamide |
| 12 | 2-{3-[3-chloro-4-(methyloxy)phenyl]-5-pyridin-3-yl-1H-1,2,4-triazol-1-yl}-N-cyclopentylacetamide |
| 13 | N-(2-{5-[3-chloro-4-(methyloxy)phenyl]-3-pyridin-3-yl-1H-1,2,4-triazol-1-yl}ethyl)-N-cyclopentyl-2-naphthalen-1-ylacetamide |
| 14 | ethyl [5-(4-nitrophenyl)-3-pyridin-4-yl-1H-1,2,4-triazol-1-yl]acetate |
| 15 | ethyl [5-(3,5-dichlorophenyl)-3-pyridin-4-yl-1H-1,2,4-triazol-1-yl]acetate |
| 16 | ethyl [3-(3,5-dichlorophenyl)-5-pyridin-4-yl-1H-1,2,4-triazol-1-yl]acetate |
| 17 | N-cyclopentyl-N-[2-(5-furan-2-yl-3-pyridin-4-yl-1H-1,2,4-triazol-1-yl)ethyl]-2-naphthalen-1-ylacetamide |
| 18 | N-cyclopentyl-N-[2-(3-furan-2-yl-5-pyridin-4-yl-1H-1,2,4-triazol-1-yl)ethyl]-2-naphthalen-1-ylacetamide |

TABLE 3-continued

| Entry | Name |
|---|---|
| 19 | N-cyclopentyl-2-naphthalen-1-yl-N-{2-[5-pyridin-4-yl-3-(2-thienyl)-1H-1,2,4-triazol-1-yl]ethyl}acetamide |
| 20 | N-(2-{5-[3-chloro-4-(methyloxy)phenyl]-3-pyridin-4-yl-1H-1,2,4-triazol-1-yl}ethyl)-N-cyclopentylnaphthalene-1-carboxamide |
| 21 | N-(2-{5-[3-chloro-4-(methyloxy)phenyl]-3-pyridin-4-yl-1H-1,2,4-triazol-1-yl}ethyl)-N-cyclopentylnaphthalene-2-carboxamide |
| 22 | N-cyclopentyl-N-(2-{5-[3-(methyloxy)phenyl]-3-pyridin-4-yl-1H-1,2,4-triazol-1-yl}ethyl)-2-naphthalen-1-ylacetamide |
| 23 | N-cyclopentyl-N-(2-{3-[3-(methyloxy)phenyl]-5-pyridin-4-yl-1H-1,2,4-triazol-1-yl}ethyl)-2-naphthalen-1-ylacetamide |
| 24 | N-(4-{5-[3-chloro-4-(methyloxy)phenyl]-3-pyridin-4-yl-1H-1,2,4-triazol-1-yl}butyl)-N-cyclopentyl-2-naphthalen-1-ylacetamide |
| 25 | N-(4-{3-[3-chloro-4-(methyloxy)phenyl]-5-pyridin-4-yl-1H-1,2,4-triazol-1-yl}butyl)-N-cyclopentyl-2-naphthalen-1-ylacetamide |
| 26 | N-(2-{5-[3-chloro-4-(methyloxy)phenyl]-3-pyridin-4-yl-1H-1,2,4-triazol-1-yl}ethyl)-N-cyclopentylbenzamide |
| 27 | N-(2-{3-[3-chloro-4-(methyloxy)phenyl]-5-pyridin-4-yl-1H-1,2,4-triazol-1-yl}ethyl)-N-cyclopentylbenzamide |
| 28 | N-(2-{5-[3-chloro-4-(methyloxy)phenyl]-3-pyridin-4-yl-1H-1,2,4-triazol-1-yl}ethyl)-N-cyclopentylquinoline-4-carboxamide |
| 29 | N-(2-{5-[3-chloro-4-(methyloxy)phenyl]-3-pyridin-4-yl-1H-1,2,4-triazol-1-yl}ethyl)-N-cyclopentyl-N'-naphthalen-1-ylurea |
| 30 | N-(2-{5-[3-chloro-4-(methyloxy)phenyl]-3-pyridin-4-yl-1H-1,2,4-triazol-1-yl}ethyl)-N-cyclopentyl-N'-phenylurea |
| 31 | N-(2-{5-[3-chloro-4-(methyloxy)phenyl]-3-pyridin-4-yl-1H-1,2,4-triazol-1-yl}ethyl)-N-cyclopentyl-2-phenylacetamide |
| 32 | N-(2-{5-[3-chloro-4-(methyloxy)phenyl]-3-phenyl-1H-1,2,4-triazol-1-yl}ethyl)-N-cyclopentyl-2-naphthalen-1-ylacetamide |
| 33 | 2-{5-[3-chloro-4-(methyloxy)phenyl]-3-phenyl-1H-1,2,4-triazol-1-yl}-N-cyclopentylacetamide |
| 34 | N-(2-{5-[3-chloro-4-(methyloxy)phenyl]-3-pyridin-4-yl-1H-1,2,4-triazol-1-yl}ethyl)-2-naphthalen-1-ylacetamide |
| 35 | N-(2-{3-[3-chloro-4-(methyloxy)phenyl]-5-pyridin-4-yl-1H-1,2,4-triazol-1-yl}ethyl)-N-(1-methylethyl)-2-naphthalen-1-ylacetamide |
| 36 | N-(2-{5-[3-chloro-4-(methyloxy)phenyl]-3-pyridin-4-yl-1H-1,2,4-triazol-1-yl}ethyl)-N-cyclohexyl-2-naphthalen-1-ylacetamide |
| 37 | N-(2-{3-[3-chloro-4-(methyloxy)phenyl]-5-pyridin-4-yl-1H-1,2,4-triazol-1-yl}ethyl)-N-cyclohexyl-2-naphthalen-1-ylacetamide |
| 38 | N-(2-{3-[3-chloro-4-(methyloxy)phenyl]-5-pyridin-4-yl-1H-1,2,4-triazol-1-yl}ethyl)-N-cyclopropyl-2-naphthalen-1-ylacetamide |
| 39 | N-cyclopentyl-N-(2-{5-[4-(methyloxy)phenyl]-3-pyridin-4-yl-1H-1,2,4-triazol-1-yl}ethyl)-2-naphthalen-1-ylacetamide |
| 40 | N-cyclopentyl-N-(2-{3-[4-(methyloxy)phenyl]-5-pyridin-4-yl-1H-1,2,4-triazol-1-yl}ethyl)-2-naphthalen-1-ylacetamide |
| 41 | N-(2-{5-[3,4-bis(methyloxy)phenyl]-3-pyridin-4-yl-1H-1,2,4-triazol-1-yl}ethyl)-N-cyclopentyl-2-naphthalen-1-ylacetamide |
| 42 | N-(2-{3-[3,4-bis(methyloxy)phenyl]-5-pyridin-4-yl-1H-1,2,4-triazol-1-yl}ethyl)-N-cyclopentyl-2-naphthalen-1-ylacetamide |
| 43 | N-cyclopentyl-N-[2-(5-methyl-3-pyridin-4-yl-1H-1,2,4-triazol-1-yl)ethyl]-2-naphthalen-1-ylacetamide |
| 44 | N-cyclopentyl-2-naphthalen-1-yl-N-[2-(3-pyridin-4-yl-1H-1,2,4-triazol-1-yl)ethyl]acetamide |
| 45 | N-cyclopentyl-2-naphthalen-1-yl-N-(2-{3-pyridin-4-yl-5-[3-(trifluoromethyl)phenyl]-1H-1,2,4-triazol-1-yl}ethyl)acetamide |
| 46 | N-cyclopentyl-2-naphthalen-1-yl-N-(2-{5-pyridin-4-yl-3-[3-(trifluoromethyl)phenyl]-1H-1,2,4-triazol-1-yl}ethyl)acetamide |
| 47 | N-cyclopentyl-N-{2-[5-(3,5-dichlorophenyl)-3-pyridin-4-yl-1H-1,2,4-triazol-1-yl]ethyl}-2-naphthalen-1-ylacetamide |
| 48 | N-(2-{5-[3-chloro-4-(methyloxy)phenyl]-3-pyridin-4-yl-1H-1,2,4-triazol-1-yl}ethyl)-N-cyclopentyl-2-naphthalen-2-ylacetamide |
| 49 | N-cyclopentyl-2-naphthalen-1-yl-N-[2-(5-pyridin-4-yl-1H-1,2,4-triazol-3-yl)ethyl]acetamide |
| 50 | N-cyclopentyl-2-naphthalen-1-yl-N-[2-(5-phenyl-3-pyridin-4-yl-1H-1,2,4-triazol-1-yl)ethyl]acetamide |
| 51 | N-cyclopentyl-2-naphthalen-1-yl-N-[2-(3-phenyl-5-pyridin-4-yl-1H-1,2,4-triazol-1-yl)ethyl]acetamide |
| 52 | N-cyclopentyl-2-naphthalen-1-yl-N-[2-(3-pyridin-4-yl-1,2,4-oxadiazol-5-yl)ethyl]acetamide |
| 53 | N-{2-[5-[3-chloro-4-(methyloxy)phenyl]-3-(2-chloropyridin-4-yl)-1H-1,2,4-triazol-1-yl]ethyl}-N-cyclopentyl-2-naphthalen-1-ylacetamide |
| 54 | N-cyclopentyl-N-(2-{4-[4-(methyloxy)phenyl]-2-pyridin-4-yl-1H-imidazol-5-yl}ethyl)-2-naphthalen-1-ylacetamide |
| 55 | N-(2-{3-[3-chloro-4-(methyloxy)phenyl]-5-pyridin-4-yl-1H-1,2,4-triazol-1-yl}ethyl)-N-cyclopentyl-N'-naphthalen-1-ylurea |
| 56 | N-cyclopentyl-N-{2-[5-(3-fluorophenyl)-3-pyridin-4-yl-1H-1,2,4-triazol-1-yl]ethyl}-2-naphthalen-1-ylacetamide |
| 57 | N-cyclopentyl-N-{2-[3-(3-fluorophenyl)-5-pyridin-4-yl-1H-1,2,4-triazol-1-yl]ethyl}-2-naphthalen-1-ylacetamide |

TABLE 3-continued

| Entry | Name |
|---|---|
| 58 | N-{2-[5-(3-chlorophenyl)-3-pyridin-4-yl-1H-1,2,4-triazol-1-yl]ethyl}-N-cyclopentyl-2-naphthalen-1-ylacetamide |
| 59 | N-{2-[3-(3-chlorophenyl)-5-pyridin-4-yl-1H-1,2,4-triazol-1-yl]ethyl}-N-cyclopentyl-2-naphthalen-1-ylacetamide |
| 60 | N-cyclopentyl-2-naphthalen-1-yl-N-[2-(5-piperidn-4-yl-3-pyridin-4-yl-1H-1,2,4-triazol-1-yl)ethyl]acetamide |
| 61 | N-{2-[5-(2-chlorophenyl)-3-pyridin-4-yl-1H-1,2,4-triazol-1-yl]ethyl}-N-cyclopentyl-2-naphthalen-1-ylacetamide |
| 62 | N-{2-[3-(2-chlorophenyl)-5-pyridin-4-yl-1H-1,2,4-triazol-1-yl]ethyl}-N-cyclopentyl-2-naphthalen-1-ylacetamide |
| 63 | N-{2-[5-(1,3-benzodioxol-5-yl)-3-pyridin-4-yl-1H-1,2,4-triazol-1-yl]ethyl}-N-cyclopentyl-2-naphthalen-1-ylacetamide |
| 64 | N-{2-[3-(1,3-benzodioxol-5-yl)-5-pyridin-4-yl-1H-1,2,4-triazol-1-yl]ethyl}-N-cyclopentyl-2-naphthalen-1-ylacetamide |
| 65 | N-{2-[5-(3-bromophenyl)-3-pyridin-4-yl-1H-1,2,4-triazol-1-yl]ethyl}-N-cyclopentyl-2-naphthalen-1-ylacetamide |
| 66 | N-{2-[3-(3-bromophenyl)-5-pyridin-4-yl-1H-1,2,4-triazol-1-yl]ethyl}-N-cyclopentyl-2-naphthalen-1-ylacetamide |
| 67 | N-{2-[5-(4-bromophenyl)-3-pyridin-4-yl-1H-1,2,4-triazol-1-yl]ethyl}-N-cyclopentyl-2-naphthalen-1-ylacetamide |
| 68 | N-{2-[3-(4-bromophenyl)-5-pyridin-4-yl-1H-1,2,4-triazol-1-yl]ethyl}-N-cyclopentyl-2-naphthalen-1-ylacetamide |
| 69 | N-cyclopentyl-N-[2-(5-methyl-3-pyridazin-4-yl-1H-1,2,4-triazol-1-yl)ethyl]-2-naphthalen-1-ylacetamide |
| 70 | N-cyclopentyl-N-{2-[5-(4-methylphenyl)-3-pyridin-4-yl-1H-1,2,4-triazol-1-yl]ethyl}-2-naphthalen-1-ylacetamide |
| 71 | N-cyclopentyl-N-{2-[3-(4-methylphenyl)-5-pyridin-4-yl-1H-1,2,4-triazol-1-yl]ethyl}-2-naphthalen-1-ylacetamide |
| 72 | N-cyclopentyl-N-{2-[5-(3-methylphenyl)-3-pyridin-4-yl-1H-1,2,4-triazol-1-yl]ethyl}-2-naphthalen-1-ylacetamide |
| 73 | N-cyclopentyl-N-{2-[3-(3-methylphenyl)-5-pyridin-4-yl-1H-1,2,4-triazol-1-yl]ethyl}-2-naphthalen-1-ylacetamide |
| 74 | N-cyclopentyl-N-{2-[5-(2,4-dichlorophenyl)-3-pyridin-4-yl-1H-1,2,4-triazol-1-yl]ethyl}-2-naphthalen-1-ylacetamide |
| 75 | N-cyclopentyl-N-{2-[3-(2,4-dichlorophenyl)-5-pyridin-4-yl-1H-1,2,4-triazol-1-yl]ethyl}-2-naphthalen-1-ylacetamide |
| 76 | N-cyclopentyl-2-naphthalen-1-yl-N-(2-{3-pyridin-4-yl-5-[4-(trifluoromethyl)phenyl]-1H-1,2,4-triazol-1-yl}ethyl)acetamide |
| 77 | N-cyclopentyl-2-naphthalen-1-yl-N-(2-{5-pyridin-4-yl-3-[4-(trifluoromethyl)phenyl]-1H-1,2,4-triazol-1-yl}ethyl)acetamide |
| 78 | N-(2-{5-[3-chloro-4-(methyloxy)phenyl]-3-pyridin-4-yl-1H-1,2,4-triazol-1-yl}ethyl)-N-cyclopropyl-2-naphthalen-1-ylacetamide |
| 79 | N-(2-{5-[3-chloro-4-(methyloxy)phenyl]-3-pyridin-4-yl-1H-1,2,4-triazol-1-yl}ethyl)-N-(1-methylethyl)-2-naphthalen-1-ylacetamide |
| 80 | N-cyclopentyl-N-[2-(5-ethyl-3-pyridin-4-yl-1H-1,2,4-triazol-1-yl)ethyl]-2-naphthalen-1-ylacetamide |
| 81 | N-(2-{5-[3-chloro-4-(methyloxy)phenyl]-3-pyridin-4-yl-1H-1,2,4-triazol-1-yl}ethyl)-N-(1-methylpiperidin-4-yl)-2-naphthalen-1-ylacetamide |
| 82 | N-(2-{5-[3-chloro-4-(methyloxy)phenyl]-3-pyridin-4-yl-1H-1,2,4-triazol-1-yl}ethyl)-N-cyclopentyl-N'-[(1R,2S)-2-phenylcyclopropyl]urea |
| 83 | N-(2-{5-[3-chloro-4-(methyloxy)phenyl]-3-pyridin-4-yl-1H-1,2,4-triazol-1-yl}ethyl)-N-cyclopentyl-N'-(2,4-dichlorophenyl)urea |
| 84 | N-(2-{5-[3-chloro-4-(methyloxy)phenyl]-3-pyridin-4-yl-1H-1,2,4-triazol-1-yl}ethyl)-N-cyclopentyl-N'-[2-(methyloxy)phenyl]urea |
| 85 | N'-[2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 86 | N-(2-{5-[3-chloro-4-(methyloxy)phenyl]-3-pyridin-4-yl-1H-1,2,4-triazol-1-yl}ethyl)-N-cyclopentyl-N'-(2-methylphenyl)urea |
| 87 | N-(2-{5-[3-chloro-4-(methyloxy)phenyl]-3-pyridin-4-yl-1H-1,2,4-triazol-1-yl}ethyl)-N-cyclopentyl-N'-(2-ethylphenyl)urea |
| 88 | N-(2-{5-[3-chloro-4-(methyloxy)phenyl]-3-pyridin-4-yl-1H-1,2,4-triazol-1-yl}ethyl)-N-cyclopentyl-N'-(3,4-dichlorophenyl)urea |
| 89 | N-(2-{5-[3-chloro-4-(methyloxy)phenyl]-3-pyridin-4-yl-1H-1,2,4-triazol-1-yl}ethyl)-N-cyclopentyl-N'-hexylurea |
| 90 | N-(2-{5-[3-chloro-4-(methyloxy)phenyl]-3-pyridin-4-yl-1H-1,2,4-triazol-1-yl}ethyl)-N-cyclopentyl-N'-(4-fluorophenyl)urea |
| 91 | N-(2-{5-[3-chloro-4-(methyloxy)phenyl]-3-pyridin-4-yl-1H-1,2,4-triazol-1-yl}ethyl)-N-cyclopentyl-N'-[4-(methyloxy)phenyl]urea |
| 92 | N-(2-{5-[3-chloro-4-(methyloxy)phenyl]-3-pyridin-4-yl-1H-1,2,4-triazol-1-yl}ethyl)-N-cyclopentyl-N'-(phenylmethyl)urea |
| 93 | N'-[3,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylurea |
| 94 | N-(2-{5-[3-chloro-4-(methyloxy)phenyl]-3-pyridin-4-yl-1H-1,2,4-triazol-1-yl}ethyl)-N-cyclopentyl-N'-[3,4,5-tris(methyloxy)phenyl]urea |
| 95 | N'-(3-acetylphenyl)-N-(2-{5-[3-chloro-4-(methyloxy)phenyl]-3-pyridin-4-yl-1H-1,2,4-triazol-1-yl}ethyl)-N-cyclopentylurea |
| 96 | N-(2-{5-[3-chloro-4-(methyloxy)phenyl]-3-pyridin-4-yl-1H-1,2,4-triazol-1-yl}ethyl)-N-cyclopentyl-N'-(3,4-dimethylphenyl)urea |

TABLE 3-continued

| Entry | Name |
|---|---|
| 97 | N-(2-{5-[3-chloro-4-(methyloxy)phenyl]-3-pyridin-4-yl-1H-1,2,4-triazol-1-yl}ethyl)-N'-[4-chloro-2-(trifluoromethyl)phenyl]-N-cyclopentylurea |
| 98 | N-(2-{5-[3-chloro-4-(methyloxy)phenyl]-3-pyridin-4-yl-1H-1,2,4-triazol-1-yl}ethyl)-N-cyclopentyl-N'-[4-(methylthio)phenyl]urea |
| 99 | N'-(4-acetylphenyl)-N-(2-{5-[3-chloro-4-(methyloxy)phenyl]-3-pyridin-4-yl-1H-1,2,4-triazol-1-yl}ethyl)-N-cyclopentylurea |
| 100 | N-(2-{5-[3-chloro-4-(methyloxy)phenyl]-3-pyridin-4-yl-1H-1,2,4-triazol-1-yl}ethyl)-N-cyclopentyl-N'-[4-(1-methylethyl)phenyl]urea |
| 101 | N-(2-{5-[3-chloro-4-(methyloxy)phenyl]-3-pyridin-4-yl-1H-1,2,4-triazol-1-yl}ethyl)-N'-(4-cyanophenyl)-N-cyclopentylurea |
| 102 | N'-biphenyl-2-yl-N-(2-{5-[3-chloro-4-(methyloxy)phenyl]-3-pyridin-4-yl-1H-1,2,4-triazol-1-yl}ethyl)-N-cyclopentylurea |
| 103 | N-(2-{5-[3-chloro-4-(methyloxy)phenyl]-3-pyridin-4-yl-1H-1,2,4-triazol-1-yl}ethyl)-N-cyclopentyl-N'-pentylurea |
| 104 | N-(2-{5-[3-chloro-4-(methyloxy)phenyl]-3-pyridin-4-yl-1H-1,2,4-triazol-1-yl}ethyl)-N-cyclopentyl-N'-heptylurea |
| 105 | N-(2-{5-[3-chloro-4-(methyloxy)phenyl]-3-pyridin-4-yl-1H-1,2,4-triazol-1-yl}ethyl)-N'-(3-chlorophenyl)-N-cyclopentylurea |
| 106 | N-(2-{5-[3-chloro-4-(methyloxy)phenyl]-3-pyridin-4-yl-1H-1,2,4-triazol-1-yl}ethyl)-N-cyclopentyl-N'-(3-methylphenyl)urea |
| 107 | N-(2-{5-[3-chloro-4-(methyloxy)phenyl]-3-pyridin-4-yl-1H-1,2,4-triazol-1-yl}ethyl)-N-cyclopentyl-N'-(1,1-dimethylethyl)urea |
| 108 | N-(2-{5-[3-chloro-4-(methyloxy)phenyl]-3-pyridin-4-yl-1H-1,2,4-triazol-1-yl}ethyl)-N-cyclopentyl-N'-(1-methylethyl)urea |
| 109 | N-(2-{5-[3-chloro-4-(methyloxy)phenyl]-3-pyridin-4-yl-1H-1,2,4-triazol-1-yl}ethyl)-N-cyclopentyl-N'-ethylurea |
| 110 | N-(2-{5-[3-chloro-4-(methyloxy)phenyl]-3-pyridin-4-yl-1H-1,2,4-triazol-1-yl}ethyl)-N-cyclopentyl-N'-propylurea |
| 111 | N-(2-{5-[3-chloro-4-(methyloxy)phenyl]-3-pyridin-4-yl-1H-1,2,4-triazol-1-yl}ethyl)-N-cyclopentyl-N'-[4-(ethyloxy)phenyl]urea |
| 112 | N-(2-{5-[3-chloro-4-(methyloxy)phenyl]-3-pyridin-4-yl-1H-1,2,4-triazol-1-yl}ethyl)-N-cyclopentyl-N'-(4-ethylphenyl)urea |
| 113 | N-(2-{5-[3-chloro-4-(methyloxy)phenyl]-3-pyridin-4-yl-1H-1,2,4-triazol-1-yl}ethyl)-N-cyclopentyl-N'-(2-phenylethyl)urea |
| 114 | N-(2-{5-[3-chloro-4-(methyloxy)phenyl]-3-pyridin-4-yl-1H-1,2,4-triazol-1-yl}ethyl)-N-cyclopentyl-N'-{1-methyl-1-[3-(1-methylethenyl)phenyl]ethyl}urea |
| 115 | N-(2-{5-[3-chloro-4-(methyloxy)phenyl]-3-pyridin-4-yl-1H-1,2,4-triazol-1-yl}ethyl)-N-cyclopentyl-N'-(2-fluorophenyl)urea |
| 116 | N-(2-{5-[3-chloro-4-(methyloxy)phenyl]-3-pyridin-4-yl-1H-1,2,4-triazol-1-yl}ethyl)-N-cyclopentyl-N'-(2,4-diflouorophenyl)urea |
| 117 | N-(2-{5-[3-chloro-4-(methyloxy)phenyl]-3-pyridin-4-yl-1H-1,2,4-triazol-1-yl}ethyl)-N-cyclopentyl-N'-(2,6-difluorophenyl)urea |
| 118 | N-(2-{5-[3-chloro-4-(methyloxy)phenyl]-3-pyridin-4-yl-1H-1,2,4-triazol-1-yl}ethyl)-N'-(2-chlorophenyl)-N-cyclopentylurea |
| 119 | N-(2-{5-[3-chloro-4-(methyloxy)phenyl]-3-pyridin-yl-1H-1,2,4-triazol-1-yl}ethyl)-N-cyclopentyl-N'-(2,3-dichlorophenyl)urea |
| 120 | N'-[2,5-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 121 | N-(2-{5-[3-chloro-4-(methyloxy)phenyl]-3-pyridin-4-yl-1H-1,2,4-triazol-1-yl}ethyl)-N-cyclopentyl-N'-[2-(ethyloxy)phenyl]urea |
| 122 | N-(2-{5-[3-chloro-4-(methyloxy)phenyl]-3-pyridin-4-yl-1H-1,2,4-triazol-1-yl}ethyl)-N-cyclopentyl-N'-[2-(trifluoromethyl)phenyl]urea |
| 123 | N-(2-{5-[3-chloro-4-(methyloxy)phenyl]-3-pyridin-4-yl-1H-1,2,4-triazol-1-yl}ethyl)-N-cyclopentyl-N'-(2,6-dimethylphenyl)urea |
| 124 | N-(2-{5-[3-chloro-4-(methyloxy)phenyl]-3-pyridin-4-yl-1H-1,2,4-triazol-1-yl}ethyl)-N-cyclopentyl-N'-[4-(trifluoromethyl)phenyl]urea |
| 125 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]urea |
| 126 | N-(2-{5-[3-chloro-4-(methyloxy)phenyl]-3-pyridin-4-yl-1H-1,2,4-triazol-1-yl}ethyl)-N-cyclopentyl-N'-(2,4,5-trichlorophenyl)urea |
| 127 | N-(2-{5-[3-chloro-4-(methyloxy)phenyl]-3-pyridin-4-yl-1H-1,2,4-triazol-1-yl}ethyl)-N-cyclopentyl-N'-(2,3-dimethylphenyl)urea |
| 128 | N-(2-{5-[3-chloro-4-(methyloxy)phenyl]-3-pyridin-4-yl-1H-1,2,4-triazol-1-yl}ethyl)-N-cyclopentyl-N'-(2,4-dimethylphenyl)urea |
| 129 | N-(2-{5-[3-chloro-4-(methyloxy)phenyl]-3-pyridin-4-yl-1H-1,2,4-triazol-1-yl}ethyl)-N'-(3-chloro-4-methylphenyl)-N-cyclopentylurea |
| 130 | N-(2-{5-[3-chloro-4-(methyloxy)phenyl]-3-pyridin-4-yl-1H-1,2,4-triazol-1-yl}ethyl)-N-cyclopentyl-N'-[2-(1,1-dimethylethyl)-6-methylphenyl]urea |
| 131 | N'-[4-(butyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 132 | N-(2-{5-[3-chloro-4-(methyloxy)phenyl]-3-pyridin-4-yl-1H-1,2,4-triazol-1-yl}ethyl)-N-cyclopentyl-N'-(2-methyl-3-nitrophenyl)urea |
| 133 | N-(2-{5-[3-chloro-4-(methyloxy)phenyl]-3-pyridin-4-yl-1H-1,2,4-triazol-1-yl}ethyl)-N-cyclopentyl-N'-(2,5-dichlorophenyl)urea |
| 134 | N-(2-{5-[3-chloro-4-(methyloxy)phenyl]-3-pyridin-4-yl-1H-1,2,4-triazol-1-yl}ethyl)-N-cyclopentyl-N'-(3-fluorophenyl)urea |

TABLE 3-continued

| Entry | Name |
|---|---|
| 135 | N-(2-{5-[3-chloro-4-(methyloxy)phenyl]-3-pyridin-4-yl-1H-1,2,4-triazol-1-yl}ethyl)-N'-(4-chlorophenyl)-N-cyclopentylurea |
| 136 | N-(2-{5-[3-chloro-4-(methyloxy)phenyl]-3-pyridin-4-yl-1H-1,2,4-triazol-1-yl}ethyl)-N-cyclopentyl-N'-(4-methylphenyl)urea |
| 137 | N-(2-{5-[3-chloro-4-(methyloxy)phenyl]-3-pyridin-4-yl-1H-1,2,4-triazol-1-yl}ethyl)-N-cyclopentyl-N'-(2,4,6-trichlorophenyl)urea |
| 138 | N-(2-{5-[3-chloro-4-(methyloxy)phenyl]-3-pyridin-4-yl-1H-1,2,4-triazol-1-yl}ethyl)-N-cyclopentyl-N'-[2-methyl-4-(methyloxy)phenyl]urea |
| 139 | N-(2-{5-[3-chloro-4-(methyloxy)phenyl]-3-pyridin-4-yl-1H-1,2,4-triazol-1-yl}ethyl)-N-cyclopentyl-N'-(2,5-dimethylphenyl)urea |
| 140 | N'-[5-chloro-2,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 141 | N-(2-{5-[3-chloro-4-(methyloxy)phenyl]-3-pyridin-4-yl-1H-1,2,4-triazol-1-yl}ethyl)-N-cyclopentyl-N'-(3,5-dichlorophenyl)urea |
| 142 | N'-[5-chloro-2-(methyloxy)phenyl]-N-(2-{5-[3-chloro-4-(methyloxy)phenyl]-3-pyridin-4-yl-1H-1,2,4-triazol-1-yl}ethyl)-N-cyclopentylurea |
| 143 | N-(2-{5-[3-chloro-4-(methyloxy)phenyl]-3-pyridin-4-yl-1H-1,2,4-triazol-1-yl}ethyl)-N-cyclopentyl-N'-[3-(methylthio)phenyl]urea |
| 144 | N-(2-{5-[3-chloro-4-(methyloxy)phenyl]-3-pyridin-4-yl-1H-1,2,4-triazol-1-yl}ethyl)-N-cyclopentyl-N'-(3,5-dimethylphenyl)urea |
| 145 | N-(2-{5-[3-chloro-4-(methyloxy)phenyl]-3-pyridin-4-yl-1H-1,2,4-triazol-1-yl}ethyl)-N-cyclopentyl-N'-[5-methyl-2-(methyloxy)phenyl]urea |
| 146 | N-(2-{5-[3-chloro-4-(methyloxy)phenyl]-3-pyridin-4-yl-1H-1,2,4-triazol-1-yl}ethyl)-N-cyclopentyl-N'-(4-iodophenyl)urea |
| 147 | N-(2-{5-[3-chloro-4-(methyloxy)phenyl]-3-pyridin-4-yl-1H-1,2,4-triazol-1-yl}ethyl)-N-cyclopentyl-N'-[4-(phenyloxy)phenyl]urea |
| 148 | N-(2-{5-[3-chloro-4-(methyloxy)phenyl]-3-pyridin-4-yl-1H-1,2,4-triazol-1-yl}ethyl)-N-cyclopentyl-N'-(2,4,6-trimethylphenyl)urea |
| 149 | N-(2-{5-[3-chloro-4-(methyloxy)phenyl]-3-pyridin-4-yl-1H-1,2,4-triazol-1-yl}ethyl)-N'-(5-chloro-2-methylphenyl)-N-cyclopentylurea |
| 150 | N-(2-{5-[3-chloro-4-(methyloxy)phenyl]-3-pyridin-4-yl-1H-1,2,4-triazol-1-yl}ethyl)-N'-(4-chloro-2-methylphenyl)-N-cyclopentylurea |
| 151 | N-(2-{5-[3-chloro-4-(methyloxy)phenyl]-3-pyridin-4-yl-1H-1,2,4-triazol-1-yl}ethyl)-N'-(2-chloro-6-methylphenyl)-N-cyclopentylurea |
| 152 | N-(2-{5-[3-chloro-4-(methyloxy)phenyl]-3-pyridin-4-yl-1H-1,2,4-triazol-1-yl}ethyl)-N'-(3-chloro-2-methylphenyl)-N-cyclopentylurea |
| 153 | N'-(3-chloro-4-fluorophenyl)-N-(2-{5-[3-chloro-4-(methyloxy)phenyl]-3-pyridin-4-yl-1H-1,2,4-triazol-1-yl}ethyl)-N-cyclopentylurea |
| 154 | N-(2-{5-[3-chloro-4-(methyloxy)phenyl]-3-pyridin-4-yl-1H-1,2,4-triazol-1-yl}ethyl)-N-cyclopentyl-N'-[2-(methylthio)phenyl]urea |
| 155 | N-(2-{5-[3-chloro-4-(methyloxy)phenyl]-3-pyridin-4-yl-1H-1,2,4-triazol-1-yl}ethyl)-N-cyclopentyl-N'-[3-(trifluoromethyl)phenyl]urea |
| 156 | N-(2-{5-[3-chloro-4-(methyloxy)phenyl]-3-pyridin-4-yl-1H-1,2,4-triazol-1-yl}ethyl)-N-cyclopentyl-N'-prop-2-en-1-ylurea |
| 157 | N-(2-{5-[3-chloro-4-(methyloxy)phenyl]-3-pyridin-4-yl-1H-1,2,4-triazol-1-yl}ethyl)-N-cyclopentyl-N'-[2-(1-methylethyl)phenyl]urea |
| 158 | N-(2-{5-[3-chloro-4-(methyloxy)phenyl]-3-pyridin-4-yl-1H-1,2,4-triazol-1-yl}ethyl)-N-cyclopentyl-N'-(5-fluoro-2-methylphenyl)urea |
| 159 | N-(2-{5-[3-chloro-4-(methyloxy)phenyl]-3-pyridin-4-yl-1H-1,2,4-triazol-1-yl}ethyl)-N-cyclopentyl-N'-(3,4-difluorophenyl)urea |
| 160 | N-[2-(5-methyl-3-pyridin-4-yl-1H-1,2,4-triazol-1-yl)ethyl]-N-(2-morpholin-4-ylethyl)-2-naphthalen-1-ylacetamide |
| 161 | N-cyclopentyl-N-(2-{5-methyl-3-[2-(methylamino)pyrimidin-4-yl]-1H-1,2,4-triazol-1-yl}ethyl)-2-naphthalen-1-ylacetamide |
| 162 | N-{2-[3-(2,1,3-benzothiadiazol-5-yl)-5-methyl-1H-1,2,4-triazol-1-yl]ethyl}-N-cyclopentyl-2-naphthalen-1-ylacetamide |
| 163 | N-cyclopentyl-N-{2-[5-methyl-3-(2-morpholin-4-ylpyridin-4-yl)-1H-1,2,4-triazol-1-yl]ethyl}-2-naphthalen-1-ylacetamide |
| 164 | N-cyclopentyl-N-{2-[3-(2-{[2-(dimethylamino)ethyl]amino}pyridin-4-yl)-5-methyl-1H-1,2,4-triazol-1-yl]ethyl}-2-naphthalen-1-ylacetamide |
| 165 | N-cyclopentyl-N-(2-{5-methyl-3-[2-(phenylamino)pyridin-4-yl]-1H-1,2,4-triazol-1-yl}ethyl)-2-naphthalen-1-ylacetamide |
| 166 | N-cyclopentyl-N-(2-{3-[2-(ethylamino)pyridin-4-yl]-5-methyl-1H-1,2,4-triazol-1-yl}ethyl)-2-naphthalen-1-ylacetamide |
| 167 | N-cyclopentyl-N-(2-{5-methyl-3-[2-(methylamino)pyridin-4-yl]-1H-1,2,4-triazol-1-yl}ethyl)-2-naphthalen-1-ylacetamide |
| 168 | N-cyclopropyl-N-[2-(5-methyl-3-pyridin-4-yl-1H-1,2,4-triazol-1-yl)ethyl]-2-naphthalen-1-ylacetamide |
| 169 | N-[2-(5-methyl-3-pyridin-4-yl-1H-1,2,4-triazol-1-yl)ethyl]-2-naphthalen-1-yl-N-(2-pyrrolidin-1-ylethyl)acetamide |
| 170 | N-[2-(dimethylamino)ethyl]-N-[2-(5-methyl-3-pyridin-4-yl-1H-1,2,4-triazol-1-yl)ethyl]-2-naphthalen-1-ylacetamide |
| 171 | N-[2-(5-methyl-3-pyridin-4-yl-1H-1,2,4-triazol-1-yl)ethyl]-2-naphthalen-1-yl-N-(tetrahydro-2H-pyran-4-yl)acetamide |
| 172 | N-cyclopentyl-N-[2-(5-methyl-3-{2-[(phenylmethyl)amino]pyridin-4-yl}-1H-1,2,4-triazol-1-yl)ethyl]-2-naphthalen-1-ylacetamide |

TABLE 3-continued

| Entry | Name |
|---|---|
| 173 | N-(2-{3-[2-(butylamino)pyridin-4-yl]-5-methyl-1H-1,2,4-triazol-1-yl}ethyl)-N-cyclopentyl-2-naphthalen-1-ylacetamide |
| 174 | N-cyclopentyl-N-[2-(5-methyl-3-{2-[(2-morpholin-4-ylethyl)amino]pyridin-4-yl}-1H-1,2,4-triazol-1-yl)ethyl]-2-naphthalen-1-ylacetamide |
| 175 | N-cyclopentyl-N-{2-[5-methyl-3-(2-{[2-(methyloxy)ethyl]amino}pyridin-4-yl)-1H-1,2,4-triazol-1-yl]ethyl}-2-naphthalen-1-ylacetamide |
| 176 | N-{2-[3-(2-aminopyridin-4-yl)-5-methyl-1H-1,2,4-triazol-1-yl]ethyl}-N-cyclopentyl-2-naphthalen-1-ylacetamide |
| 177 | N-(1-methylethyl)-N-[2-(5-methyl-3-pyridin-4-yl-1H-1,2,4-triazol-1-yl)ethyl]-2-naphthalen-1-ylacetamide |
| 178 | N-[2-(5-methyl-3-pyridin-4-yl-1H-1,2,4-triazol-1-yl)ethyl]-2-naphthalen-1-yl-N-(2-piperidin-1-ylethyl)acetamide |
| 179 | N-cyclohexyl-N-[2-(5-methyl-3-pyridin-4-yl-1H-1,2,4-triazol-1-yl)ethyl]-2-naphthalen-1-ylacetamide |
| 180 | N-[2-(5-methyl-3-pyridin-4-yl-1H-1,2,4-triazol-1-yl)ethyl]-2-naphthalen-1-yl-N-(tetrahydrofuran-2-ylmethyl)acetamide |
| 181 | N-cyclopentyl-N-(2-{5-methyl-3-[2-(piperidin-3-ylamino)pyridin-4-yl]-1H-1,2,4-triazol-1-yl}ethyl)-2-naphthalen-1-ylacetamide |
| 182 | N-cyclopentyl-N-[2-(5-methyl-3-{2-[(3R)-pyrrolidin-3-ylamino]pyridin-4-yl}-1H-1,2,4-triazol-1-yl)ethyl]-2-naphthalen-1-ylacetamide |
| 183 | N-cyclopentyl-N-[2-(5-methyl-3-{2-[(2-piperidin-1-ylethyl)amino]pyrimidin-4-yl}-1H-1,2,4-triazol-1-yl)ethyl]-2-naphthalen-1-ylacetamide |
| 184 | N-cyclopentyl-N-[2-(5-methyl-3-{2-[(phenylmethyl)amino]pyrimidin-4-yl}-1H-1,2,4-triazol-1-yl)ethyl]-2-naphthalen-1-ylacetamide |
| 185 | N-{2-[3-(2-amino-6-chloropyridin-4-yl)-5-methyl-1H-1,2,4-triazol-1-yl]ethyl}-N-cyclopentyl-2-naphthalen-1-ylacetamide |
| 186 | N-cyclopentyl-N-{2-[3-(2,6-diaminopyridin-4-yl)-5-methyl-1H-1,2,4-triazol-1-yl]ethyl}-2-naphthalen-1-ylacetamide |
| 187 | N-(2-{3-[2-amino-6-(ethyloxy)pyridin-4-yl]-5-methyl-1H-1,2,4-triazol-1-yl}ethyl)-N-cyclopentyl-2-naphthalen-1-ylacetamide |
| 188 | N-(2-{5-[3-chloro-4-(methyloxy)phenyl]-3-pyridin-4-yl-1H-1,2,4-triazol-1-yl}ethyl)-N-cyclopentyl-1-phenylcyclopropanecarboxamide |
| 189 | N-(2-{5-[3-chloro-4-(methyloxy)phenyl]-3-pyridin-4-yl-1H-1,2,4-triazol-1-yl}ethyl)-1-(4-chlorophenyl)-N-cyclopentylcyclopropanecarboxamide |
| 190 | N-(2-{5-[3-chloro-4-(methyloxy)phenyl]-3-pyridin-4-yl-1H-1,2,4-triazol-1-yl}ethyl)-N-cyclopentyl-2-methylcyclopropanecarboxamide |
| 191 | N-(2-{5-[3-chloro-4-(methyloxy)phenyl]-3-pyridin-4-yl-1H-1,2,4-triazol-1-yl}ethyl)-N-cyclopentyl-1-phenylcyclopentanecarboxamide |
| 192 | 4-chloro-N-(2-{5-[3-chloro-4-(methyloxy)phenyl]-3-pyridin-4-yl-1H-1,2,4-triazol-1-yl}ethyl)-N-cyclopentyl-2-(methyloxy)benzamide |
| 193 | N-(2-{5-[3-chloro-4-(methyloxy)phenyl]-3-pyridin-4-yl-1H-1,2,4-triazol-1-yl}ethyl)-N-cyclopentyl-3-phenylbutanamide |
| 194 | N-(2-{5-[3-chloro-4-(methyloxy)phenyl]-3-pyridin-4-yl-1H-1,2,4-triazol-1-yl}ethyl)-N-cyclopentyl-3,7-dimethyloct-6-enamide |
| 195 | N-(2-{5-[3-chloro-4-(methyloxy)phenyl]-3-pyridin-4-yl-1H-1,2,4-triazol-1-yl}ethyl)-N-cyclopentyl-3-(phenyloxy)propanamide |
| 196 | (3E)-N-(2-{5-[3-chloro-4-(methyloxy)phenyl]-3-pyridin-4-yl-1H-1,2,4-triazol-1-yl}ethyl)-N-cyclopentylhex-3-enamide |
| 197 | N-(2-{5-[3-chloro-4-(methyloxy)phenyl]-3-pyridin-4-yl-1H-1,2,4-triazol-1-yl}ethyl)-N-cyclopentyl-4-oxopentanamide |
| 198 | N-(2-{5-[3-chloro-4-(methyloxy)phenyl]-3-pyridin-4-yl-1H-1,2,4-triazol-1-yl}ethyl)-N-cyclopentyl-4-(3-methyl-5-oxo-4,5-dihydro-1H-pyrazol-1-yl)benzamide |
| 199 | N~2~-acetyl-N-(2-{5-[3-chloro-4-(methyloxy)phenyl]-3-pyridin-4-yl-1H-1,2,4-triazol-1-yl}ethyl)-N-cyclopentylglycinamide |
| 200 | N-(2-{5-[3-chloro-4-(methyloxy)phenyl]-3-pyridin-4-yl-1H-1,2,4-triazol-1-yl}ethyl)-N-cyclopentyl-2-(ethyloxy)acetamide |
| 201 | N-(2-{5-[3-chloro-4-(methyloxy)phenyl]-3-pyridin-4-yl-1H-1,2,4-triazol-1-yl}ethyl)-N-cyclopentyl-2-[3-(trifluoromethyl)phenyl]acetamide |
| 202 | N-(2-{5-[3-chloro-4-(methyloxy)phenyl]-3-pyridin-4-yl-1H-1,2,4-triazol-1-yl}ethyl)-N-cyclopentyl-5-oxo-L-prolinamide |
| 203 | N-(2-{5-[3-chloro-4-(methyloxy)phenyl]-3-pyridin-4-yl-1H-1,2,4-triazol-1-yl}ethyl)-N-cyclopentyl-3-furan-2-ylpropanamide |
| 204 | N-(2-{5-[3-chloro-4-(methyloxy)phenyl]-3-pyridin-4-yl-1H-1,2,4-triazol-1-yl}ethyl)-N-cyclopentyl-3-methylthiophene-2-carboxamide |
| 205 | N-(2-{5-[3-chloro-4-(methyloxy)phenyl]-3-pyridin-4-yl-1H-1,2,4-triazol-1-yl}ethyl)-N-cyclopentyl-1H-indole-3-carboxamide |
| 206 | N-(2-{5-[3-chloro-4-(methyloxy)phenyl]-3-pyridin-4-yl-1H-1,2,4-triazol-1-yl}ethyl)-N-cyclopentylpyrazine-2-carboxamide |
| 207 | N-(2-{5-[3-chloro-4-(methyloxy)phenyl]-3-pyridin-4-yl-1H-1,2,4-triazol-1-yl}ethyl)-N-cyclopentylpyridine-2-carboxamide |
| 208 | N-(2-{5-[3-chloro-4-(methyloxy)phenyl]-3-pyridin-4-yl-1H-1,2,4-triazol-1-yl}ethyl)-N-cyclopentyl-3-(phenylsulfonyl)propanamide |
| 209 | N-(2-{5-[3-chloro-4-(methyloxy)phenyl]-3-pyridin-4-yl-1H-1,2,4-triazol-1-yl}ethyl)-N-cyclopentyl-1H-benzimidazole-5-carboxamide |
| 210 | N-(2-{5-[3-chloro-4-(methyloxy)phenyl]-3-pyridin-4-yl-1H-1,2,4-triazol-1-yl}ethyl)-N-cyclopentyl-4-(methyloxy)quinoline-2-carboxamide |

TABLE 3-continued

| Entry | Name |
|---|---|
| 211 | N-(2-{5-[3-chloro-4-(methyloxy)phenyl]-3-pyridin-4-yl-1H-1,2,4-triazol-1-yl}ethyl)-N-cyclopentyl-2-methylpyridine-3-carboxamide |
| 212 | N-(2-{5-[3-chloro-4-(methyloxy)phenyl]-3-pyridin-4-yl-1H-1,2,4-triazol-1-yl}ethyl)-N-cyclopentyl-2-{[2-(methyloxy)phenyl]oxy}acetamide |
| 213 | N-(2-{5-[3-chloro-4-(methyloxy)phenyl]-3-pyridin-4-yl-1H-1,2,4-triazol-1-yl}ethyl)-N-cyclopentyl-2-[(2-methylphenyl)oxy]acetamide |
| 214 | N-(2-{5-[3-chloro-4-(methyloxy)phenyl]-3-pyridin-4-yl-1H-1,2,4-triazol-1-yl}ethyl)-N-cyclopentyl-2-[(2,5-dimethylphenyl)oxy]acetamide |
| 215 | N-(2-{5-[3-chloro-4-(methyloxy)phenyl]-3-pyridin-4-yl-1H-1,2,4-triazol-1-yl}ethyl)-N-cyclopentyl-2-[(4-ethylphenyl)oxy]acetamide |
| 216 | N-(2-{5-[3-chloro-4-(methyloxy)phenyl]-3-pyridin-4-yl-1H-1,2,4-triazol-1-yl}ethyl)-N-cyclopentyl-2-({4-[(phenylmethyl)oxy]phenyl}oxy)acetamide |
| 217 | N-(2-{5-[3-chloro-4-(methyloxy)phenyl]-3-pyridin-4-yl-1H-1,2,4-triazol-1-yl}ethyl)-N-cyclopentyl-2-{[3-(methyloxy)phenyl]oxy}acetamide |
| 218 | N-(2-{5-[3-chloro-4-(methyloxy)phenyl]-3-pyridin-4-yl-1H-1,2,4-triazol-1-yl}ethyl)-N-cyclopentyl-2-(2,4,6-trimethylphenyl)acetamide |
| 219 | N-(2-{5-[3-chloro-4-(methyloxy)phenyl]-3-pyridin-4-yl-1H-1,2,4-triazol-1-yl}ethyl)-N-cyclopentyl-2-[(3,4-dimethylphenyl)oxy]acetamide |
| 220 | Nalpha-acetyl-N-(2-{5-[3-chloro-4-(methyloxy)phenyl]-3-pyridin-4-yl-1H-1,2,4-triazol-1-yl}ethyl)-N-cyclopentyl-3-fluorophenylalaninamide |
| 221 | Nalpha-acelyl-N-(2-{5-[3-chloro-4-(methyloxy)phenyl]-3-pyridin-4-yl-1H-1,2,4-triazol-1-yl}ethyl)-N-cyclopentyl-4-fluorophenylalaninamide |
| 222 | N-{2-[(2-{5-[3-chloro-4-(methyloxy)phenyl]-3-pyridin-4-yl-1H-1,2,4-triazol-1-yl}ethyl)(cyclopentyl)amino]-1-methyl-2-oxoethyl}benzamide |
| 223 | N-(2-{5-[3-chloro-4-(methyloxy)phenyl]-3-pyridin-4-yl-1H-1,2,4-triazol-1-yl}ethyl)-N-cyclopentyl-4-(4-methylphenyl)-4-oxobutanamide |
| 224 | 4-(acetylamino)-N-(2-{5-[3-chloro-4-(methyloxy)phenyl]-3-pyridin-4-yl-1H-1,2,4-triazol-1-yl}ethyl)-N-cyclopentylbutanamide |
| 225 | N-(2-{5-[3-chloro-4-(methyloxy)phenyl]-3-pyridin-4-yl-1H-1,2,4-triazol-1-yl}ethyl)-N-cyclopentyl-2,2-dimethylpentanamide |
| 226 | N-(2-{5-[3-chloro-4-(methyloxy)phenyl]-3-pyridin-4-yl-1H-1,2,4-triazol-1-yl}ethyl)-N-cyclopentyl-N'-phenylpentanediamide |
| 227 | N-(2-{5-[3-chloro-4-(methyloxy)phenyl]-3-pyridin-4-yl-1H-1,2,4-triazol-1-yl}ethyl)-N-cyclopentyltetrahydrofuran-2-carboxamide |
| 228 | N-(2-{5-[3-chloro-4-(methyloxy)phenyl]-3-pyridin-4-yl-1H-1,2,4-triazol-1-yl}ethyl)-N-cyclopentyl-2-(1,3-dimethyl-2,6-dioxo-1,2,3,6-tetrahydro-7H-purin-7-yl)acetamide |
| 229 | N-{2-[(2-{5-[3-chloro-4-(methyloxy)phenyl]-3-pyridin-4-yl-1H-1,2,4-triazol-1-yl}ethyl)(cyclopentyl)amino]-2-oxoethyl}furan-2-carboxamide |
| 230 | N~2~-acetyl-N~1~-(2-{5-[3-chloro-4-(methyloxy)phenyl]-3-pyridin-4-yl-1H-1,2,4-triazol-1-yl}ethyl)-N~1~-cyclopentyl-L-glutamamide |
| 231 | (4E)-N-(2-{5-[3-chloro-4-(methyloxy)phenyl]-3-pyridin-4-yl-1H-1,2,4-triazol-1-yl}ethyl)-N-cyclopentylhex-4-enamide |
| 232 | N-(2-{5-[3-chloro-4-(methyloxy)phenyl]-3-pyridin-4-yl-1H-1,2,4-triazol-1-yl}ethyl)-N-cyclopentyl-2-cyclopropylacetamide |
| 233 | N-(2-{5-[3-chloro-4-(methyloxy)phenyl]-3-pyridin-4-yl-1H-1,2,4-triazol-1-yl}ethyl)-N-cyclopentyl-3-(methyloxy)propanamide |
| 234 | N-(2-{5-[3-chloro-4-(methyloxy)phenyl]-3-pyridin-4-yl-1H-1,2,4-triazol-1-yl}ethyl)-N-cyclopentyl-N',N'-dimethylbutanediamide |
| 235 | N-(2-{5-[3-chloro-4-(methyloxy)phenyl]-3-pyridin-4-yl-1H-1,2,4-triazol-1-yl}ethyl)-N-cyclopentyl-5-[(phenylmethyl)oxy]-1H-indole-2-carboxamide |
| 236 | N-(2-{5-[3-chloro-4-(methyloxy)phenyl]-3-pyridin-4-yl-1H-1,2,4-triazol-1-yl}ethyl)-N-cyclopentyl-2-(1H-pyrrol-1-yl)benzamide |
| 237 | 3-(2-chloro-6-fluorophenyl)-N-(2-{5-[3-chloro-4-(methyloxy)phenyl]-3-pyridin-4-yl-1H-1,2,4-triazol-1-yl}ethyl)-N-cyclopentyl-5-methylisoxazole-4-carboxamide |
| 238 | N-(2-{5-[3-chloro-4-(methyloxy)phenyl]-3-pyridin-4-yl-1H-1,2,4-triazol-1-yl}ethyl)-N-cyclopentyl-N'-[(1R)-1-phenylethyl]benzene-1,2-dicarboxamide |
| 239 | N-(2-{5-[3-chloro-4-(methyloxy)phenyl]-3-pyridin-4-yl-1H-1,2,4-triazol-1-yl}ethyl)-N-cyclopentyl-5-oxoprolinamide |
| 240 | N~2~-acetyl-N-(2-{5-[3-chloro-4-(methyloxy)phenyl]-3-pyridin-4-yl-1H-1,2,4-triazol-1-yl}ethyl)-N-cyclopentyl-L-leucinamide |
| 241 | N-(2-{5-[3-chloro-4-(methyloxy)phenyl]-3-pyridin-4-yl-1H-1,2,4-triazol-1-yl}ethyl)-N-cyclopentyl-1-(4-methylphenyl)cyclohexanecarboxamide |
| 242 | N~2~-acetyl-N~1~-(2-{5-[3-chloro-4-(methyloxy)phenyl]-3-pyridin-4-yl-1H-1,2,4-triazol-1-yl}ethyl)-N~1~-cyclopentyl-L-aspartamide |
| 243 | N-(2-{5-[3-chloro-4-(methyloxy)phenyl]-3-pyridin-4-yl-1H-1,2,4-triazol-1-yl}ethyl)-N-cyclopentyl-5-oxo-D-prolinamide |
| 244 | N-(2-{5-[3-chloro-4-(methyloxy)phenyl]-3-pyridin-4-yl-1H-1,2,4-triazol-1-yl}ethyl)-N-cyclopentyl-5-methylpyrazine-2-carboxamide |
| 245 | N-(2-{5-[3-chloro-4-(methyloxy)phenyl]-3-pyridin-4-yl-1H-1,2,4-triazol-1-yl}ethyl)-N-cyclopentyl-2-methylcyclohexanecarboxamide |
| 246 | N-(2-{5-[3-chloro-4-(methyloxy)phenyl]-3-pyridin-4-yl-1H-1,2,4-triazol-1-yl}ethyl)-N-cyclopentyl-3-(methyloxy)cyclohexanecaxboxamide |
| 247 | N-(2-{5-[3-chloro-4-(methyloxy)phenyl]-3-pyridin-4-yl-1H-1,2,4-triazol-1-yl}ethyl)-N-cyclopentyl-4-(methyloxy)cyclohexanecaxboxamide |
| 248 | N-(2-{5-[3-chloro-4-(methyloxy)phenyl]-3-pyridin-4-yl-1H-1,2,4-triazol-1-yl}ethyl)-N-cyclopentyl-2-(2-methyl-1H-indol-3-yl)acetamide |

TABLE 3-continued

| Entry | Name |
|---|---|
| 249 | N-(2-{5-[3-chloro-4-(methyloxy)phenyl]-3-pyridin-4-yl-1H-1,2,4-triazol-1-yl}ethyl)-N-cyclopentyltetrahydrofuran-3-carboxamide |
| 250 | N-(2-{5-[3-chloro-4-(methyloxy)phenyl]-3-pyridin-4-yl-1H-1,2,4-triazol-1-yl}ethyl)-N-cyclopentyl-2,6-bis(methyloxy)pyridine-3-carboxamide |
| 251 | N-(2-{5-[3-chloro-4-(methyloxy)phenyl]-3-pyridin-4-yl-1H-1,2,4-triazol-1-yl}ethyl)-N-cyclopentyl-3-(2-methylphenyl)propanamide |
| 252 | N~2~-[(butylamino)carbonyl]-N-(2-{5-[3-chloro-4-(methyloxy)phenyl]-3-pyridin-4-yl-1H-1,2,4-triazol-1-yl}ethyl)-N-cyclopentylglycinamide |
| 253 | N-{2-[(2-{5-[3-chloro-4-(methyloxy)phenyl]-3-pyridin-4-yl-1H-1,2,4-triazol-1-yl}ethyl)(cyclopentyl)amino]-2-oxoethyl}-N-methylbenzamide |
| 254 | N-(2-{5-[3-chloro-4-(methyloxy)phenyl]-3-pyridin-4-yl-1H-1,2,4-triazol-1-yl}ethyl)-4-(cyclohex-2-en-1-yloxy)-N-cyclopentylbenzamide |
| 255 | 2-[(1S,4R)-bicyclo[2.2.1]hept-2-yl]-N-(2-{5-[3-chloro-4-(methyloxy)phenyl]-3-pyridin-4-yl-1H-1,2,4-triazol-1-yl}ethyl)-N-cyclopentylacetamide |
| 256 | (1S,4R)-N-(2-{5-[3-chloro-4-(methyloxy)phenyl]-3-pyridin-4-yl-1H-1,2,4-triazol-1-yl}ethyl)-N-cyclopentylbicyclo[2.2.1]heptane-2-carboxamide |
| 257 | N-(2-{5-[3-chloro-4-(methyloxy)phenyl]-3-pyridin-4-yl-1H-1,2,4-triazol-1-yl}ethyl)-N-cyclopentyl-2-{3-(methyloxy)-4-[(phenylmethyl)oxy]phenyl}acetamide |
| 258 | N-(2-{5-[3-chloro-4-(methyloxy)phenyl]-3-pyridin-4-yl-1H-1,2,4-triazol-1-yl}ethyl)-N-cyclopentylcyclopropane-1,1-dicarboxamide |
| 259 | N-(2-{5-[3-chloro-4-(methyloxy)phenyl]-3-pyridin-4-yl-1H-1,2,4-triazol-1-yl}ethyl)-N-cyclopentyl-2-methyl-4-oxo-4-phenylbutanamide |
| 260 | N-(2-{5-[3-chloro-4-(methyloxy)phenyl]-3-pyridin-4-yl-1H-1,2,4-triazol-1-yl}ethyl)-N-cyclopentyl-2-[4-(methylsulfonyl)phenyl]acetamide |
| 261 | N-(2-{5-[3-chloro-4-(methyloxy)phenyl]-3-pyridin-4-yl-1H-1,2,4-triazol-1-yl}ethyl)-N-cyclopentyl-3,5-dimethyl-4-[(phenylmethyl)oxy]benzamide |
| 262 | (1R,2S)-N-(2-{5-[3-chloro-4-(methyloxy)phenyl]-3-pyridin-4-yl-1H-1,2,4-triazol-1-yl}ethyl)-N-cyclopentyl-2-(phenylcarbonyl)cyclohexanecarboxamide |
| 263 | (1R,2R)-N-(2-{5-[3-chloro-4-(methyloxy)phenyl]-3-pyridin-4-yl-1H-1,2,4-triazol-1-yl}ethyl)-N-cyclopentyl-2-(phenylcarbonyl)cyclohexanecarboxamide |
| 264 | (1R,2R)-N-(2-{5-[3-chloro-4-(methyloxy)phenyl]-3-pyridin-4-yl-1H-1,2,4-triazol-1-yl}ethyl)-N-cyclopentyl-2-[(4-methylphenyl)carbonyl]cyclohexanecarboxamide |
| 265 | 2-[2,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylacetamide |
| 266 | Nalpha-acetyl-N-(2-{5-[3-chloro-4-(methyloxy)phenyl]-3-pyridin-4-yl-1H-1,2,4-triazol-1-yl}ethyl)-N-cyclopentyl-O-methyl-3-(methyloxy)-D-tyrosinamide |
| 267 | N-(2-{5-[3-chloro-4-(methyloxy)phenyl]-3-pyridin-4-yl-1H-1,2,4-triazol-1-yl}ethyl)-N-cyclopentyl-2-[(phenylmethyl)oxy]propanamide |
| 268 | N-(2-{5-[3-chloro-4-(methyloxy)phenyl]-3-pyridin-4-yl-1H-1,2,4-triazol-1-yl}ethyl)-N-cyclopentyl-1-methylcyclopropanecarboxamide |
| 269 | N-(2-{5-[3-chloro-4-(methyloxy)phenyl]-3-pyridin-4-yl-1H-1,2,4-triazol-1-yl}ethyl)-N-cyclopentyl-4-(methylthio)benzamide |
| 270 | N-(2-{5-[3-chloro-4-(methyloxy)phenyl]-3-pyridin-4-yl-1H-1,2,4-triazol-1-yl}ethyl)-N-cyclopentylcycloheptanecarboxamide |
| 271 | N-(2-{5-[3-chloro-4-(methyloxy)phenyl]-3-pyridin-4-yl-1H-1,2,4-triazol-1-yl}ethyl)-N-cyclopentyl-5-oxohexanamide |
| 272 | N-(2-{5-[3-chloro-4-(methyloxy)phenyl]-3-pyridin-4-yl-1H-1,2,4-triazol-1-yl}ethyl)-N-cyclopentyl-3-(2-nitrophenyl)-2-oxopropanamide |
| 273 | N-(2-{5-[3-chloro-4-(methyloxy)phenyl]-3-pyridin-4-yl-1H-1,2,4-triazol-1-yl}ethyl)-N-cyclopentyl-2,3,5,6-tetrafluoro-4-methylbenzamide |
| 274 | 3-(aminosulfonyl)-4-chloro-N-(2-{5-[3-chloro-4-(methyloxy)phenyl]-3-pyridin-4-yl-1H-1,2,4-triazol-1-yl}ethyl)-N-cyclopentylbenzamide |
| 275 | N-(2-{5-[3-chloro-4-(methyloxy)phenyl]-3-pyridin-4-yl-1H-1,2,4-triazol-1-yl}ethyl)-N-cyclopentyl-2-methylpent-4-enamide |
| 276 | (3E)-N-(2-{5-[3-chloro-4-(methyloxy)phenyl]-3-pyridin-4-yl-1H-1,2,4-triazol-1-yl}ethyl)-N-cyclopentyloct-3-enamide |
| 277 | 2-bromo-N-(2-{5-[3-chloro-4-(methyloxy)phenyl]-3-pyridin-4-yl-1H-1,2,4-triazol-1-yl}ethyl)-N-cyclopentyl-4,5-bis(methyloxy)benzamide |
| 278 | N-(2-{5-[3-chloro-4-(methyloxy)phenyl]-3-pyridin-4-yl-1H-1,2,4-triazol-1-yl}ethyl)-N-cyclopentyl-2-methyl-4-(methyloxy)benzamide |
| 279 | N-(2-{5-[3-chloro-4-(methyloxy)phenyl]-3-pyridin-4-yl-1H-1,2,4-triazol-1-yl}ethyl)-N-cyclopentyl-2-(ethylthio)acetamide |
| 280 | N-(2-{5-[3-chloro-4-(methyloxy)phenyl]-3-pyridin-4-yl-1H-1,2,4-triazol-1-yl}ethyl)-N-cyclopentyl-2-(methylthio)benzamide |
| 281 | N-(2-{5-[3-chloro-4-(methyloxy)phenyl]-3-pyridin-4-yl-1H-1,2,4-triazol-1-yl}ethyl)-N-cyclopentyl-2-(2,3-difluorophenyl)acetamide |
| 282 | N-(2-{5-[3-chloro-4-(methyloxy)phenyl]-3-pyridin-4-yl-1H-1,2,4-triazol-1-yl}ethyl)-N-cyclopentyl-4'-methylbiphenyl-2-carboxamide |
| 283 | 3,5-dibromo-N-(2-{5-[3-chloro-4-(methyloxy)phenyl]-3-pyridin-4-yl-1H-1,2,4-triazol-1-yl}ethyl)-N-cyclopentylbenzamide |
| 284 | 3-chloro-N-(2-{5-[3-chloro-4-(methyloxy)phenyl]-3-pyridin-4-yl-1H-1,2,4-triazol-1-yl}ethyl)-N-cyclopentyl-2-methylbenzamide |
| 285 | N-(2-{5-[3-chloro-4-(methyloxy)phenyl]-3-pyridin-4-yl-1H-1,2,4-triazol-1-yl}ethyl)-N-cyclopentyl-3-(methylthio)propanamide |

TABLE 3-continued

| Entry | Name |
|---|---|
| 286 | N-(2-{5-[3-chloro-4-(methyloxy)phenyl]-3-pyridin-4-yl-1H-1,2,4-triazol-1-yl}ethyl)-N-cyclopentyl-3-methylcyclohexanecarboxamide |
| 287 | N-(2-{5-[3-chloro-4-(methyloxy)phenyl]-3-pyridin-4-yl-1H-1,2,4-triazol-1-yl}ethyl)-N-cyclopentyl-4-methylcyclohexanecarboxamide |
| 288 | N-(2-{5-[3-chloro-4-(methyloxy)phenyl]-3-pyridin-4-yl-1H-1,2,4-triazol-1-yl}ethyl)-5-cyclohexyl-N-cyclopentylpentanamide |
| 289 | N-(2-{5-[3-chloro-4-(methyloxy)phenyl]-3-pyridin-4-yl-1H-1,2,4-triazol-1-yl}ethyl)-N-cyclopentyl-2-(4-methylcyclohexyl)acetamide |
| 290 | N-(2-{5-[3-chloro-4-(methyloxy)phenyl]-3-pyridin-4-yl-1H-1,2,4-triazol-1-yl}ethyl)-N-cyclopentyl-2-(methylthio)acetamide |
| 291 | (1R,4R)-N-(2-{5-[3-chloro-4-(methyloxy)phenyl]-3-pyridin-4-yl-1H-1,2,4-triazol-1-yl}ethyl)-N-cyclopentylbicyclo[2.2.1]hept-5-ene-2-carboxamide |
| 292 | N-(2-{5-[3-chloro-4-(methyloxy)phenyl]-3-pyridin-4-yl-1H-1,2,4-triazol-1-yl}ethyl)-N-cyclopentyl-4,4,4-trifluoro-2-methylbutanamide |
| 293 | N-(2-{5-[3-chloro-4-(methyloxy)phenyl]-3-pyridin-4-yl-1H-1,2,4-triazol-1-yl}ethyl)-N-cyclopentyl-2-methyl-3-phenylpropanamide |
| 294 | N-(2-{5-[3-chloro-4-(methyloxy)phenyl]-3-pyridin-4-yl-1H-1,2,4-triazol-1-yl}ethyl)-N-cyclopentyl-2-[4-(methylthio)phenyl]acetamide |
| 295 | N-(2-{5-[3-chloro-4-(methyloxy)phenyl]-3-pyridin-4-yl-1H-1,2,4-triazol-1-yl}ethyl)-N-cyclopentyl-2-(methyloxy)-4-nitrobenzamide |
| 296 | N-(2-{5-[3-chloro-4-(methyloxy)phenyl]-3-pyridin-4-yl-1H-1,2,4-triazol-1-yl}ethyl)-5-[2-chloro-5-(trifluoromethyl)phenyl]-N-cyclopentylfuran-2-carboxamide |
| 297 | N-(2-{5-[3-chloro-4-(methyloxy)phenyl]-3-pyridin-4-yl-1H-1,2,4-triazol-1-yl}ethyl)-N-cyclopentyl-5-fluoro-2-(methyloxy)benzamide |
| 298 | 3-[3,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylpropanamide |
| 299 | N-(2-{5-[3-chloro-4-(methyloxy)phenyl]-3-pyridin-4-yl-1H-1,2,4-triazol-1-yl}ethyl)-N-cyclopentyl-4-(3,5-difluorophenyl)-4-oxobutanamide |
| 300 | N-(2-{5-[3-chloro-4-(methyloxy)phenyl]-3-pyridin-4-yl-1H-1,2,4-triazol-1-yl}ethyl)-1-methyl-1H-indole-3-carboxamide |
| 301 | N-(2-{5-[3-chloro-4-(methyloxy)phenyl]-3-pyridin-4-yl-1H-1,2,4-triazol-1-yl}ethyl)-N-cyclopentyl-4-(phenyloxy)benzamide |
| 302 | N-(2-{5-[3-chloro-4-(methyloxy)phenyl]-3-pyridin-4-yl-1H-1,2,4-triazol-1-yl}ethyl)-N-cyclopentyl-2-[(1E)-3,3-dimethyltriaz-1-en-1-yl]benzamide |
| 303 | N-(2-{5-[3-chloro-4-(methyloxy)phenyl]-3-pyridin-4-yl-1H-1,2,4-triazol-1-yl}ethyl)-N-cyclopentyl-2-[(3-methylphenyl)oxy]acetamide |
| 304 | N-(2-{5-[3-chloro-4-(methyloxy)phenyl]-3-pyridin-4-yl-1H-1,2,4-triazol-1-yl}ethyl)-N-cyclopentyl-2-{[4-(1-methylethyl)phenyl]oxy}acetamide |
| 305 | N-(2-{5-[3-chloro-4-(methyloxy)phenyl]-3-pyridin-4-yl-1H-1,2,4-triazol-1-yl}ethyl)-N'-(4-nitrophenyl)ethanediamide |
| 306 | N-(2-{5-[3-chloro-4-(methyloxy)phenyl]-3-pyridin-4-yl-1H-1,2,4-triazol-1-yl}ethyl)-N-cyclopentyl-3-(ethyloxy)benzamide |
| 307 | N-(2-{5-[3-chloro-4-(methyloxy)phenyl]-3-pyridin-4-yl-1H-1,2,4-triazol-1-yl}ethyl)-N-cyclopentyl-4-(methyloxy)-3-[(phenylmethyl)oxy]benzamide |
| 308 | N-(2-{5-[3-chloro-4-(methyloxy)phenyl]-3-pyridin-4-yl-1H-1,2,4-triazol-1-yl}ethyl)-N-cyclopentyl-4-[(phenylmethyl)oxy]benzamide |
| 309 | N-(2-{5-[3-chloro-4-(methyloxy)phenyl]-3-pyridin-4-yl-1H-1,2,4-triazol-1-yl}ethyl)-N-cyclopentyl-4-oxo-4-(2-thienyl)butanamide |
| 310 | N-(2-{5-[3-chloro-4-(methyloxy)phenyl]-3-pyridin-4-yl-1H-1,2,4-triazol-1-yl}ethyl)-N-cyclopentyl-3-nitro-5-(trifluoromethyl)benzamide |
| 311 | (4E)-4-[(aminocarbonyl)hydrazono]-N-(2-{5-[3-chloro-4-(methyloxy)phenyl]-3-pyridin-4-yl-1H-1,2,4-triazol-1-yl}ethyl)-N-cyclopentylpentanamide |
| 312 | N-(2-{5-[3-chloro-4-(methyloxy)phenyl]-3-pyridin-4-yl-1H-1,2,4-triazol-1-yl}ethyl)-4-cyclohexyl-N-cyclopentylbenzamide |
| 313 | 4-(1H-benzimidazol-1-ylmethyl)-N-(2-{5-[3-chloro-4-(methyloxy)phenyl]-3-pyridin-4-yl-1H-1,2,4-triazol-1-yl}ethyl)-N-cyclopentylbenzamide |
| 314 | 2-(acetylamino)-5-bromo-N-(2-{5-[3-chloro-4-(methyloxy)phenyl]-3-pyridin-4-yl-1H-1,2,4-triazol-1-yl}ethyl)-N-cyclopentylbenzamide |
| 315 | 4-bromo-N-(2-{5-[3-chloro-4-(methyloxy)phenyl]-3-pyridin-4-yl-1H-1,2,4-triazol-1-yl}ethyl)-N-cyclopentyl-2-methylbenzamide |
| 316 | N-(2-{5-[3-chloro-4-(methyloxy)phenyl]-3-pyridin-4-yl-1H-1,2,4-triazol-1-yl}ethyl)-N-cyclopentyl-2-(1,3-dioxo-1,3-dihydro-2H-isoindol-2-yl)benzamide |
| 317 | phenylmethyl 4-{[(2-{5-[3-chloro-4-(methyloxy)phenyl]-3-pyridin-4-yl-1H-1,2,4-triazol-1-yl}ethyl)(cyclopentyl)amino]carbonyl}piperidine-1-carboxylate |
| 318 | 4,5-dibromo-N-(2-{5-[3-chloro-4-(methyloxy)phenyl]-3-pyridin-4-yl-1H-1,2,4-triazol-1-yl}ethyl)-N-cyclopentylfuran-2-carboxamide |
| 319 | N-(2-{5-[3-chloro-4-(methyloxy)phenyl]-3-pyridin-4-yl-1H-1,2,4-triazol-1-yl}ethyl)-N-cyclopentyl-2-oxo-2-(2,4,6-trimethylphenyl)acetamide |
| 320 | N-(2-{5-[3-chloro-4-(methyloxy)phenyl]-3-pyridin-4-yl-1H-1,2,4-triazol-1-yl}ethyl)-N-cyclopentyl-4-(ethylthio)benzamide |
| 321 | N-(2-{5-[3-chloro-4-(methyloxy)phenyl]-3-pyridin-4-yl-1H-1,2,4-triazol-1-yl}ethyl)-N-cyclopentyl-2-(phenylthio)acetamide |
| 322 | 3,5-dibromo-N-(2-{5-[3-chloro-4-(methyloxy)phenyl]-3-pyridin-4-yl-1H-1,2,4-triazol-1-yl}ethyl)-N-cyclopentyl-4-methylbenzamide |
| 323 | N-(2-{5-[3-chloro-4-(methyloxy)phenyl]-3-pyridin-4-yl-1H-1,2,4-triazol-1-yl}ethyl)-2-cyano-N-cyclopentylacetamide |

TABLE 3-continued

| Entry | Name |
|---|---|
| 324 | N-(2-{5-[3-chloro-4-(methyloxy)phenyl]-3-pyridin-4-yl-1H-1,2,4-triazol-1-yl}ethyl)-N-cyclopentyl-4-(1,3-dioxo-1,3-dihydro-2H-isoindol-2-yl)benzamide |
| 325 | N-(2-{5-[3-chloro-4-(methyloxy)phenyl]-3-pyridin-4-yl-1H-1,2,4-triazol-1-yl}ethyl)-1-cyano-N-cyclopentylcyclopropanecarboxamide |
| 326 | N-(2-{5-[3-chloro-4-(methyloxy)phenyl]-3-pyridin-4-yl-1H-1,2,4-triazol-1-yl}ethyl)-N-cyclopentylhex-5-ynamide |
| 327 | N-(2-{5-[3-chloro-4-(methyloxy)phenyl]-3-pyridin-4-yl-1H-1,2,4-triazol-1-yl}ethyl)-N-cyclopentyl-2-(2,3-dihydro-1H-inden-2-yl)acetamide |
| 328 | N-(2-{5-[3-chloro-4-(methyloxy)phenyl]-3-pyridin-4-yl-1H-1,2,4-triazol-1-yl}ethyl)-N-cyclopentyl-4-[4-(methylsulfonyl)phenyl]-4-oxobutanamide |
| 329 | N-(2-{5-[3-chloro-4-(methyloxy)phenyl]-3-pyridin-4-yl-1H-1,2,4-triazol-1-yl}ethyl)-N-cyclopentyl-2-(3,5-dimethylphenyl)acetamide |
| 330 | N-(2-{5-[3-chloro-4-(methyloxy)phenyl]-3-pyridin-4-yl-1H-1,2,4-triazol-1-yl}ethyl)-N-cyclopentyl-N',N'-bis[(1S)-1-phenylethyl]benzene-1,2-dicarboxamide |
| 331 | N-(2-{5-[3-chloro-4-(methyloxy)phenyl]-3-pyridin-4-yl-1H-1,2,4-triazol-1-yl}ethyl)-N-cyclopentyl-6-(methyloxy)naphthalene-2-carboxamide |
| 332 | N-(2-{5-[3-chloro-4-(methyloxy)phenyl]-3-pyridin-4-yl-1H-1,2,4-triazol-1-yl}ethyl)-2-cycloheptyl-N-cyclopentylacetamide |
| 333 | 2-chloro-N-(2-{5-[3-chloro-4-(methyloxy)phenyl]-3-pyridin-4-yl-1H-1,2,4-triazol-1-yl}ethyl)-N-cyclopentyl-6-fluorobenzamide |
| 334 | N-(2-{5-[3-chloro-4-(methyloxy)phenyl]-3-pyridin-4-yl-1H-1,2,4-triazol-1-yl}ethyl)-N-cyclopentyl-3,5-dimethylbenzamide |
| 335 | 4-(4-bromophenyl)-N-(2-{5-[3-chloro-4-(methyloxy)phenyl]-3-pyridin-4-yl-1H-1,2,4-triazol-1-yl}ethyl)-N-cyclopentyl-4-oxobutanamide |
| 336 | N-(2-{5-[3-chloro-4-(methyloxy)phenyl]-3-pyridin-4-yl-1H-1,2,4-triazol-1-yl}ethyl)-N-cyclopentyl-2-[(4-methylphenyl)carbonyl]benzamide |
| 337 | N-(2-{5-[3-chloro-4-(methyloxy)phenyl]-3-pyridin-4-yl-1H-1,2,4-triazol-1-yl}ethyl)-2-[(2-cyanophenyl)thio]-N-cyclopentylbenzamide |
| 338 | N-(2-{5-[3-chloro-4-(methyloxy)phenyl]-3-pyridin-4-yl-1H-1,2,4-triazol-1-yl}ethyl)-N-cyclopentyl-2-[(1R,2S,3R)-3-methyl-2-(nitromethyl)-5-oxocyclopentyl]acetamide |
| 339 | N-(2-{5-[3-chloro-4-(methyloxy)phenyl]-3-pyridin-4-yl-1H-1,2,4-triazol-1-yl}ethyl)-N-cyclopentyl-2-(phenyloxy)butanamide |
| 340 | N-(2-{5-[3-chloro-4-(methyloxy)phenyl]-3-pyridin-4-yl-1H-1,2,4-triazol-1-yl}ethyl)-N-cyclopentyl-2-[(2-{[2-(methyloxy)ethyl]oxy}ethyl)oxy]acetamide |
| 341 | N-(2-{5-[3-chloro-4-(methyloxy)phenyl]-3-pyridin-4-yl-1H-1,2,4-triazol-1-yl}ethyl)-N-cyclopentyl-1,5-dimethyl-1H-pyrazole-3-carboxamide |
| 342 | 2-chloro-N-(2-{5-[3-chloro-4-(methyloxy)phenyl]-3-pyridin-4-yl-1H-1,2,4-triazol-1-yl}ethyl)-N-cyclopentyl-5-(methylthio)benzamide |
| 343 | N-(2-{5-[3-chloro-4-(methyloxy)phenyl]-3-pyridin-4-yl-1H-1,2,4-triazol-1-yl}ethyl)-2,2-dicyclohexyl-N-cyclopentylacetamide |
| 344 | N-(2-{5-[3-chloro-4-(methyloxy)phenyl]-3-pyridin-4-yl-1H-1,2,4-triazol-1-yl}ethyl)-N-cyclopentyl-2-oxo-3-phenylpropanamide |
| 345 | N-(2-{5-[3-chloro-4-(methyloxy)phenyl]-3-pyridin-4-yl-1H-1,2,4-triazol-1-yl}ethyl)-N-cyclopentylprop-2-ynamide |
| 346 | N-alpha-acetyl-N-(2-{5-[3-chloro-4-(methyloxy)phenyl]-3-pyridin-4-yl-1H-1,2,4-triazol-1-yl}ethyl)-N-cyclopentyltryptophanamide |
| 347 | N-(2-{5-[3-chloro-4-(methyloxy)phenyl]-3-pyridin-4-yl-1H-1,2,4-triazol-1-yl}ethyl)-N-cyclopentyl-2-(1,3-dioxo-1,3-dihydro-2H-isoindol-2-yl)acetamide |
| 348 | N-(2-{5-[3-chloro-4-(methyloxy)phenyl]-3-pyridin-4-yl-1H-1,2,4-triazol-1-yl}ethyl)-2-cyclopent-2-en-1-yl-N-cyclopentylacetamide |
| 349 | 2,5-dichloro-N-(2-{5-[3-chloro-4-(methyloxy)phenyl]-3-pyridin-4-yl-1H-1,2,4-triazol-1-yl}ethyl)-N-cyclopentylbenzamide |
| 350 | N-(2-{5-[3-chloro-4-(methyloxy)phenyl]-3-pyridin-4-yl-1H-1,2,4-triazol-1-yl}ethyl)-N-cyclopentyl-2,5-dimethylbenzamide |
| 351 | N-(2-{5-[3-chloro-4-(methyloxy)phenyl]-3-pyridin-4-yl-1H-1,2,4-triazol-1-yl}ethyl)-N-cyclopentyl-2,6-dimethylbenzamide |
| 352 | 3-bromo-N-(2-{5-[3-chloro-4-(methyloxy)phenyl]-3-pyridin-4-yl-1H-1,2,4-triazol-1-yl}ethyl)-N-cyclopentyl-4-methylbenzamide |
| 353 | N-(2-{5-[3-chloro-4-(methyloxy)phenyl]-3-pyridin-4-yl-1H-1,2,4-triazol-1-yl}ethyl)-3-cyclohexyl-N-cyclopentylpropanamide |
| 354 | 5-bromo-2-chloro-N-(2-{5-[3-chloro-4-(methyloxy)phenyl]-3-pyridin-4-yl-1H-1,2,4-triazol-1-yl}ethyl)-N-cyclopentylbenzamide |
| 355 | N-(2-{5-[3-chloro-4-(methyloxy)phenyl]-3-pyridin-4-yl-1H-1,2,4-triazol-1-yl}ethyl)-N-cyclopentyl-2-(phenylmethyl)benzamide |
| 356 | N-(2-{5-[3-chloro-4-(methyloxy)phenyl]-3-pyridin-4-yl-1H-1,2,4-triazol-1-yl}ethyl)-N-cyclopentyl-4-methyl-3-(methyloxy)benzamide |
| 357 | N-(2-{5-[3-chloro-4-(methyloxy)phenyl]-3-pyridin-4-yl-1H-1,2,4-triazol-1-yl}ethyl)-N-cyclopentyl-2-[6-(methyloxy)-3-oxo-2,3-dihydro-1H-inden-1-yl]acetamide |
| 358 | N-(2-{5-[3-chloro-4-(methyloxy)phenyl]-3-pyridin-4-yl-1H-1,2,4-triazol-1-yl}ethyl)-N-cyclopentyl-5-oxo-5-phenylpentanamide |
| 359 | N-(2-{5-[3-chloro-4-(methyloxy)phenyl]-3-pyridin-4-yl-1H-1,2,4-triazol-1-yl}ethyl)-N-cyclopentyl-2-nitro-4-(trifluoromethyl)benzamide |
| 360 | N-(2-{5-[3-chloro-4-(methyloxy)phenyl]-3-pyridin-4-yl-1H-1,2,4-triazol-1-yl}ethyl)-N-cyclopentyl-5-methyl-2-nitrobenzamide |

TABLE 3-continued

| Entry | Name |
|---|---|
| 361 | N-(2-{5-[3-chloro-4-(methyloxy)phenyl]-3-pyridin-4-yl-1H-1,2,4-triazol-1-yl}ethyl)-N-cyclopentyl-2-(4-nitrophenyl)propanamide |
| 362 | 3-(1H-benzimidazol-2-yl)-N-(2-{5-[3-chloro-4-(methyloxy)phenyl]-3-pyridin-4-yl-1H-1,2,4-triazol-1-yl}ethyl)-N-cyclopentylpropanamide |
| 363 | N-(2-{5-[3-chloro-4-(methyloxy)phenyl]-3-pyridin-4-yl-1H-1,2,4-triazol-1-yl}ethyl)-N-cyclopentyl-5-fluoro-2-methylbenzamide |
| 364 | 2,6-dichloro-N-(2-{5-[3-chloro-4-(methyloxy)phenyl]-3-pyridin-4-yl-1H-1,2,4-triazol-1-yl}ethyl)-N-cyclopentylpyridine-3-carboxamide |
| 365 | N-(2-{5-[3-chloro-4-(methyloxy)phenyl]-3-pyridin-4-yl-1H-1,2,4-triazol-1-yl}ethyl)-N-cyclopentyl-4-nitro-1H-pyrazole-3-carboxamide |
| 366 | N-(2-{5-[3-chloro-4-(methyloxy)phenyl]-3-pyridin-4-yl-1H-1,2,4-triazol-1-yl}ethyl)-N-cyclopentyl-5-nitro-1H-pyrazole-3-carboxamide |
| 367 | N-(2-{5-[3-chloro-4-(methyloxy)phenyl]-3-pyridin-4-yl-1H-1,2,4-triazol-1-yl}ethyl)-N-cyclopentyl-3-(phenylcarbonyl)pyridine-2-carboxamide |
| 368 | N-(2-{5-[3-chloro-4-(methyloxy)phenyl]-3-pyridin-4-yl-1H-1,2,4-triazol-1-yl}ethyl)-N-cyclopentyl-3-[(trifluoromethyl)thio]benzamide |
| 369 | N-(2-{5-[3-chloro-4-(methyloxy)phenyl]-3-pyridin-4-yl-1H-1,2,4-triazol-1-yl}ethyl)-N-cyclopentyl-4-[(phenylmethyl)oxy]butanamide |
| 370 | N-(2-{5-[3-chloro-4-(methyloxy)phenyl]-3-pyridin-4-yl-1H-1,2,4-triazol-1-yl}ethyl)-N-cyclopentyl-2-(propyloxy)benzamide |
| 371 | 2-acetyl-N-(2-{5-[3-chloro-4-(methyloxy)phenyl]-3-pyridin-4-yl-1H-1,2,4-triazol-1-yl}ethyl)-N-cyclopentylbenzamide |
| 372 | N-(2-{5-[3-chloro-4-(methyloxy)phenyl]-3-pyridin-4-yl-1H-1,2,4-triazol-1-yl}ethyl)-N-cyclopentyl-4-(4-nitrophenyl)butanamide |
| 373 | N-(2-{5-[3-chloro-4-(methyloxy)phenyl]-3-pyridin-4-yl-1H-1,2,4-triazol-1-yl}ethyl)-N-cyclopentyl-9-oxo-9H-fluorene-1-carboxamide |
| 374 | N-(2-{5-[3-chloro-4-(methyloxy)phenyl]-3-pyridin-4-yl-1H-1,2,4-triazol-1-yl}ethyl)-N-cyclopentyl-2,2,3,3-tetramethylcyclopropanecarboxamide |
| 375 | 2-[(4-acetylphenyl)oxy]-N-(2-{5-[3-chloro-4-(methyloxy)phenyl]-3-pyridin-4-yl-1H-1,2,4-triazol-1-yl}ethyl)-N-cyclopentylacetamide |
| 376 | N-(2-{5-[3-chloro-4-(methyloxy)phenyl]-3-pyridin-4-yl-1H-1,2,4-triazol-1-yl}ethyl)-N-cyclopentyl-3-fluoro-2-methylbenzamide |
| 377 | N-(2-{5-[3-chloro-4-(methyloxy)phenyl]-3-pyridin-4-yl-1H-1,2,4-triazol-1-yl}ethyl)-N-cyclopentyl-N'-[(1R)-1-phenylethyl]butanediamide |
| 378 | N-(2-{5-[3-chloro-4-(methyloxy)phenyl]-3-pyridin-4-yl-1H-1,2,4-triazol-1-yl}ethyl)-N-cyclopentyl-5-(4-nitrophenyl)furan-2-carboxamide |
| 379 | N-(2-{5-[3-chloro-4-(methyloxy)phenyl]-3-pyridin-4-yl-1H-1,2,4-triazol-1-yl}ethyl)-N-cyclopentyl-3-[4-(trifluoromethyl)phenyl]propanamide |
| 380 | N-(2-{5-[3-chloro-4-(methyloxy)phenyl]-3-pyridin-4-yl-1H-1,2,4-triazol-1-yl}ethyl)-N-cyclopentyl-5-(3-nitrophenyl)furan-2-carboxamide |
| 381 | N-(2-{5-[3-chloro-4-(methyloxy)phenyl]-3-pyridin-4-yl-1H-1,2,4-triazol-1-yl}ethyl)-N-cyclopentyl-3-(3,4-difluorophenyl)propanamide |
| 382 | 5-(aminosulfonyl)-2-chloro-N-(2-{5-[3-chloro-4-(methyloxy)phenyl]-3-pyridin-4-yl-1H-1,2,4-triazol-1-yl}ethyl)-N-cyclopentyl-4-fluorobenzamide |
| 383 | N-(2-{5-[3-chloro-4-(methyloxy)phenyl]-3-pyridin-4-yl-1H-1,2,4-triazol-1-yl}ethyl)-N-cyclopentyl-2-(2-oxocyclopentyl)acetamide |
| 384 | N-(2-{5-[3-chloro-4-(methyloxy)phenyl]-3-pyridin-4-yl-1H-1,2,4-triazol-1-yl}ethyl)-N-cyclopentyl-2-[(4-fluorophenyl)carbonyl]benzamide |
| 385 | N-(2-{5-[3-chloro-4-(methyloxy)phenyl]-3-pyridin-4-yl-1H-1,2,4-triazol-1-yl}ethyl)-2-[(4-chlorophenyl)carbonyl]-N-cyclopentylbenzamide |
| 386 | N-{3-[(2-{5-[3-chloro-4-(methyloxy)phenyl]-3-pyridin-4-yl-1H-1,2,4-triazol-1-yl}ethyl)(cyclopentyl)amino]-3-oxopropyl}-4-nitrobenzamide |
| 387 | N-(2-{5-[3-chloro-4-(methyloxy)phenyl]-3-pyridin-4-yl-1H-1,2,4-triazol-1-yl}ethyl)-N-cyclopentyl-2-(methyloxy)-4-(methylthio)benzamide |
| 388 | N-(2-{5-[3-chloro-4-(methyloxy)phenyl]-3-pyridin-4-yl-1H-1,2,4-triazol-1-yl}ethyl)-N-cyclopentyl-3-(4-methylphenyl)propanamide |
| 389 | 5-chloro-N-(2-{5-[3-chloro-4-(methyloxy)phenyl]-3-pyridin-4-yl-1H-1,2,4-triazol-1-yl}ethyl)-N-cyclopentyl-2-(methyloxy)benzamide |
| 390 | 4-acetyl-N-(2-{5-[3-chloro-4-(methyloxy)phenyl]-3-pyridin-4-yl-1H-1,2,4-triazol-1-yl}ethyl)-N-cyclopentyl-3,5-dimethyl-1H-pyrrole-2-carboxamide |
| 391 | N-(2-{5-[3-chloro-4-(methyloxy)phenyl]-3-pyridin-4-yl-1H-1,2,4-triazol-1-yl}ethyl)-N-cyclopentyl-6-oxoheptanamide |
| 392 | N-(2-{5-[3-chloro-4-(methyloxy)phenyl]-3-pyridin-4-yl-1H-1,2,4-triazol-1-yl}ethyl)-N-cyclopentyl-3,3-dimethyl-2-(phenylmethyl)butanamide |
| 393 | N-(2-{5-[3-chloro-4-(methyloxy)phenyl]-3-pyridin-4-yl-1H-1,2,4-triazol-1-yl}ethyl)-N-cyclopentyl-2-(2-fluorobiphenyl-4-yl)propanamide |
| 394 | N-(2-{5-[3-chloro-4-(methyloxy)phenyl]-3-pyridin-4-yl-1H-1,2,4-triazol-1-yl}ethyl)-N-cyclopentyl-3-oxo-2,3-dihydro-1H-indene-1-carboxamide |
| 395 | 2-{[2,4-bis(1,1-dimethylpropyl)phenyl]oxy}-N-(2-{5-[3-chloro-4-(methyloxy)phenyl]-3-pyridin-4-yl-1H-1,2,4-triazol-1-yl}ethyl)-N-cyclopentylacetamide |
| 396 | 4-{[2,4-bis(1,1-dimethylpropyl)phenyl]oxy}-N-(2-{5-[3-chloro-4-(methyloxy)phenyl]-3-pyridin-4-yl-1H-1,2,4-triazol-1-yl}ethyl)-N-cyclopentylbutanamide |
| 397 | 4-[3,4-bis(methyloxy)phenyl]-N-(2-{5-[3-chloro-4-(methyloxy)phenyl]-3-pyridin-4-yl-1H-1,2,4-triazol-1-yl}ethyl)-N-cyclopentylbutanamide |
| 398 | N-(2-{5-[3-chloro-4-(methyloxy)phenyl]-3-pyridin-4-yl-1H-1,2,4-triazol-1-yl}ethyl)-N-cyclopentyl-4-(1,2-dihydroacenaphthylen-5-yl)-4-oxobutanamide |

TABLE 3-continued

| Entry | Name |
|---|---|
| 399 | N-(2-{5-[3-chloro-4-(methyloxy)phenyl]-3-pyridin-4-yl-1H-1,2,4-triazol-1-yl}ethyl)-N-cyclopentyl-5-[3-(trifluoromethyl)phenyl]furan-2-carboxamide |
| 400 | N-(2-{5-[3-chloro-4-(methyloxy)phenyl]-3-pyridin-4-yl-1H-1,2,4-triazol-1-yl}ethyl)-N-cyclopentyl-1-{[4-(1,1-dimethylethyl)phenyl]sulfonyl}-L-prolinamide |
| 401 | N-(2-{5-[3-chloro-4-(methyloxy)phenyl]-3-pyridin-4-yl-1H-1,2,4-triazol-1-yl}ethyl)-N-cyclopentyl-2-(1H-indol-3-yl)-2-oxoacetamide |
| 402 | N-(2-{5-[3-chloro-4-(methyloxy)phenyl]-3-pyridin-4-yl-1H-1,2,4-triazol-1-yl}ethyl)-2-[(4-chloro-3-nitrophenyl)carbonyl]-N-cyclopentylbenzamide |
| 403 | N-(2-{5-[3-chloro-4-(methyloxy)phenyl]-3-pyridin-4-yl-1H-1,2,4-triazol-1-yl}ethyl)-N-cyclopentyl-2-(ethylthio)-2,2-diphenylacetamide |
| 404 | N-(2-{5-[3-chloro-4-(methyloxy)phenyl]-3-pyridin-4-yl-1H-1,2,4-triazol-1-yl}ethyl)-N-cyclopentyl-2,2-dimethylpent-4-enamide |
| 405 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]benzene-1,2-dicarboxamide |
| 406 | N-(2-{5-[3-chloro-4-(methyloxy)phenyl]-3-pyridin-4-yl-1H-1,2,4-triazol-1-yl}ethyl)-N-cyclopentyl-6-nitrohexanamide |
| 407 | N-(2-{5-[3-chloro-4-(methyloxy)phenyl]-3-pyridin-4-yl-1H-1,2,4-triazol-1-yl}ethyl)-N-cyclopentyl-N~2~-(1H-indol-3-ylacetyl)-L-valinamide |
| 408 | 2,6-dichloro-N-(2-{5-[3-chloro-4-(methyloxy)phenyl]-3-pyridin-4-yl-1H-1,2,4-triazol-1-yl}ethyl)-N-cyclopentyl-3-nitrobenzamide |
| 409 | N-(2-{5-[3-chloro-4-(methyloxy)phenyl]-3-pyridin-4-yl-1H-1,2,4-triazol-1-yl}ethyl)-N-cyclopentyl-N'-[(1S)-1-phenylethyl]butanediamide |
| 410 | N-(2-{5-[3-chloro-4-(methyloxy)phenyl]-3-pyridin-4-yl-1H-1,2,4-triazol-1-yl}ethyl)-N-cyclopentyl-2-fluoro-5-methylbenzamide |
| 411 | N-(2-{5-[3-chloro-4-(methyloxy)phenyl]-3-pyridin-4-yl-1H-1,2,4-triazol-1-yl}ethyl)-N-cyclopentyl-N',N'-bis[(1R)-1-phenylethyl]benzene-1,2-dicarboxamide |
| 412 | 3-[2,5-bis(trifluoromethyl)phenyl]-N-(2-{5-[3-chloro-4-(methyloxy)phenyl]-3-pyridin-4-yl-1H-1,2,4-triazol-1-yl}ethyl)-N-cyclopentylpropanamide |
| 413 | N-(2-{5-[3-chloro-4-(methyloxy)phenyl]-3-pyridin-4-yl-1H-1,2,4-triazol-1-yl}ethyl)-2-[(2-chlorophenyl)oxy]-N-cyclopentylacetamide |
| 414 | N-(2-{5-[3-chloro-4-(methyloxy)phenyl]-3-pyridin-4-yl-1H-1,2,4-triazol-1-yl}ethyl)-N-cyclopentyl-3,5-dimethyl-4-nitrobenzamide |
| 415 | 3-(1,3-benzodioxol-5-yl)-N-(2-{5-[3-chloro-4-(methyloxy)phenyl]-3-pyridin-4-yl-1H-1,2,4-triazol-1-yl}ethyl)-N-cyclopentylpropanamide |
| 416 | N-(2-{5-[3-chloro-4-(methyloxy)phenyl]-3-pyridin-4-yl-1H-1,2,4-triazol-1-yl}ethyl)-N-cyclopentyl-2-[(2-nitrophenyl)oxy]acetamide |
| 417 | 3-bromo-N-(2-{5-[3-chloro-4-(methyloxy)phenyl]-3-pyridin-4-yl-1H-1,2,4-triazol-1-yl}ethyl)-N-cyclopentyl-4-(methyloxy)benzamide |
| 418 | N-(2-{5-[3-chloro-4-(methyloxy)phenyl]-3-pyridin-4-yl-1H-1,2,4-triazol-1-yl}ethyl)-N-cyclopentyl-3-(1,3-dioxo-1,3-dihydro-2H-isoindol-2-yl)propanamide |
| 419 | 5-chloro-N-(2-{5-[3-chloro-4-(methyloxy)phenyl]-3-pyridin-4-yl-1H-1,2,4-triazol-1-yl}ethyl)-N-cyclopentylthiophene-2-carboxamide |
| 420 | N-(2-{5-[3-chloro-4-(methyloxy)phenyl]-3-pyridin-4-yl-1H-1,2,4-triazol-1-yl}ethyl)-N-cyclopentyl-2-phenyl-2-(phenylthio)acetamide |
| 421 | N-(2-{5-[3-chloro-4-(methyloxy)phenyl]-3-pyridin-4-yl-1H-1,2,4-triazol-1-yl}ethyl)-N-cyclopentyl-2-(phenylcarbonyl)benzamide |
| 422 | 5-acetyl-N-(2-{5-[3-chloro-4-(methyloxy)phenyl]-3-pyridin-4-yl-1H-1,2,4-triazol-1-yl}ethyl)-N-cyclopentylthiophene-2-carboxamide |
| 423 | N-(2-{5-[3-chloro-4-(methyloxy)phenyl]-3-pyridin-4-yl-1H-1,2,4-triazol-1-yl}ethyl)-N-cyclopentyl-4-[4-(methyloxy)phenyl]butanamide |
| 424 | 5-bromo-N-(2-{5-[3-chloro-4-(methyloxy)phenyl]-3-pyridin-4-yl-1H-1,2,4-triazol-1-yl}ethyl)-N-cyclopentylthiophene-2-carboxamide |
| 425 | N-(2-{5-[3-chloro-4-(methyloxy)phenyl]-3-pyridin-4-yl-1H-1,2,4-triazol-1-yl}ethyl)-N-cyclopentyl-4-nitrobenzamide |
| 426 | N-(2-{5-[3-chloro-4-(methyloxy)phenyl]-3-pyridin-4-yl-1H-1,2,4-triazol-1-yl}ethyl)-N-cyclopentyl-9H-xanthene-9-carboxamide |
| 427 | N~2~-acetyl-N-(2-{5-[3-chloro-4-(methyloxy)phenyl]-3-pyridin-4-yl-1H-1,2,4-triazol-1-yl}ethyl)-N-cyclopentylvalinamide |
| 428 | N-cyclopentyl-N-{2-[5-methyl-3-(2-{[(3R)-pyrrolidin-3-ylmethyl]amino}pyridin-4-yl)-1H-1,2,4-triazol-1-yl]ethyl}-2-naphthalen-1-ylacetamide |
| 429 | N-cyclopentyl-N-{2-[5-methyl-3-(2-{[(3S)-pyrrolidin-3-ylmethyl]amino}pyridin-4-yl)-1H-1,2,4-triazol-1-yl]ethyl}-2-naphthalen-1-ylacetamide |
| 430 | N-[4-(1-{2-[cyclopentyl(naphthalen-1-ylacetyl)amino]ethyl}-5-methyl-1H-1,2,4-triazol-3-yl)pyridin-2-yl]-N~2~,N~2~-dimethylglycinamide |
| 431 | N-cyclopentyl-N-{2-[5-methyl-3-(2-{[(methyloxy)acetyl]amino}pyridin-4-yl)-1H-1,2,4-triazol-1-yl]ethyl}-2-naphthalen-1-ylacetamide |
| 432 | N-[4-(1-{2-[cyclopentyl(naphthalen-1-ylacetyl)amino]ethyl}-5-methyl-1H-1,2,4-triazol-3-yl)pyridin-2-yl]propanamide |
| 433 | N-cyclopentyl-N-[2-(5-methyl-3-{2-[(phenylacetyl)amino]pyridin-4-yl}-1H-1,2,4-triazol-1-yl)ethyl]-2-naphthalen-1-ylacetamide |
| 434 | N-[4-(1-{2-[cyclopentyl(naphthalen-1-ylacetyl)amino]ethyl}-5-methyl-1H-1,2,4-triazol-3-yl)pyridin-2-yl]benzamide |

TABLE 3-continued

| Entry | Name |
|---|---|
| 435 | N-(2-{3-[2-(acetylamino)pyridin-4-yl]-5-methyl-1H-1,2,4-triazol-1-yl}ethyl)-N-cyclopentyl-2-naphthalen-1-ylacetamide |
| 436 | 2-(5-bromo-1H-indol-3-yl)-N-cyclopentyl-N-[2-(5-methyl-3-pyridin-4-yl-1H-1,2,4-triazol-1-yl)ethyl]acetamide |
| 437 | N-cyclopentyl-2-[5-(methyloxy)-1H-indol-3-yl]-N-[2-(5-methyl-3-pyridin-4-yl-1H-1,2,4-triazol-1-yl)ethyl]acetamide |
| 438 | N-cyclopentyl-2-(1H-indol-3-yl)-N-[2-(5-methyl-3-pyridin-4-yl-1H-1,2,4-triazol-1-yl)ethyl]acetamide |
| 439 | methyl [4-(1-{2-[cyclopentyl(naphthalen-1-ylacetyl)amino]ethyl}-5-methyl-1H-1,2,4-triazol-3-yl)pyridin-2-yl]carbamate |
| 440 | phenylmethyl [4-(1-{2-[cyclopentyl(naphthalen-1-ylacetyl)amino]ethyl}-5-methyl-1H-1,2,4-triazol-3-yl)pyridin-2-yl]carbamate |
| 441 | propyl [4-(1-{2-[cyclopentyl(naphthalen-1-ylacetyl)amino]ethyl}-5-methyl-1H-1,2,4-triazol-3-yl)pyridin-2-yl]carbamate |
| 442 | N-[4-(1-{2-[cyclopentyl(naphthalen-1-ylacetyl)amino]ethyl}-5-methyl-1H-1,2,4-triazol-3-yl)pyridin-2-yl]furan-3-carboxamide |
| 443 | N-cyclopentyl-N-[2-(5-methyl-3-{2-[(methylsulfonyl)amino]pyridin-4-yl}-1H-1,2,4-triazol-1-yl)ethyl]-2-naphthalen-1-ylacetamide |
| 444 | N-cyclopentyl-N-[2-(5-methyl-3-{2-[(phenylsulfonyl)amino]pyridin-4-yl}-1H-1,2,4-triazol-1-yl)ethyl]-2-naphthalen-1-ylacetamide |
| 445 | N-cyclopentyl-N-{2-[5-methyl-3-(2-{[(phenylmethyl)sulfonyl]amino}pyridin-4-yl)-1H-1,2,4-triazol-1-yl]ethyl}-2-naphthalen-1-ylacetamide |
| 446 | N-cyclopentyl-N-(2-{5-methyl-3-[2-({[(phenylmethyl)amino]carbonyl}amino)pyridin-4-yl]-1H-1,2,4-triazol-1-yl}ethyl)-2-naphthalen-1-ylacetamide |
| 447 | N-[4-(1-{2-[cyclopentyl(naphthalen-1-ylacetyl)amino]ethyl}-5-methyl-1H-1,2,4-triazol-3-yl)pyridin-2-yl]-1-ethylpiperidine-4-carboxamide |
| 448 | N-cyclopentyl-2-(2-methyl-3H-indol-3-yl)-N-[2-(5-methyl-3-pyridin-4-yl-1H-1,2,4-triazol-1-yl)ethyl]acetamide |
| 449 | N-cyclopentyl-N-[2-(5-methyl-3-pyridin-4-yl-1H-1,2,4-triazol-1-yl)ethyl]-2-naphthalen-1-ylpropanamide |
| 450 | N-[4-(1-{2-[cyclopentyl(naphthalen-1-ylacetyl)amino]ethyl}-5-methyl-1H-1,2,4-triazol-3-yl)pyridin-2-yl]-N~3~,N~3~-dimethyl-beta-alaninamide |
| 451 | N-[4-(1-{2-[cyclopentyl(naphthalen-1-ylacetyl)amino]ethyl}-5-methyl-1H-1,2,4-triazol-3-yl)pyridin-2-yl]pentanamide |
| 452 | N-{2-[3-(2-aminopyrimidin-4-yl)-5-methyl-1H-1,2,4-triazol-1-yl]ethyl}-N-cyclopentyl-2-naphthalen-1-ylacetamide |
| 453 | N-[4-(1-{2-[cyclopentyl(naphthalen-1-ylacetyl)amino]ethyl}-5-methyl-1H-1,2,4-triazol-3-yl)pyridin-2-yl]-1-methylpiperidine-3-carboxamide |
| 454 | 2-(4-methylpiperazin-1-yl)ethyl [4-(1-{2-[cyclopentyl(naphthalen-1-ylacetyl)amino]ethyl}-5-methyl-1H-1,2,4-triazol-3-yl)pyridin-2-yl]carbamate |
| 455 | 2-(methyloxy)ethyl [4-(1-{2-[cyclopentyl(naphthalen-1-ylacetyl)amino]ethyl}-5-methyl-1H-1,2,4-triazol-3-yl)pyridin-2-yl]carbamate |
| 456 | 2-morpholin-4-ylethyl [4-(1-{2-[cyclopentyl(naphthalen-1-ylacetyl)amino]ethyl}-5-methyl-1H-1,2,4-triazol-3-yl)pyridin-2-yl]carbamate |
| 457 | N-{2-[5-(2-aminopyrimidin-4-yl)-3-methyl-1H-1,2,4-triazol-1-yl]ethyl}-N-cyclopentyl-2-naphthalen-1-ylacetamide |
| 458 | methyl {4-[1-(2-{cyclopropyl[(naphthalen-1-ylamino)carbonyl]amino}ethyl)-1H-1,2,4-triazol-3-yl]pyridin-2-yl}carbamate |
| 459 | methyl [4-(1-{2-[{[(3-chloro-2-methylphenyl)amino]carbonyl}(cyclopentyl)amino]ethyl}-5-methyl-1H-1,2,4-triazol-3-yl)pyridin-2-yl]carbamate |
| 460 | methyl {4-[1-(2-{cyclopentyl[(naphthalen-1-ylamino)carbonyl]amino}ethyl)-5-methyl-1H-1,2,4-triazol-3-yl]pyridin-2-yl}carbamate |
| 461 | methyl {4-[1-(2-{cyclopentyl[(1-naphthalen-1-ylcyclopropyl)carbonyl]amino}ethyl)-5-methyl-1H-1,2,4-triazol-3-yl]pyridin-2-yl}carbamate |
| 462 | 2-piperidin-1-ylethyl [4-(1-{2-[cyclopentyl(naphthalen-1-ylacetyl)amino]ethyl}-5-methyl-1H-1,2,4-triazol-3-yl)pyridin-2-yl]carbamate |
| 463 | N-{2-[3-(2-aminopyrimidin-4-yl)-5-(trifluoromethyl)-1H-1,2,4-triazol-1-yl]ethyl}-N-cyclopentyl-2-naphthalen-1-ylacetamide |
| 464 | N-{2-[5-(2-aminopyrimidin-4-yl)-3-(trifluoromethyl)-1H-1,2,4-triazol-1-yl]ethyl}-N-cyclopentyl-2-naphthalen-1-ylacetamide |
| 465 | N-cyclopentyl-N-[2-(5-methyl-3-pyrimidin-4-yl-1H-1,2,4-triazol-1-yl)ethyl]-2-naphthalen-1-ylacetamide |
| 466 | N-{2-[3-(2-aminopyrimidin-4-yl)-1H-1,2,4-triazol-1-yl]ethyl}-N-cyclopentyl-2-naphthalen-1-ylacetamide |
| 467 | methyl (4-{1-[2-(cyclopentyl{[(2-ethylphenyl)amino]carbonyl}amino)ethyl]-5-methyl-1H-1,2,4-triazol-3-yl}pyridin-2-yl)carbamate |
| 468 | methyl [4-(1-{2-[{[(3-bromo-2-methylphenyl)amino]carbonyl}(cyclopentyl)amino]ethyl}-5-methyl-1H-1,2,4-triazol-3-yl)pyridin-2-yl]carbamate |
| 469 | methyl [4-(1-{2-[cyclopentyl({[4-fluoro-2-(trifluoromethyl)phenyl]amino}carbonyl)amino]ethyl}-5-methyl-1H-1,2,4-triazol-3-yl)pyridin-2-yl]carbamate |
| 470 | methyl (4-{1-[2-(cyclopentyl{[(2-methylphenyl)amino]carbonyl}amino)ethyl]-5-methyl-1H-1,2,4-triazol-3-yl}pyridin-2-yl)carbamate |

TABLE 3-continued

| Entry | Name |
|---|---|
| 471 | methyl (4-{1-[2-(cyclopentyl{[(3-fluoro-2-methylphenyl)amino]carbonyl}amino)ethyl]-5-methyl-1H-1,2,4-triazol-3-yl}pyridin-2-yl)carbamate |
| 472 | methyl (4-{1-[2-(cyclopentyl{[(4-fluoro-2-methylphenyl)amino]carbonyl}amino)ethyl]-5-methyl-1H-1,2,4-triazol-3-yl}pyridin-2-yl)carbamate |
| 473 | methyl [4-(1-{2-[cyclopentyl(phenylacetyl)amino]ethyl}-5-ethyl-1H-1,2,4-triazol-3-yl)pyridin-2-yl]carbamate |
| 474 | methyl {4-[1-{2-[cyclopentyl(naphthalen-1-ylacetyl)amino]ethyl}-5-(trifluoromethyl)-1H-1,2,4-triazol-3-yl]pyridin-2-yl}carbamate |
| 475 | methyl [4-(1-{2-[acetyl(cyclopropyl)amino]ethyl}-5-ethyl-1H-1,2,4-triazol-3-yl)pyridin-2-yl]carbamate |
| 476 | methyl [4-(1-{2-[acetyl(cyclopentyl)amino]ethyl}-5-ethyl-1H-1,2,4-triazol-3-yl)pyridin-2-yl]carbamate |
| 477 | 2-(4-methylpiperazin-1-yl)ethyl {4-[1-(2-{cyclopentyl[(naphthalen-1-ylamino)carbonyl]amino}ethyl)-5-methyl-1H-1,2,4-triazol-3-yl]pyridin-2-yl}carbamate. |

16. The method according to any of claims 1-15, wherein treating said kinase-dependent disease or condition comprises modulating the in vivo activity of Tie-2.

17. The method according to claim 16, wherein modulating the in vivo activity of Tie-2 comprises inhibition of Tie-2.

18. The method according to claim 1, wherein the compound is according to one of,

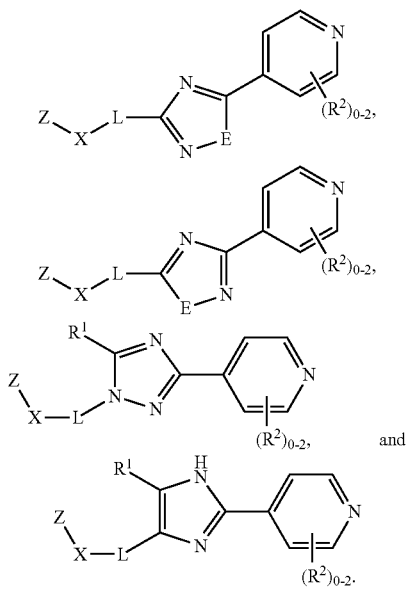

and

19. The method according to claim 18, wherein $R^4$ is either optionally substituted aryl $C_{1-6}$ alkyl or optionally substituted heteroaryl $C_{1-6}$ alkyl.

20. The method according to claim 19, wherein $R^1$ is selected from —H, optionally substituted $C_{1-6}$ alkyl, optionally substituted aryl, and optionally substituted heteroaryl.

21. The method according to claim 20, wherein L is optionally substituted —$CH_2CH_2$—.

22. The method according to claim 21, wherein $R^3$ is optionally substituted cycloalkyl or optionally substituted branched alkyl.

23. The method according to claim 22, wherein Z is $R^4C(=O)$—.

24. The method according to claim 23, wherein L is —$CH_2CH_2$—.

25. The method according to claim 24, wherein $R^4$ is optionally substituted aryl $C_{1-6}$ alkyl.

26. The method according to claim 25, wherein $R^4$ is optionally substituted —$CH_2$-naphthylene.

27. The method according to claim 26, wherein $R^4$ is optionally substituted —$CH_2$-1-naphthylene.

28. The method according to claim 27, wherein $R^4$ is —$CH_2$-1-naphthylene.

29. The method according to claim 28, wherein at least one of $R^2$ is selected from —$NH_2$, —$N(R^6)R^7$, —$N(R^6)N(R^6)R^7$, —$N(R^6)C(O)R^7$, —$N(R^6)C(O)C_{0-6}$alkyl-$N(R^6)R^7$, and —$N(R^6)CO_2R^7$.

30. The method according to claim 29, wherein said at least one of $R^2$ is ortho to the nitrogen of the pyridine ring bearing $R^2$.

* * * * *